US010852290B2

(12) United States Patent
Hsu et al.

(10) Patent No.: US 10,852,290 B2
(45) Date of Patent: Dec. 1, 2020

(54) ANALYSIS ACCURACY IMPROVEMENT IN AUTOMATED TESTING APPARATUS

(71) Applicant: Bonraybio Co., Ltd., Taichung (TW)

(72) Inventors: Cheng-Teng Hsu, Taichung (TW); Chih-Pin Chang, Taichung (TW); Kuang-Li Huang, Taichung (TW); Yu-Chiao Chi, Taichung (TW); Chia-Wei Chang, Taichung (TW); Chiung-Han Wang, Taichung (TW)

(73) Assignee: Bonraybio Co., Ltd., Taichung (TW)

( * ) Notice: Subject to any disclaimer, the term of this patent is extended or adjusted under 35 U.S.C. 154(b) by 0 days.

(21) Appl. No.: 16/443,699

(22) Filed: Jun. 17, 2019

(65) Prior Publication Data
US 2019/0302093 A1 Oct. 3, 2019

Related U.S. Application Data

(63) Continuation-in-part of application No. 16/101,336, filed on Aug. 10, 2018, now Pat. No. 10,324,022, which is a continuation-in-part of application No. 15/966,479, filed on Apr. 30, 2018, now Pat. No. 10,281,386, which is a continuation-in-part of application No. 15/603,783, filed on May 24, 2017, now Pat. No. 9,959,621, which is a continuation-in-part of application No. 15/345,061, filed on Nov. 7, 2016, now Pat. No. 9,958,665, which is a continuation-in-part of application No. 15/152,470, filed on May 11, 2016, now Pat. No. 9,958,658.

(51) Int. Cl.
*G01N 33/48* (2006.01)
*G01N 1/28* (2006.01)
*H04N 5/232* (2006.01)
*H04N 5/225* (2006.01)
*G01N 21/17* (2006.01)

(52) U.S. Cl.
CPC .......... *G01N 33/48* (2013.01); *G01N 1/2806* (2013.01); *G01N 21/17* (2013.01); *H04N 5/2259* (2013.01); *H04N 5/23212* (2013.01); *G01N 2021/177* (2013.01)

(58) Field of Classification Search
None
See application file for complete search history.

(56) References Cited

U.S. PATENT DOCUMENTS

2007/0122143 A1* 5/2007 Okamoto ............. G02B 21/244
396/432
2015/0078642 A1* 3/2015 Fang ...................... G06T 15/00
382/131

\* cited by examiner

*Primary Examiner* — Eileen M Adams
(74) *Attorney, Agent, or Firm* — Perkins Coie LLP; Han-Wei Chen

(57) ABSTRACT

Embodiments disclose a device for testing biological specimen. The device includes a receiving mechanism to receive a carrier. The carrier includes a holding area that carries or has been exposed to the biological specimen. The device includes a camera module arranged to capture imagery of the holding area. The camera module includes an focusing motor operable to adjust a focal point of the camera. The device also includes a processor that is configured to utilize the camera module to determine, based on operations of the focusing motor, a volumetric property of the holding area and perform a set of analytic processes on at least a portion of the captured imagery of the holding area to determine one or more properties of the biological specimen.

22 Claims, 58 Drawing Sheets

| 125 | 133 | 105 | 133 | 122 |
|---|---|---|---|---|
| 140 | 153 | 162 | 102 | 163 |
| 163 | 185 | 190 | 161 | 172 |
| 190 | 203 | 211 | 201 | 179 |
| 196 | 212 | 217 | 207 | 183 |
| 191 | 200 | 212 | 200 | 178 |
| 165 | 185 | 146 | 176 | 166 |
| 138 | 150 | 152 | 140 | 132 |
| 107 | 112 | 111 | 109 | 103 |

Candidate Segments 3510

FIG. 35

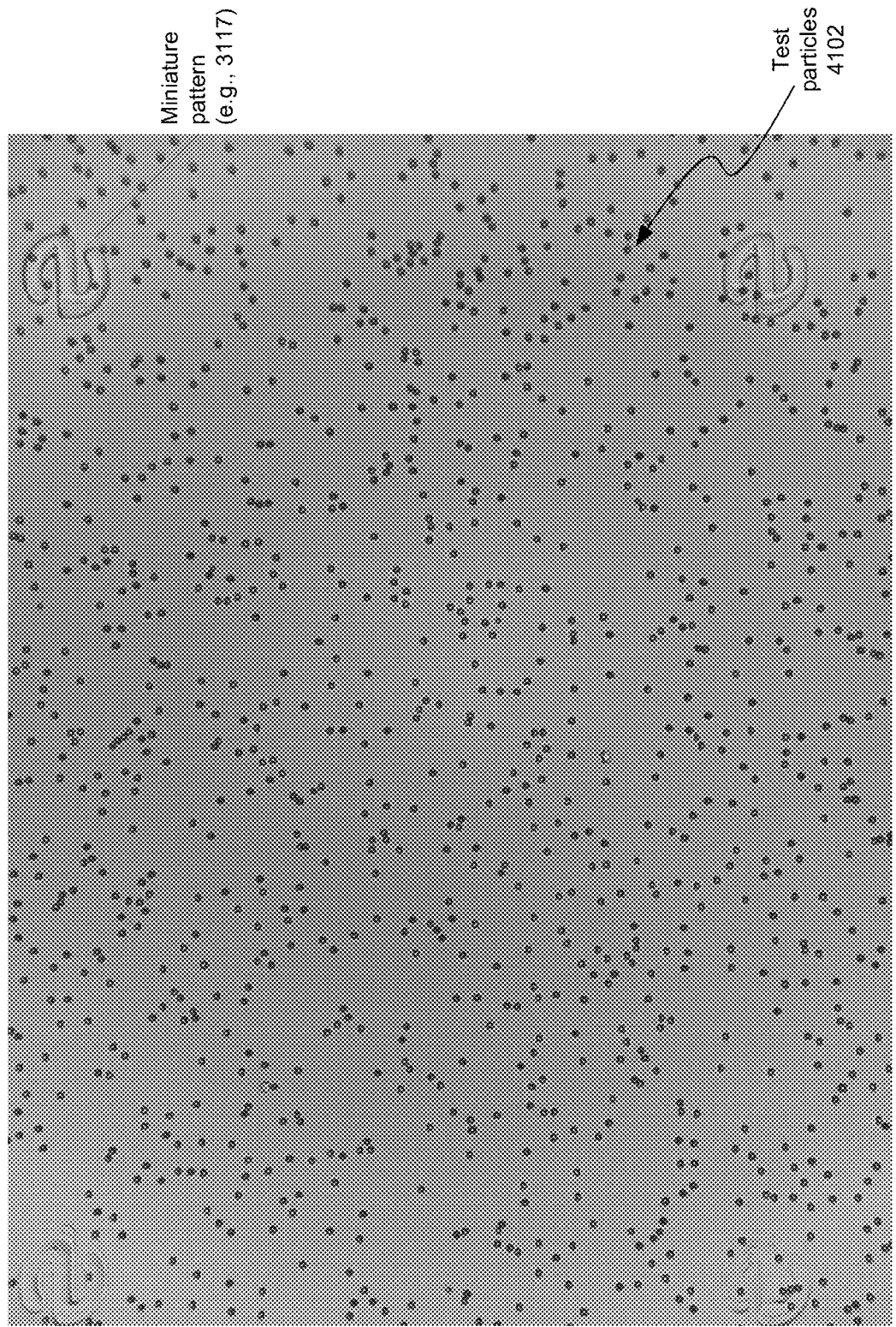

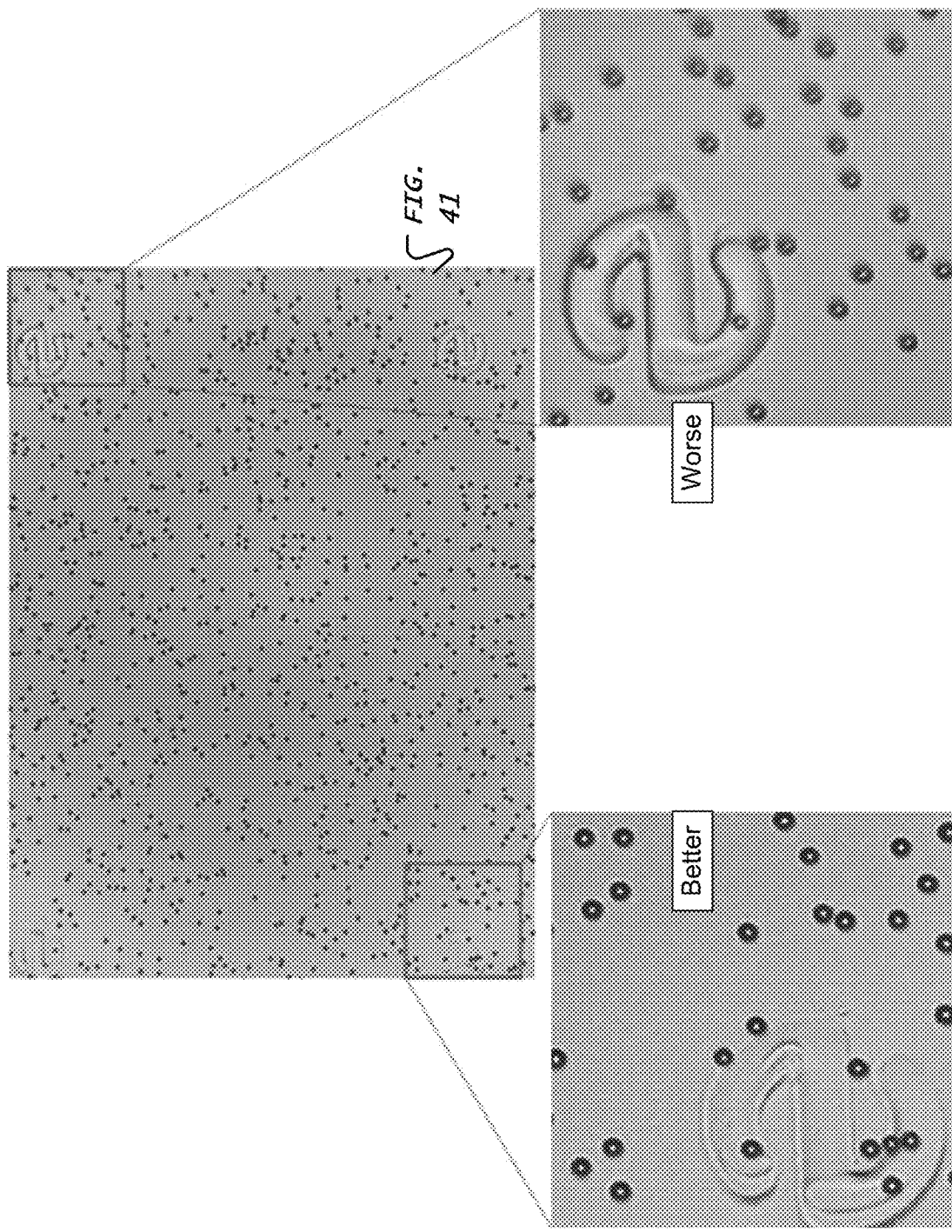

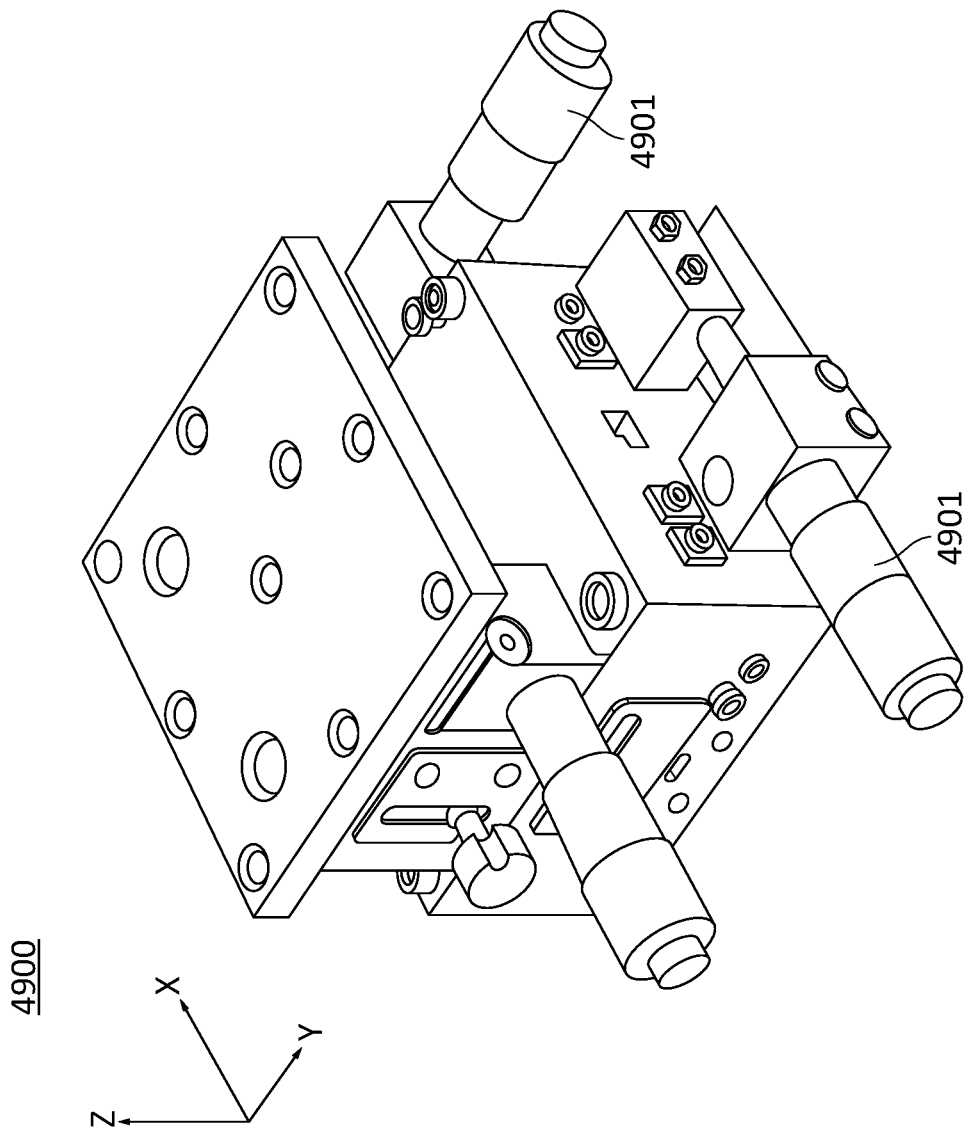

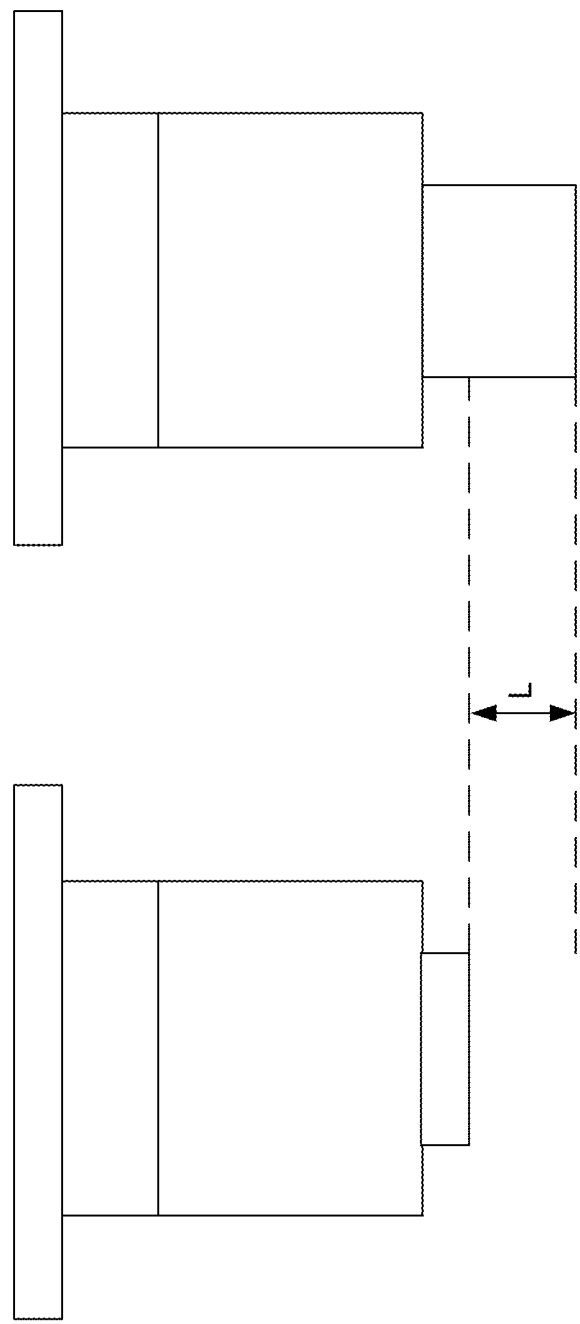

ANALYSIS ACCURACY IMPROVEMENT IN AUTOMATED TESTING APPARATUS

This application is a continuation-in-part of U.S. application Ser. No. 16/101,336, filed Aug. 10, 2018, now U.S. Pat. No. 10,324,022, which is a continuation-in-part of U.S. application Ser. No. 15/966,479, filed Apr. 30, 2018, now U.S. Pat. No. 10,281,386, which is a continuation-in-part of U.S. application Ser. No. 15/603,783, filed May 24, 2017, now U.S. Pat. No. 9,959,621, which is a continuation-in-part of U.S. application Ser. No. 15/345,061, filed Nov. 7, 2016, now U.S. Pat. No. 9,958,665, which is a continuation-in-part of U.S. application Ser. No. 15/152,470, filed May 11, 2016, now U.S. Pat. No. 9,958,658; the contents of all applications are incorporated herein by reference in their entireties.

FIELD OF THE INVENTION

The invention relates to equipment for testing biological specimen, and relates particularly to testing equipment with a magnifying function or an analyte quantification function.

BACKGROUND OF THE INVENTION

Currently, testing of liquid contents, are typically consigned to professional testing authorities for performing testing using expensive microscope equipment with high magnification ratios. Since an individual does not have microscope equipment, the testing activity cannot be performed by the individual.

However, in some testing categories nowadays testing is required to be performed on a regular basis; therefore, the need for frequent testing poses an excessive burden in terms of time and expense. For example, the category of long term testing includes semen testing for patients with infertility issues. The semen testing is mainly directed to performing observations on the number of sperms, their motility and morphology.

The semen testing method involves resting semen of a male subject at a room temperature for a period of time, and taking a drop of the sample and instilling the sample to a slide, and observing the sample under a microscope. The observations not only include performing high magnification observation of individual sperm to identify the external appearance of individual sperm, but also include performing observations of overall sperms in a large quantity, their motility, morphology and the quantity per unit area. However, an individual cannot perform the semen testing by himself because the industry has not yet developed a technology that allows an individual to perform testing through a simple aiding device.

SUMMARY OF THE INVENTION

Disclosed herein includes methods, devices, and systems for testing a biological specimen. In one example aspect, an apparatus for testing a biological specimen is disclosed. The apparatus includes a receiving mechanism to receive a carrier, which includes a holding area configured to carry the biological specimen. The device includes a camera module arranged to capture imagery of the holding area and a processor that is configured to utilize the camera module to identify, from the captured imagery of the holding area, a visual cue on the carrier, and perform, based on a result of said identification of the visual cue, a set of analytic processes on the captured imagery. The identification of the visual cue further includes verifying, based on a manner of how the visual cue is displayed in the captured imagery, whether the holding area carries the biological specimen, and selectively causing the processor to perform the set of analytic processes on the captured imagery depending on a result of said verifying.

In another example aspect, an apparatus for testing a biological specimen includes a receiving mechanism to receive a carrier, which includes a holding area configured to carry or to be exposed to the biological specimen. The apparatus includes a camera module arranged to capture a plurality of images of the holding area and a processor that is configured to utilize the camera module to adaptively select, based on the plurality of images of the holding area, an analytical algorithm suitable for a motion property of the biological specimen being tested and perform a set of analytic processes that corresponds to the selected analytic algorithm on the captured plurality of images to generate an analytic result associated with the biological specimen.

In another example aspect, an apparatus for testing a biological specimen includes a receiving mechanism to receive a carrier, which includes a holding area configured to carry or to be exposed to the biological specimen. The apparatus includes a camera arranged to capture a plurality of images, including a first image and a second image, of the holding area. The apparatus also includes a positioning mechanism operable to adjust a relative location of the carrier to the camera and a processor that is configured to utilize the camera module to identify an edge of the first image, cause the positioning mechanism to adjust the relative location of the carrier to the camera in a manner such that, when the camera takes the second image, an edge of the second image aligns with the identified edge of the first image, and perform a set of analytic processes on a combined image from the first and second images to determine one or more properties of the biological specimen.

In yet another example aspect, an apparatus for testing a biological specimen includes a receiving mechanism to receive a carrier, which a holding area that carries or has been exposed to the biological specimen. The apparatus includes a camera module arranged to capture imagery of the holding area. The camera module further includes an focusing motor operable to adjust a focal point of the camera. The apparatus also includes a processor that is configured to utilize the camera module to determine, based on operations of the focusing motor, a volumetric property of the holding area, and perform a set of analytic processes on at least a portion of the captured imagery of the holding area to determine one or more properties of the biological specimen, wherein the one or more properties of the biological specimen receives adjustment by the processor based on the determined volumetric property of the holding area.

These and other features of the disclosed technology are described in the present document.

BRIEF DESCRIPTION OF THE DRAWINGS

FIG. 35 is an example image illustrating a portion of candidate segment selection process.

FIG. 41 is an example image of a test carrier carrying a test sample that can be used to calibrate or validate a test equipment disclosed here.

FIGS. 42A and 42B illustrate different image quality in different segments of the captured image in FIG. 41.

FIG. 49 shows an example multi-axis mobile platform.

FIG. 51A shows an example of an adjustable lens of the camera module at a default position.

FIG. 51B shows the camera module in FIG. 51A with the lens at an extended position.

DESCRIPTION OF THE EMBODIMENTS

Figure 1A:
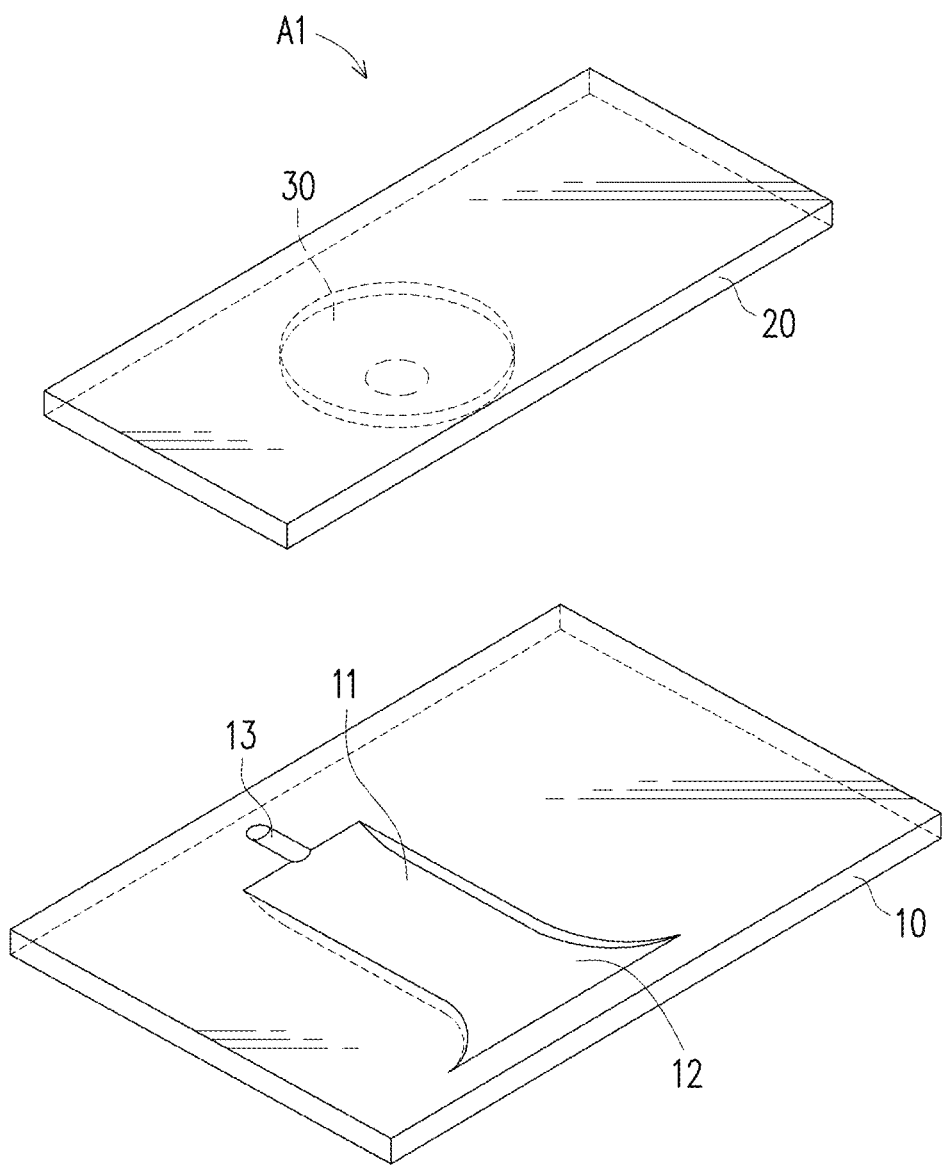
FIG. 1A is an exploded view of a testing equipment with magnifying function according to an embodiment of the invention.
Figure 1B:
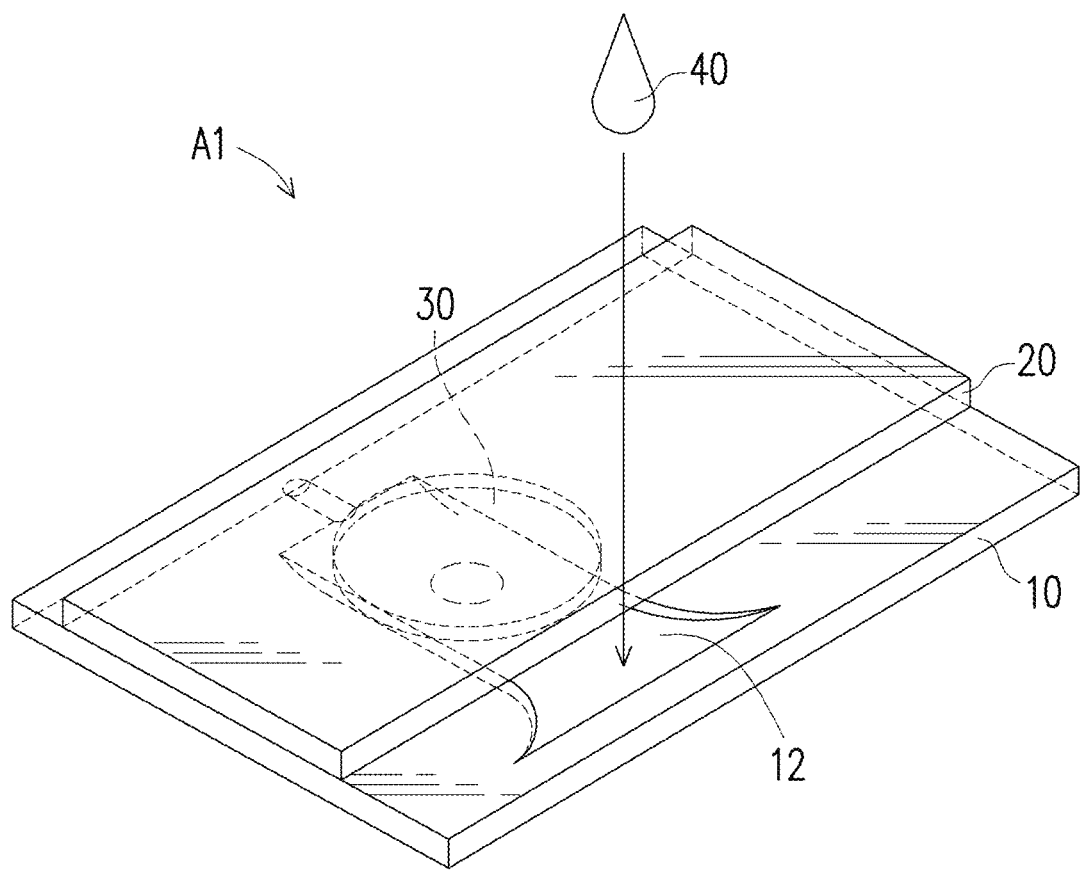
FIG. 1B is an assembled view of the testing equipment of FIG. 1A.

FIGS. 1A and 1B illustrate a testing equipment with magnifying function according to an embodiment of the invention. Embodiments disclosed herein are used for illustration purpose and should not be construed as required limitation to the invention. The testing equipment with magnifying function A1 includes: a carrier 10 having a specimen holding area 11 formed on top of the carrier 10, a cover 20 stacked on top of the carrier 10, and at least one magnifying part 30 (also referred to as magnifying component or magnifier) including a convex lens type surface formed on the cover 20.

The magnifying part 30 of the present embodiment includes a planar convex lens as illustrated in FIG. 1A. However, other type of magnifying lens, e.g., a dual-sided lenticular lens can be included as the magnifying part 30. The magnifying part 30 is disposed to be aligned with and to cover the specimen holding area 11 of the carrier 10. The magnifying part 30 may have various magnification ratios based on testing requirements of various tests. For example, the tests can include semen test, urine test, synovial joint fluid test, dermatological test, water test, or other body fluid tests, etc.

A test using the testing equipment A1 with magnifying function of the present embodiment does not require additional magnifying lens or laboratory microscopes, which are expensive and time-consuming to operate. Furthermore, there is no needed to align the specimen holding area with the magnifying lens or laboratory microscopes.

As illustrated in FIG. 1A, the specimen holding area 11 of the carrier 10 may be formed with a dented configuration. The dented configuration design provides a stable and large storage space containing a specimen 40. The dented configuration allows the specimen to rest for a required period of time before performing the testing. For example, before performing a motility testing on a semen specimen, it is necessary to rest the semen specimen in a room temperature for a required period of time before performing the motility testing.

The specimen 40 can be first instilled in the dented configuration, i.e., the specimen holding area 11 of the carrier 10 to rest for a period of time. As shown in FIG. 1B, a total area of the cover 20 can be smaller than a total area of the carrier 10. A specimen receiving port 12 exposed outside the cover 20 is formed on one side of the specimen holding area 11. The specimen receiving port 12 can be designed to have a shape expanding outwards, which can help smoothly instilling the specimen.

Figure 2A:
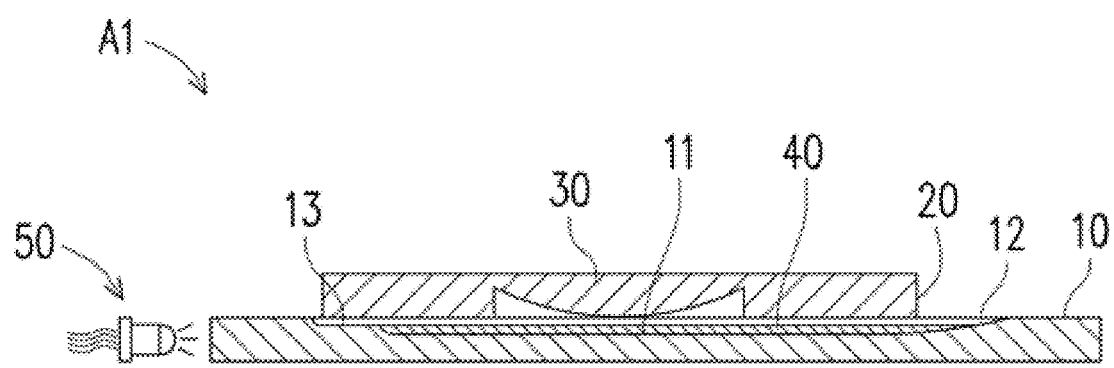
FIG. 2A is a cross-sectional view of the testing equipment of FIG. 1A.

FIG. 2A shows an air channel 13 that extends beyond the other side of the cover 20 and is formed on the other side of the specimen holding area 11. The air channel 13 may prevent air filling the inside of the specimen holding area 11, which prevent receiving of the specimen when the specimen is in a liquid status.

As shown in FIG. 2A, a lateral illumination device 50 can be disposed at one side of the carrier 20 of testing equipment A1. The lateral illumination device 50 can provide illumination for the specimen 40 in the specimen holding area 11 and therefore improve resolution of the captured testing images of the specimen 40. In some embodiments, the specimen holding area 11 can receive illustration from light source(s) on the top of or at the bottom of the testing equipment A1.

Figure 2B:
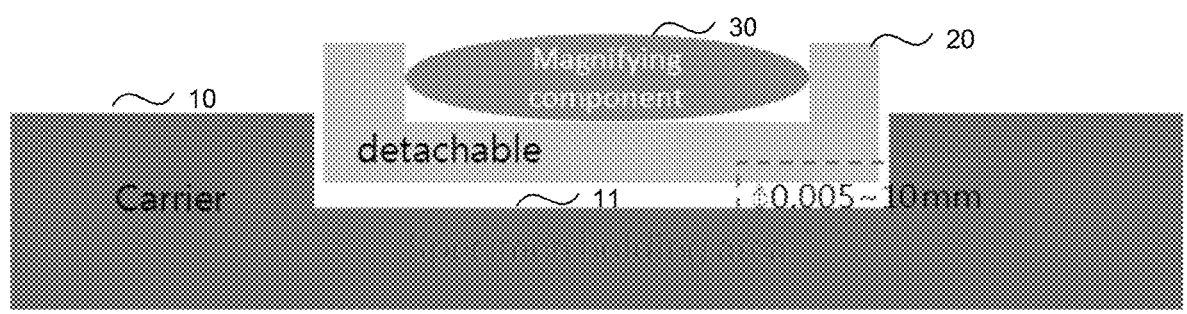
FIG. 2B is a cross-sectional view of another embodiment of testing equipment.

As illustrated in FIG. 1A, the magnifying part 30 and the cover 20 may be integrally formed, i.e., the magnifying part 30 and the cover 20 can be a single component. In other embodiments such as the embodiment illustrated in FIG. 2B, the detachable cover 20 and the magnifying component 30, which is disposed in the recess 21 of detachable cover 20, can each be separate components that are adapted to be integrated together. In other words, the same type of detachable cover 20 can be integrated with different magnifying components 30 of various magnification ratios.

In some embodiments, the distance between the bottom of the detachable cover 20 and the specimen holding area 11 is from 0.005 mm to 10 mm. In some embodiments, the distance between the bottom of the detachable cover 20 and the specimen holding area 11 is about 0.01 mm. The testing equipment can include one or more spacers (not shown) to ensure the distance between the bottom of the detachable cover 20 and the specimen holding area 11. The spacer(s) can integrally formed with the detachable cover 20 or the specimen holding area 11 of the carrier 10.

In some embodiments, the strip including the carrier 10 and the cover 20 is for sperm test. In some embodiments, the optimal angular magnification ratio for determining sperm concentration and motility is about 100 to 200. In some embodiments, the optimal angular magnification ratio for determining sperm morphology is about 200 to 300. The thinner the magnifying component, the higher the angular magnification ratio.

The focal length of the magnifying component can also relate to the angular magnification ratio. In some embodiments, a magnifying component with an angular magnification ratio of 100 has a focal length of 2.19 mm. A magnifying component with an angular magnification ratio of 156 has a focal length of 1.61 mm. A magnifying component with an angular magnification ratio of 300 has a focal length of 0.73 mm. In some embodiments, the magnifying component has an angular magnification ratio of at least 30, preferably at least 50. In some embodiments, the focal length of the magnifying component is from 0.1 mm to 3 mm.

Figure 3:
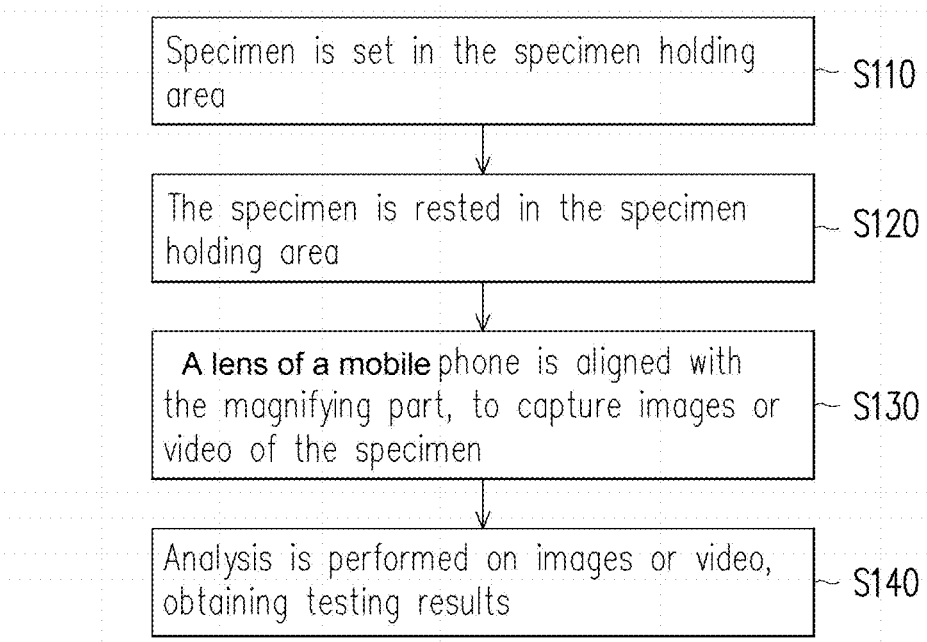
FIG. 3 is a flow diagram of testing for a testing equipment according to an embodiment of the invention.

FIG. 3 illustrates a sample process for performing testing using the testing equipment A1 with magnifying function illustrated in FIG. 1B. At step S110, the specimen 40 to be tested is set in the specimen holding area 11. At step S110, the cover 20 is stacked on top the carrier 10, before setting the specimen 40 to be tested in the specimen holding area 11 from the specimen receiving port 12. Alternatively, the specimen 40 to be tested can be set in the specimen holding area 11 directly first, before the cover 20 is stacked on top the carrier 10. At step S120, the specimen 40 is rested in the specimen holding area 11 selectively for a period of time according to testing requirements of the specimen 40. At step S130, an intelligent communication device (e.g., a mobile phone) is attached on the cover 20, and the camera of the mobile phone is aligned with the magnifying part 30, to use the camera of the mobile phone to capture a picture or video of the specimen through the magnifying part 30. At step S140, an application (APP) running at the mobile phone or other analysis device may be used to perform analysis of the picture or video, for obtain testing results.

Figure 4:
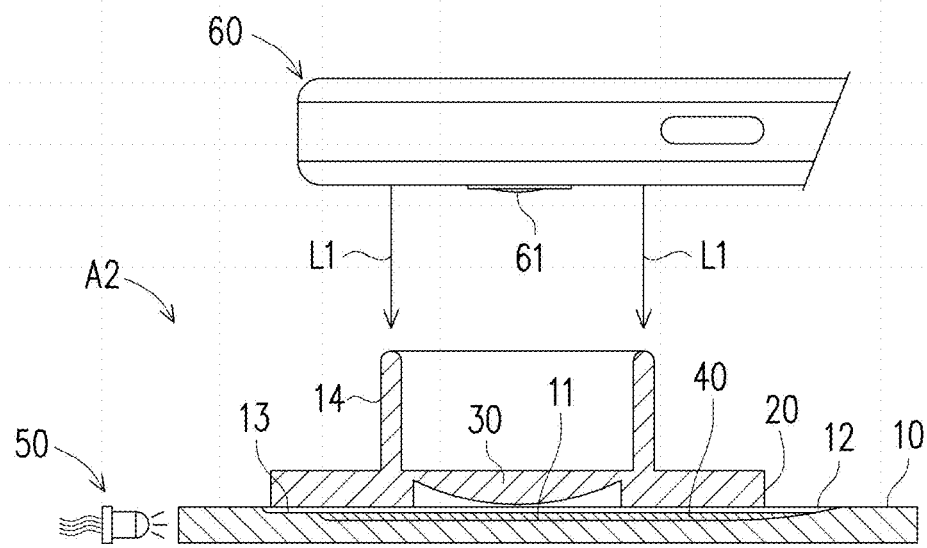
FIG. 4 is a cross-sectional view of a testing equipment with magnifying function according to another embodiment of the invention.

As illustrated in FIG. 4, a supporting side (such as a protruding part) 14 may further be formed on a top of the cover 20 of a testing equipment A2 at a border of the magnifying part 30. In some embodiments, the protruding type support structure may be formed on top of the cover 20 by the addition of the protruding part 14. When the user attempts to use an intelligent communications device 60 (e.g., a mobile device such as a smart phone or tablet) to capture the image or video of the specimen, a side of the intelligent communications device 60 having a camera 61 may be secured to the protruding part 14 (along the direction shown by the arrow L1). Thus, the testing equipment A2 allows the user to use the intelligent communications device 60 for capturing the image or video of the specimen, and does not require an expensive testing apparatus for recording the image or video. Furthermore, the height of the protruding part 14 can be pre-determined for a best observation distance based on specification of the camera 61 and the testing equipment A2.

Figure 5:
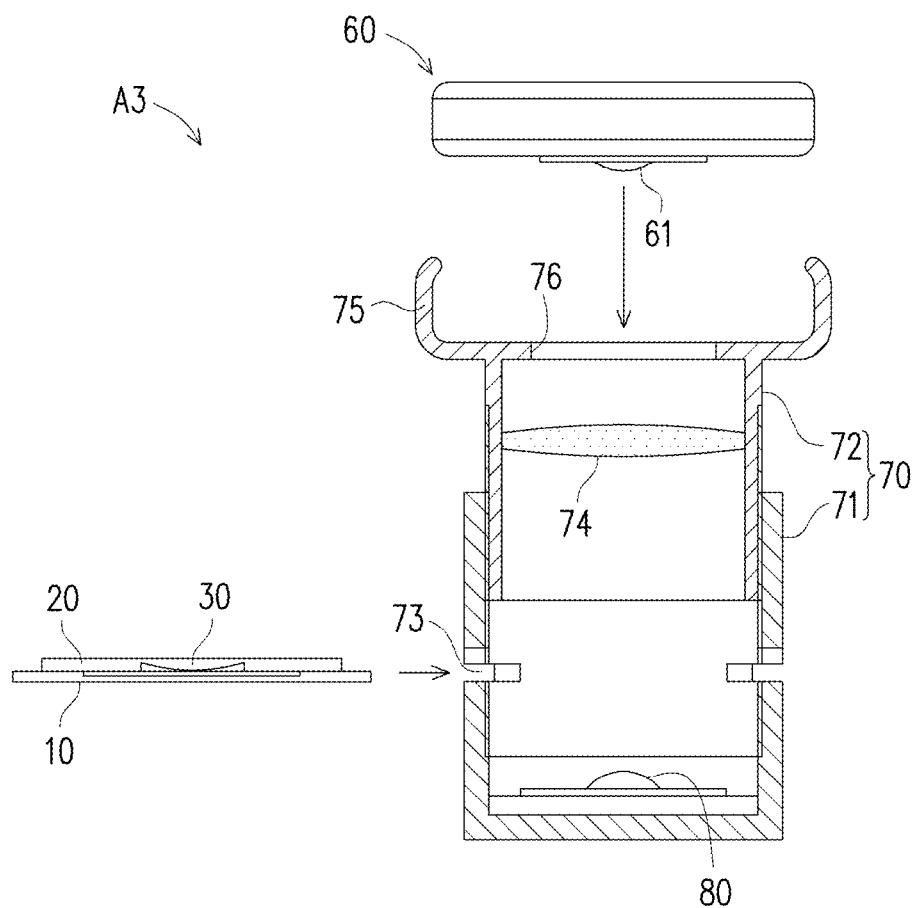
FIG. 5 is a cross-sectional view of a testing equipment with magnifying function according to another embodiment of the invention.
Figure 6:
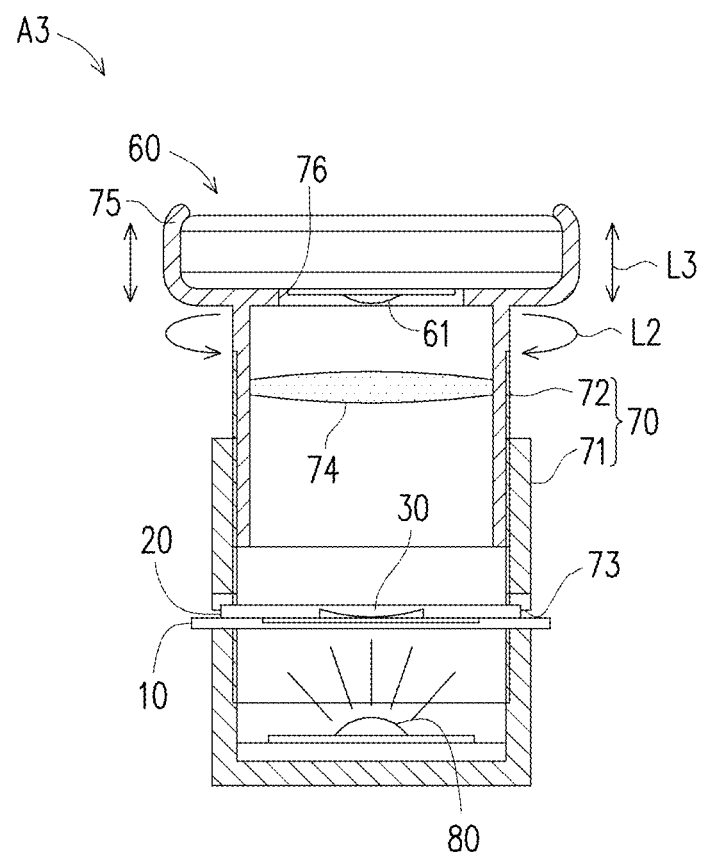
FIG. 6 is a schematic diagram of the testing equipment of FIG. 5 being used.

As shown in FIG. 5 and FIG. 6, a testing equipment A3 can include a barrel type base 70 (also referred to as base component). The barrel type base 70 includes a lower barrel base 71 and a upper barrel body 72 that can be lifted or descended with respect to the lower barrel base 71. The lower barrel base 71 has an insertion port 73 providing an insert position for the cover 20 and the carrier 10 stacked together. An upward lighting device 80 is disposed on a bottom part of the lower barrel base 71, to provide illumination to the combination of the cover 20 and carrier 10 from the bottom. The upper barrel body 72 can include, e.g., at least one additional magnification lens 74 for further magnification.

The upper barrel body 72 can be attached to the lower barrel base 71 using a screw thread mechanism such that the upper barrel body 72 that can be lifted or descended with respect to the lower barrel base 71 like a screw. In other words, the upper barrel body 72 can be rotated with respect to the lower barrel base 71 along the arrow L2 directions such that the upper barrel body 72 moves up and down along the arrow L3 directions with respect to the lower barrel base 71. By adjusting the height of the upper barrel body 72 with respect to the lower barrel body 71, the system adjusts the height of the magnification lens 74 (then changing the magnification ratio) and the height of the camera 61.

An assembling frame 75 (also referred to as form-fitting frame) may be disposed at an upper end of the upper barrel body 72. The assembling frame 75 secures the intelligent communications device 60 at a pre-determined position. The assembling frame 75 has a camera alignment hole 76. The camera 61 of the intelligent communications device 60 can receive light from the specimen through the camera alignment hole 76.

The camera 61 disposed on current intelligent communications device 60 typically only have a digital zoom function. Generally an optical zoom lens is required for testing with a high accuracy. However, the user using the testing equipment A3 does not need a camera 61 having an optical zoom lens. The high adjustment function of the testing equipment A3 provides a flexible solution for aligning the specimen, the magnifying lens, and the camera 61.

FIG. 6 shows the intelligent communications device 60 that has been assembled and secured onto the assembling frame 75, which is disposed on the upper barrel body 72. The cover 20 and the carrier 10 containing the specimen 40 are inserted through the insertion port 73. The upward lighting device 80 may provide illumination to and increase the brightness of the specimen.

The upper barrel body 72 or the barrel type base 70 can rotated along the directions L2, to adjust the height of the magnification lens 74 and the camera 61 upwards or downwards along the directions L3. The height adjustment mechanism enables a function for adjusting the magnification ratio. The camera 61 may capture dynamic videos or static testing images of the specimen 40 after magnification. Furthermore, the intelligent communications device 60 can user its originally equipped functions to store the captured videos or images, to transfer the testing images or videos, and to conduct subsequent processing.

Figure 7:
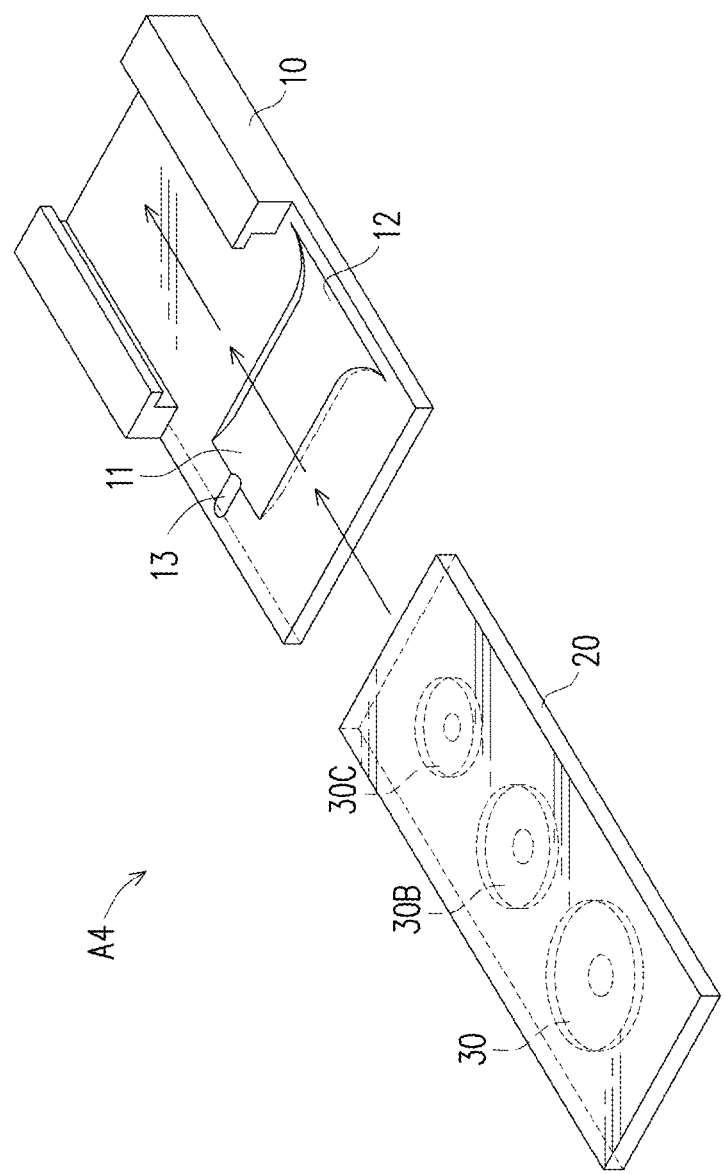
FIG. 7 is a schematic diagram of a testing equipment with magnifying function according to another embodiment of the invention.

As shown in FIG. 7, a testing equipment A4 with magnifying function includes a plurality of magnifying parts 30, 30B, 30C with different magnification ratios disposed on the cover 20. The user may shift the cover 20 to align the specimen holding area 11 of the carrier 10 with any of the magnifying parts 30, 30B, 30C with different magnification ratios, in order to obtaining testing results with different magnification ratios. By this design, the testing equipment A4 with magnifying function of a single module can be applied to satisfies magnification requirements of multiple testing protocols, without the need of changing the magnifying part or the cover.

Figure 8:
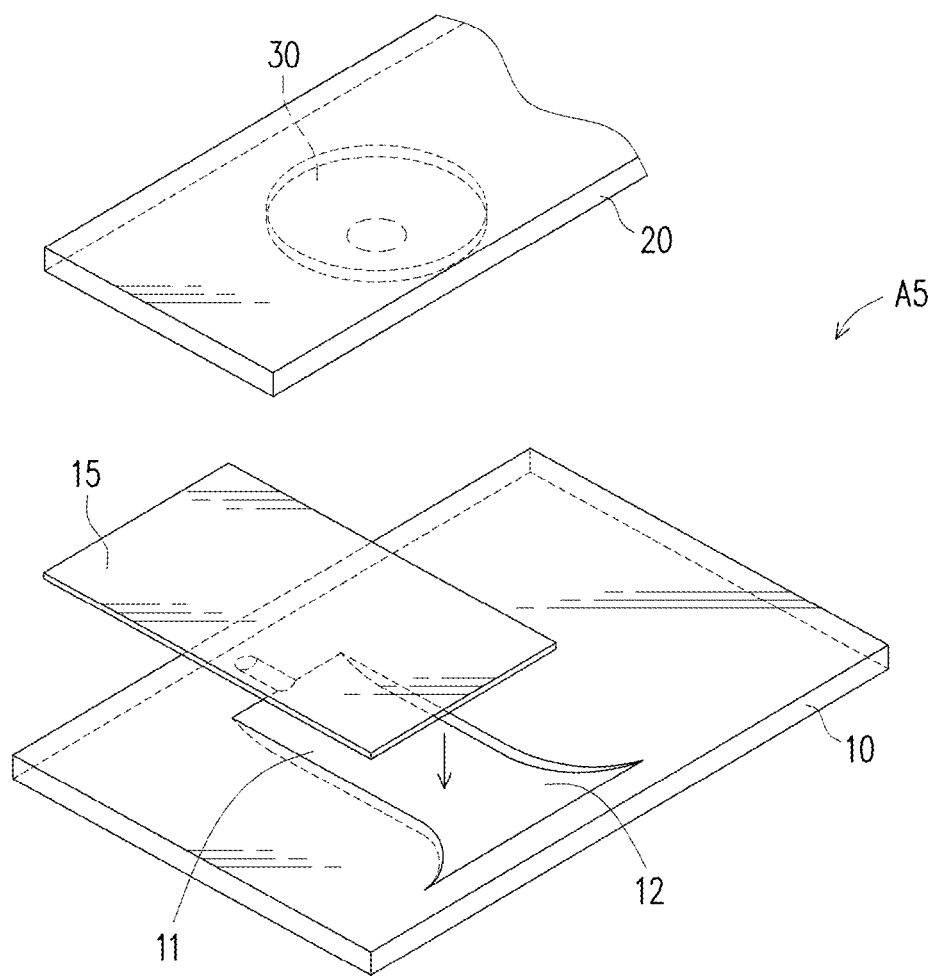
FIG. 8 is a schematic diagram of a testing equipment with magnifying function according to another embodiment of the invention.

As shown in FIG. 8, a testing equipment A5 with magnifying function includes a flexible transparent film 15. The flexible transparent film 15 is disposed between the carrier 10 and the magnifying part 30, and covers the specimen holding area 11. The flexible transparent film 15 covers the specimen 40 (in liquid state) such that the specimen 40 in a confined space. Thus, outside influences due to air, dust and dirt are confined to a minimum level. Furthermore, the testing equipment A5 may adjust the focal length by the varying the thickness of the flexible transparent film 15.

Figure 9:
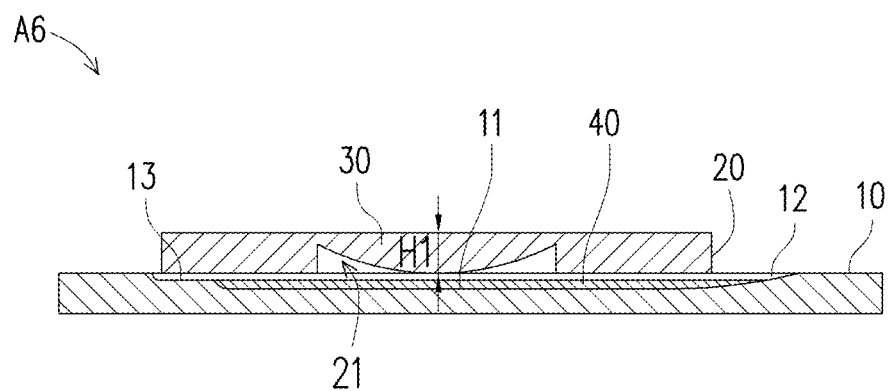
FIG. 9 is a schematic diagram of a testing equipment with magnifying function according to another embodiment of the invention.
Figure 10:
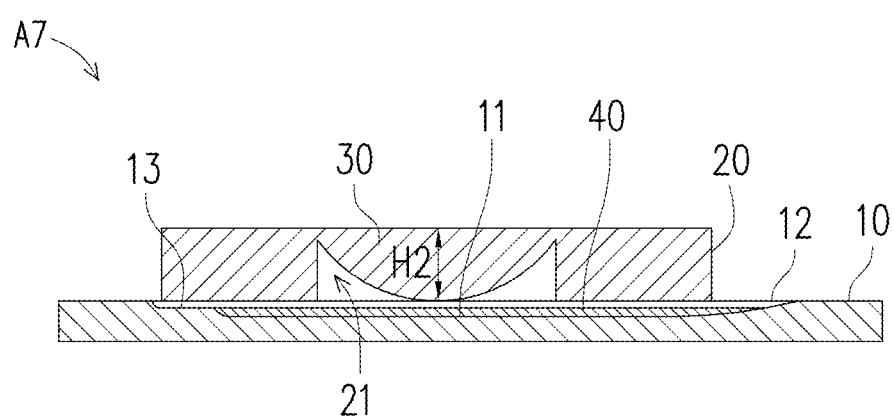
FIG. 10 is a schematic diagram of a testing equipment with magnifying function according to another embodiment of the invention.

As shown in FIG. 9, the magnifying part 30 of a testing equipment A6 with magnifying function is a planar convex lens, and a surface of the magnifying part 30 facing the carrier 10 is a protruding surface. Therefore, an upwardly concave type hollow part 21 is formed at the surface of the magnifying part 30 facing the carrier 10. A focal length parameter H1 is defined by the thickness of the thickest part of the magnifying part 30 of the planar convex lens. As shown in FIG. 10, a focal length parameter H2 of a testing equipment A7 with magnifying function is different than the focal length parameter H1 of FIG. 9.

The focal lengths H1 and H2 may be adjusted by changing thickness of the cover 20 or the size of the curvature of the magnifying part 30. For example, the focal length H2 shown in FIG. 10 is greater than the focal length H1 shown in FIG. 9, and is achieved by changing the size of the curvature of the magnifying part 30. In this way, testing requirements of various focal lengths may be satisfied by adopting different magnifying parts 30.

In some embodiments, the magnifying part 30 can be transparent and the rest of the cover 20 can be opaque. In addition, the carrier 10 may include the specimen holding area 11 which is transparent. The remaining of the carrier 10 can be opaque. When the testing operations are performed on the testing equipment, the light can propagate through the specimen holding area 11, the magnifying part 30 such that chance of light interference in other parts of the device is suppressed.

Figure 11:
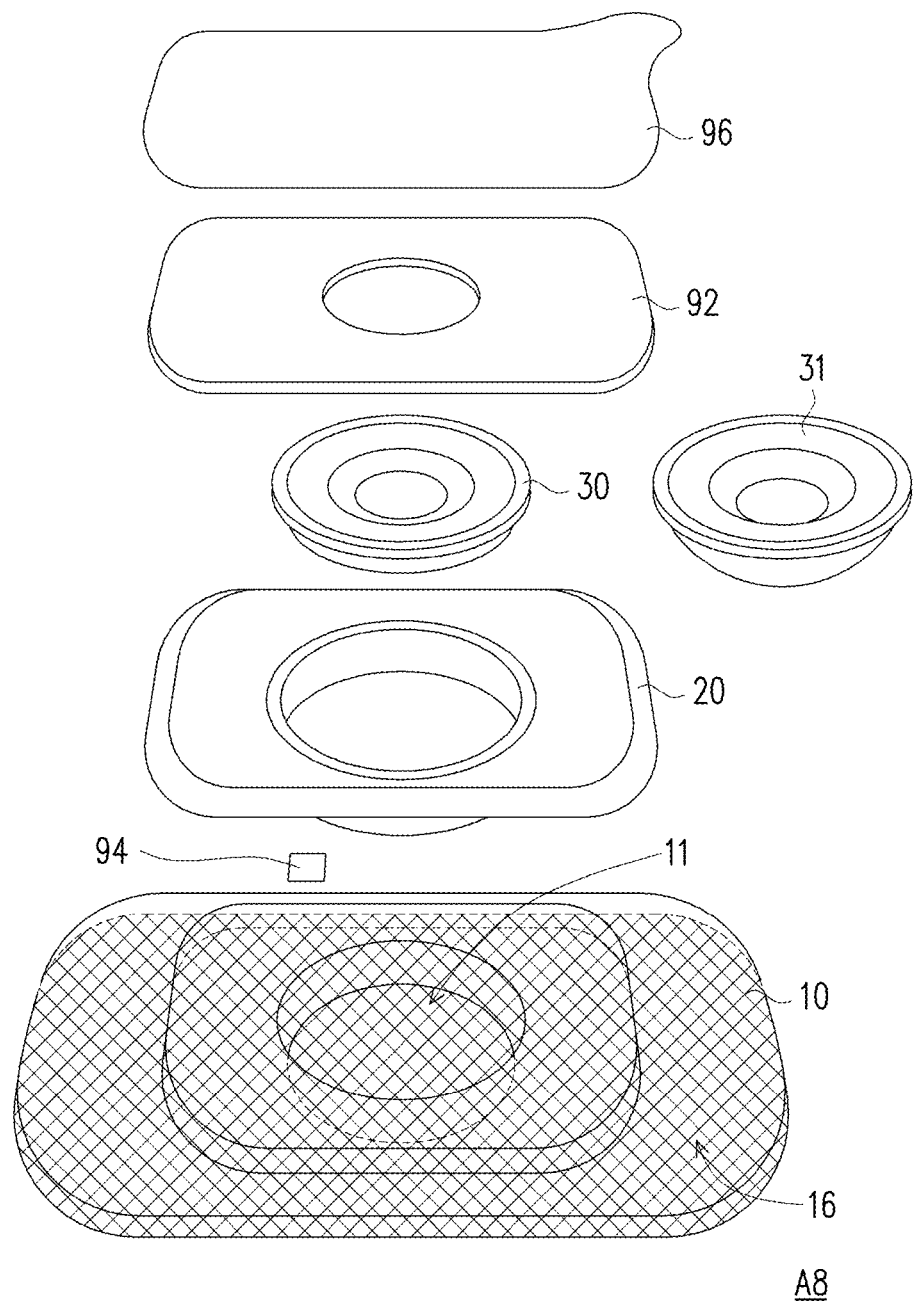
FIGS. 11-13 are views of testing equipment with magnifying function according to another three embodiments of the invention.

Referring to FIG. 11, in a testing equipment A8 with magnifying function, the carrier 10 of the testing equipment A8 further includes a light beam auxiliary guiding structure 16 formed at the bottom surface of the carrier 10. The carrier 10 can be made of transparent or translucent material. The light beam auxiliary guiding structure 16 can be opaque or include a granular structure, a rough pattern, an engraved pattern, or other suitable structure that scatters the light beam reaching the guiding structure 16. The light beam auxiliary guiding structure 16 may provide a particular pattern for the entire surface or a partial surface of the cover and the carrier. The light beam auxiliary guiding structure 16 may also be formed all around the side surfaces of the carrier 10.

When the cover 20 and the carrier 10 are stacked and are attached to the intelligent communications device 60 (as illustrated in FIG. 4 for example), the magnifying part 30 is aligned with the camera 61 of the intelligent communications device 60. In addition, a fill light (not shown) can be disposed near the camera 61 on surfaces of the intelligent communications device 60. The light beam provided by the fill light may be guided to the carrier 10 to illuminate the specimen holding area 11 through the cover 20. At the same time, the light beam auxiliary guiding structure 16 of the carrier 10 may cause the light beam provided by the fill light to scatter, further improving the brightness and illumination uniformity of the specimen holding area 11.

By disposing the light beam auxiliary guiding structure 16, the testing equipment does not require an additional fill light source to illuminate the carrier 10. Therefore, cover 20 includes a light-transmissive material so that the fill light from of the intelligent communications device 60 can reach the specimen through the cover 20. In some alternative embodiments, the device does not include a cover 20 and the fill light directly reach the carrier 10 without propagating through the cover 20.

The testing equipment A8 with magnifying function can include a non-slip film 92 and a pH test paper 94. The non-slip film 92 is attached on the supporting side (such as the top side) of the cover 20, and is used to stably dispose the cover 20 to the camera 61 of the intelligent communications device 60, as shown in FIG. 4, such that the magnifying part 30 is aligned to the camera 61 of the intelligent communications device 60. Using the non-slip film 92, the positioning of the intelligent communications device 60 relative to the testing equipment A8 is secured to a pre-determined configuration.

The non-slip film 92 can have an opening aligned to the magnifying part 30, so that the non-slip film 92 does not block the light transmitted from the specimen through the magnifying part 30 to the camera 61. The non-slip film 92 can include a material of, for example, silicon. The pH test paper 94 can be disposed on the specimen holding area 11 of the carrier 10, to provide an indication of the pH value of the specimen. The pH test paper 94 may be replaced after the usage.

In addition, the magnifying part 30 and the cover 20 can adopt a detachable design. Thus, the user may select another magnifying part 31 different from the magnifying part 30 to replace the original magnifying part 30 based on testing requirements. Various magnifying part can be assembled with the cover 20 are assembled to achieve different magnification ratios or other optical features.

Figure 12:
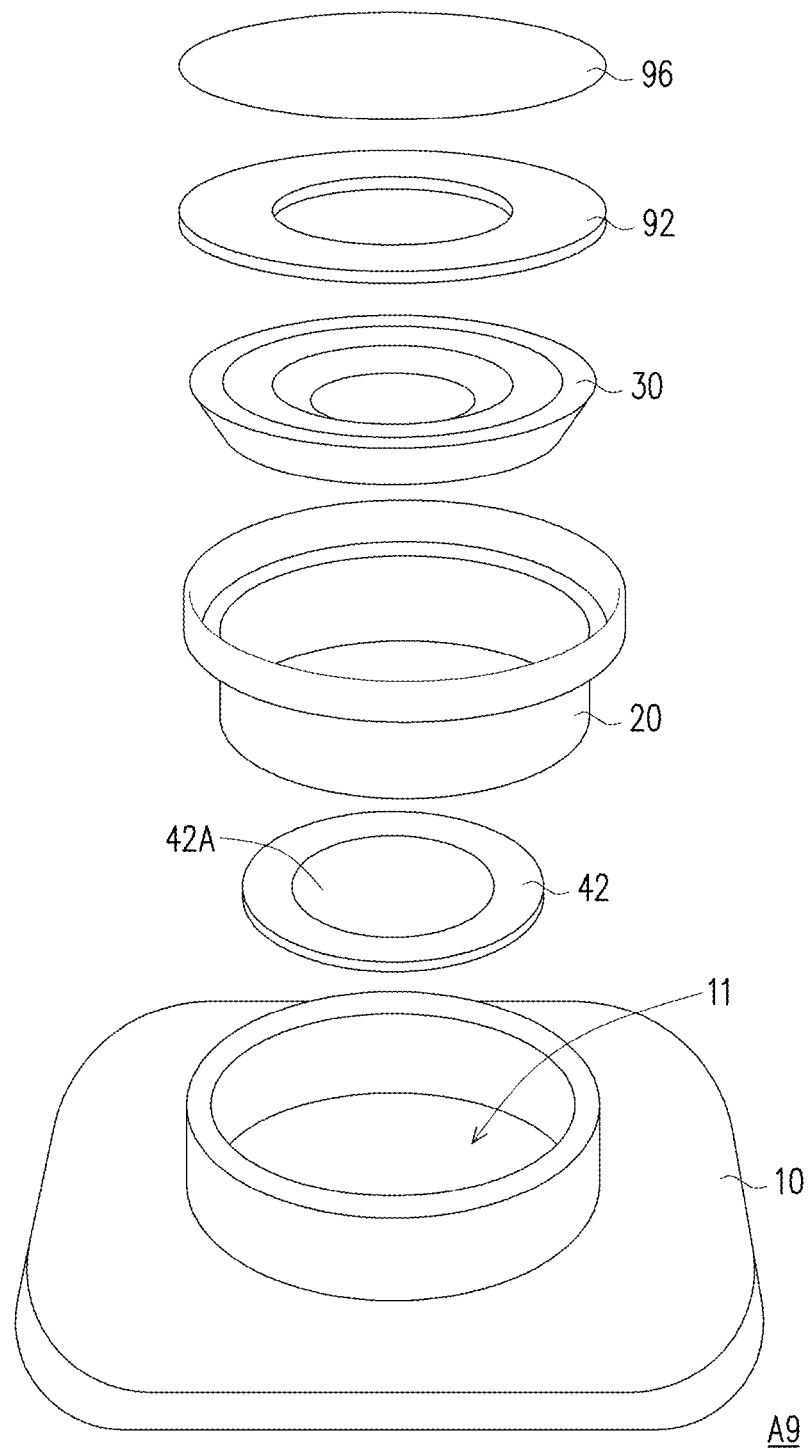

Now referring to FIG. 12, a testing equipment A9 with magnifying function can further include a specimen collection sheet 42 disposed in the specimen holding area 11. The specimen collection sheet 42, for example, has a specimen collection area 42A. The specimen collection area 42A can use adhesion or other methods to collect sperms, subcutaneous tissue/cells, parasite eggs and the like solid test bodies. In some embodiments, the specimen collection sheet 42 can serve as a spacer to maintain a distance between the cover 20 and the specimen holding area 11.

Figure 13:
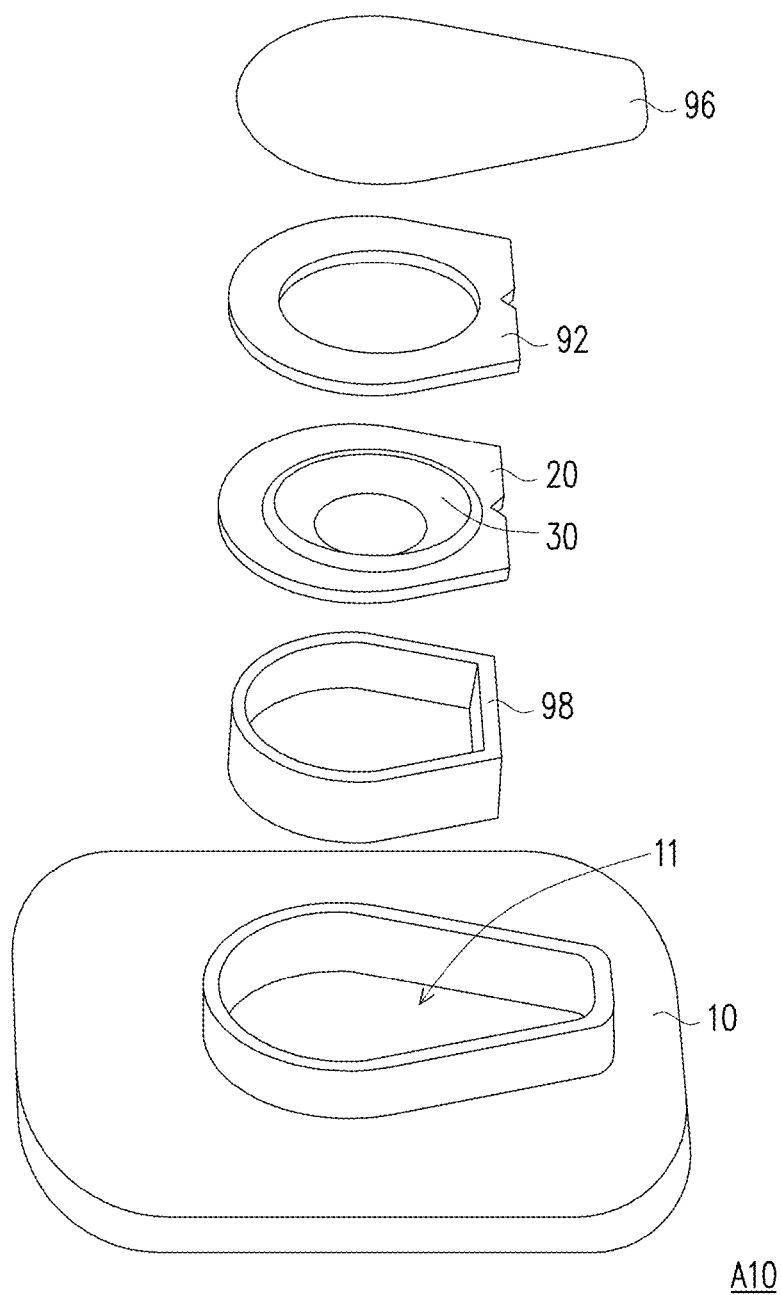

Next, referring to FIG. 13, a testing equipment A10 with magnifying function can include an isolation component 98 disposed at the specimen holding area 11 between the carrier 10 and the cover 20. The isolation component 98 can isolate the magnifying part 30 and the testing fluid in the specimen holding area 11, and prevent the testing fluid from contaminating the magnifying part 30. In some embodiments, the isolation component 98 can serve as a spacer to maintain a distance between the cover 20 and the specimen holding area 11. The isolation component 98 can be integrated with the cover 20 as a single component. Alternatively, the isolation component 98 can be integrated with the carrier 10 as a single component.

Figure 14A:
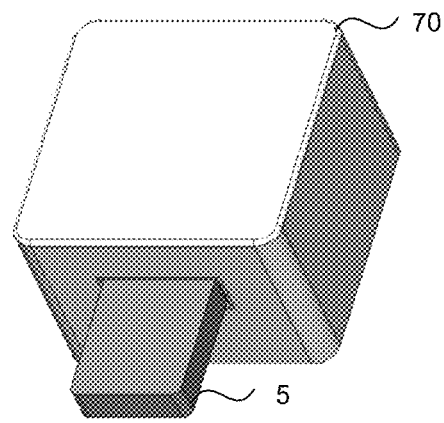
FIG. 14A is a schematic diagram of a test strip inserted into a meter device according to another embodiment of the invention.

FIG. 14A is a schematic diagram of a test strip inserted into a meter device according to another embodiment of the invention. The test strip 5 (also referred to test cartridge) includes a detachable cover 20 and a carrier 10. In other words, a combination of a detachable cover 20 and a carrier 10 (as illustrated in FIG. 1B for example) forms a test strip 5. The test strip 5 in inserted into a meter device 70 (also referred to as base component) through an insertion port. The insertion port can be, e.g., a lateral or vertical insertion port. The meter device 70 can include, e.g., components for capturing images of specimen collected in the test strip 5.

Figure 14B:
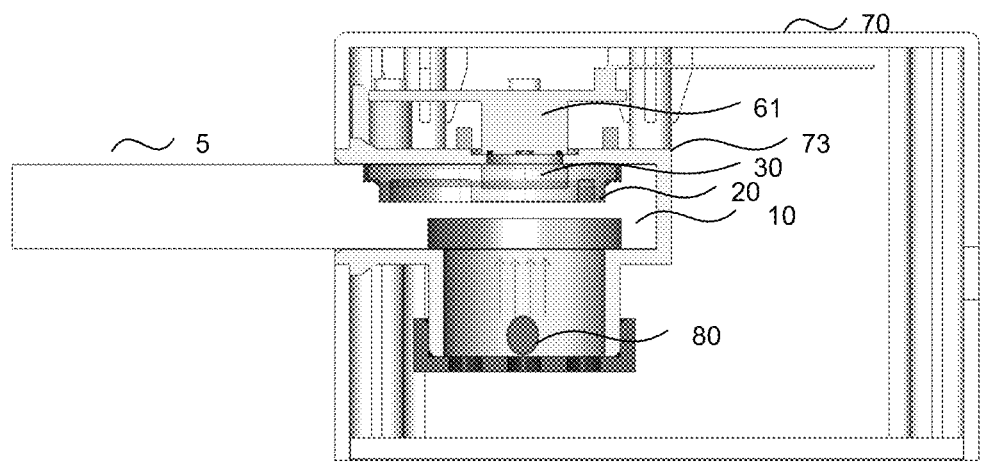
FIG. 14B is a schematic diagram of components of a meter device according to another embodiment of the invention.
Figure 15A:
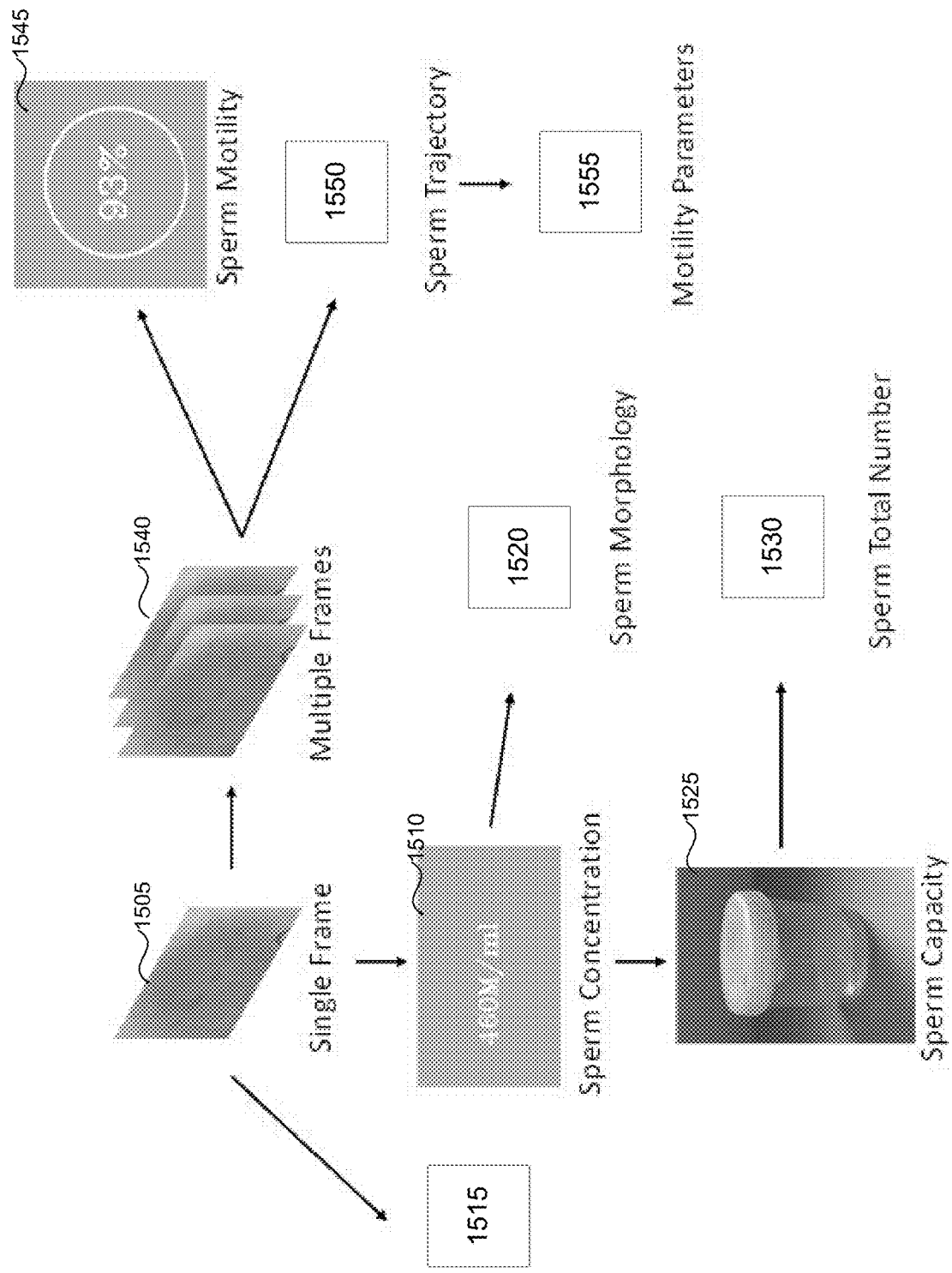
FIG. 15A illustrates a sample process of a semen test by device such as a meter device or an intelligent communications device.
Figure 15B:
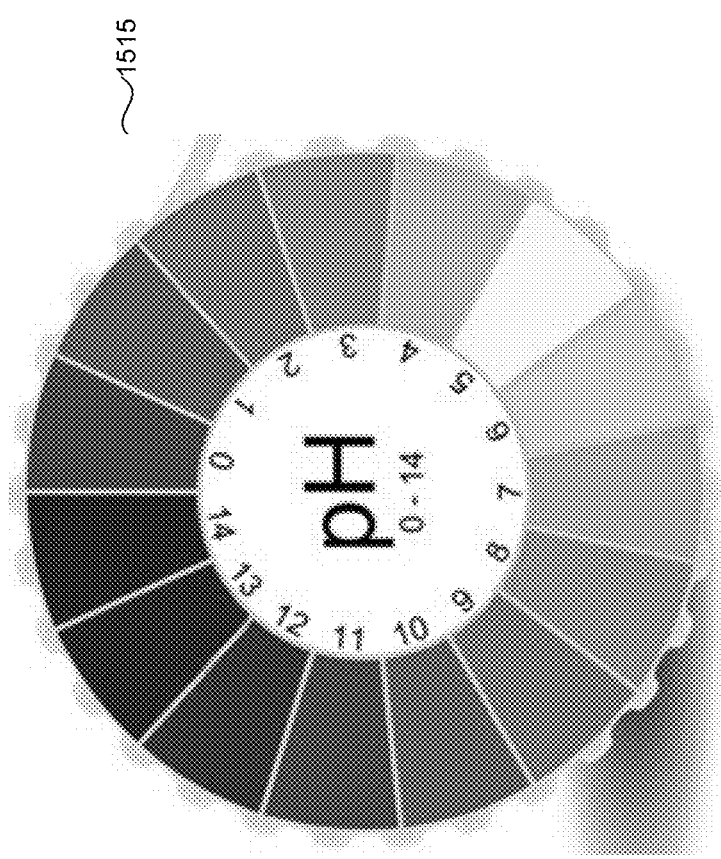
FIG. 15B illustrates a sample step 1515 of the process illustrated in FIG. 15A.
Figure 15C:
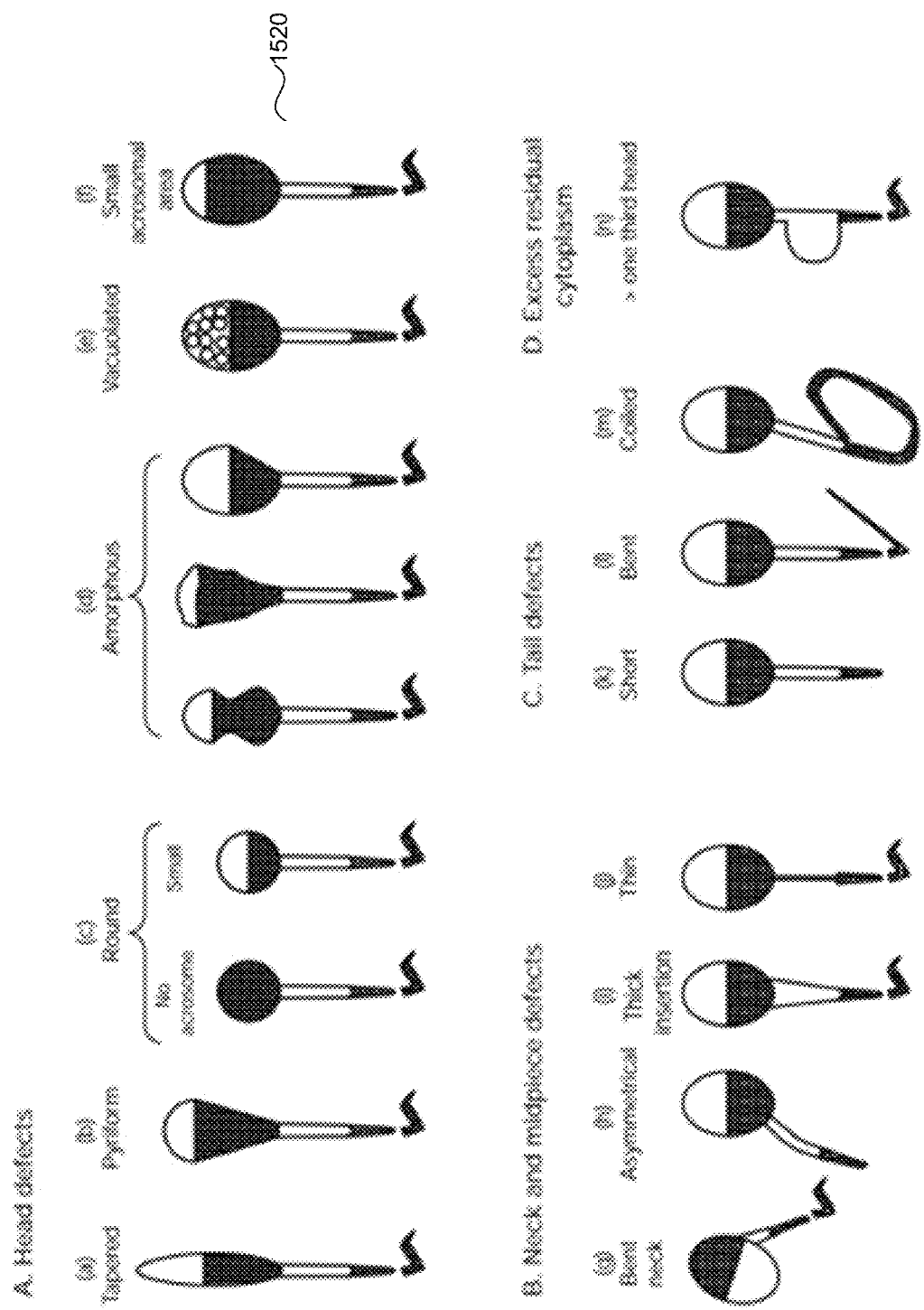
FIG. 15C illustrates a sample step 1520 of the process illustrated in FIG. 15A.
Figure 15D:
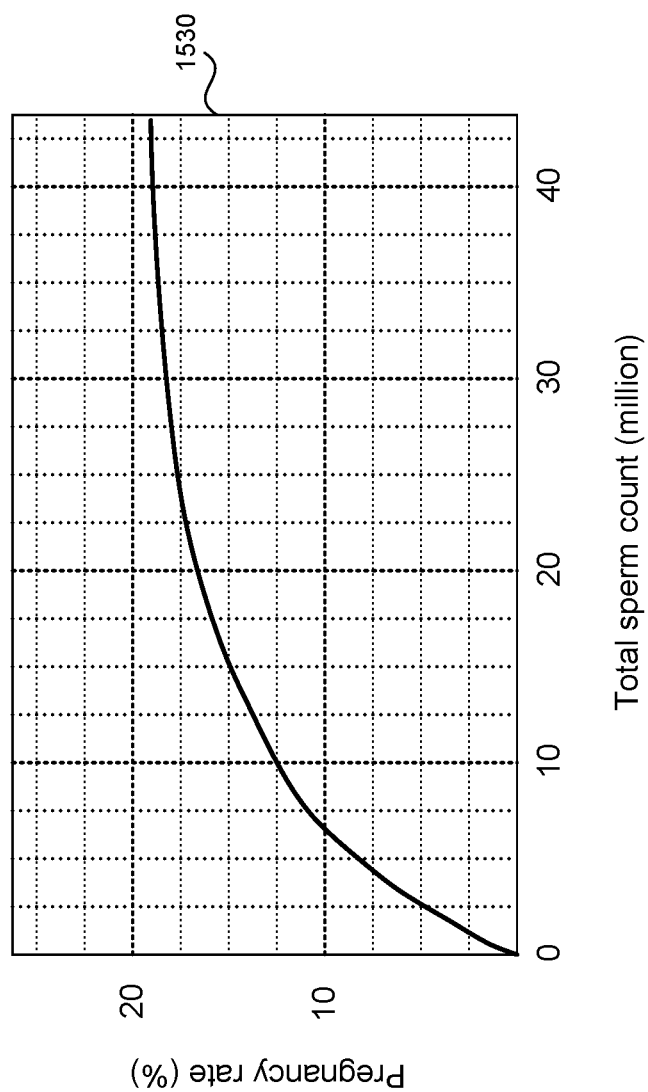
FIG. 15D illustrates a sample step 1530 of the process illustrated in FIG. 15A.
Figure 15E:
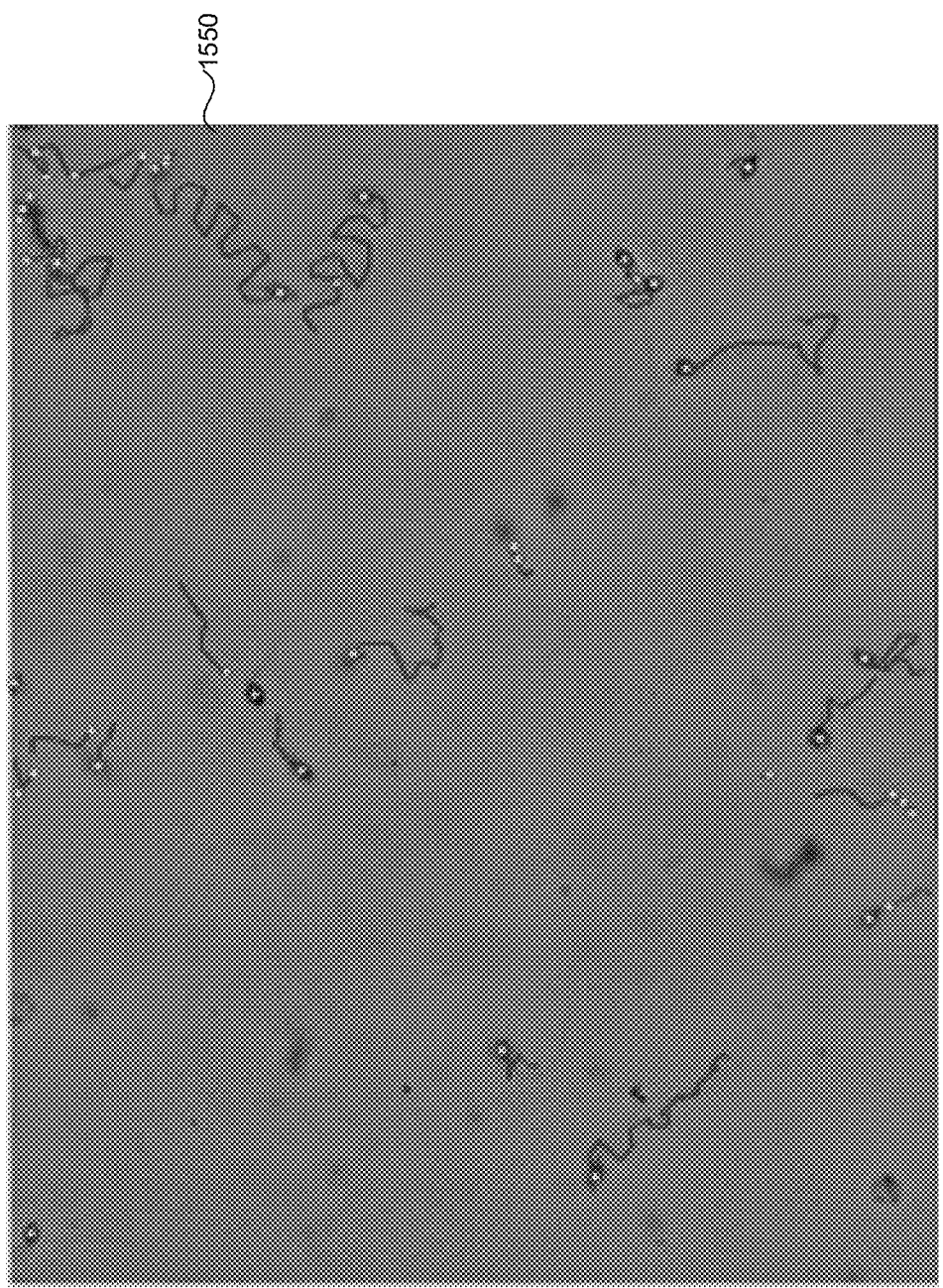
FIG. 15E illustrates a sample step 1550 of the process illustrated in FIG. 15A.
Figure 15F:
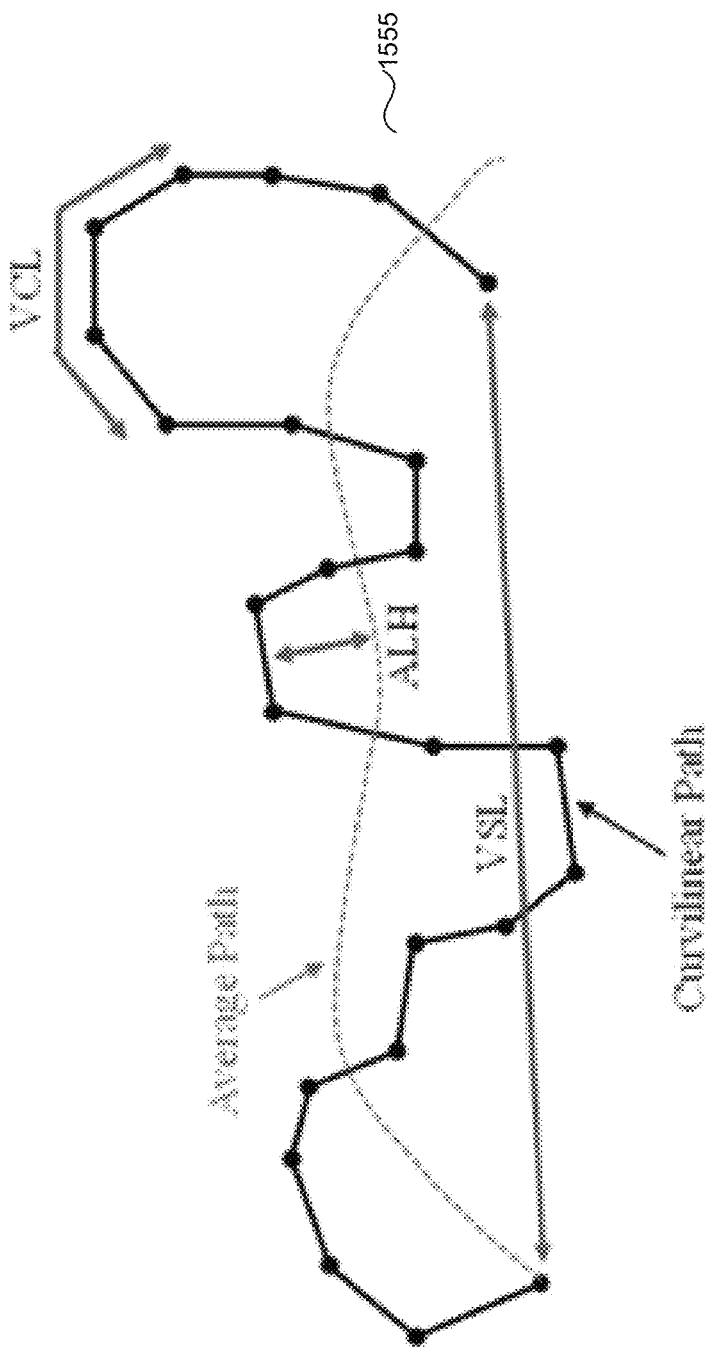
FIG. 15F illustrates a sample step 1555 of the process illustrated in FIG. 15A.

FIG. 14B is a schematic diagram of components of a meter device according to another embodiment of the invention. The meter device 70 includes an insertion port 73 providing an insert position for the strip 5. The strip 5 includes a carrier 10 and a detachable cover 20. The detachable cover includes a magnifying component 30. The meter device 70 includes a camera 61 for capturing images or videos of the specimen holding area of the carrier 10. The camera 61 is aligned with the magnifying component 30. The meter device further includes a light source 80 for provide illumination for the specimen holding area from the bottom. In some embodiments, a light collimator (e.g., a collimating lens or a light reflector; now shown) can be placed on top of the light source 80 for collimating the light beams. An annular diaphragm can be further placed between the light source 80 and the light collimator so that the light beams travelling through the light collimator form a hollow cone of light beams. The carrier 10 can include transparent or translucent materials for light prorogation.

In some embodiments, the meter device 70 can further include a phase plate for shifting phases of light rays emitted from the specimen holding area. When light rays propagate through the specimen, the speed of light rays is increased or decreased. As a result, the light rays propagating through the specimen are out of phase (by about 90 degrees) with the remaining light rays that do not propagate through the specimen. The out-of-phase light rays interfere with each other and enhance the contrast between bright portions and dark portions of the specimen image.

The phase plate can further shift the phases of the light rays propagating through the specimen by about 90 degrees, in order to further enhance the contrast due to the interference of out-of-phase light rays. As a result, the light rays propagating through the specimen are out of phase, by a total of about 180 degrees, with the remaining light rays that do not propagate through the specimen. Such a destructive interference between the light rays enhances the contrast of the specimen image, by darkening the objects in the image and lightening the borders of the objects.

In some alternative embodiments, such a phase plate can be disposed on top of the detachable cover 20 of the strip 5. In other words, the phase plate can be part of the strip 5, instead of part of the meter device 70.

FIG. 15 illustrates a sample process of a semen test by device such as the meter device 70 or the intelligent communications device 60 as illustrated in FIGS. 5 and 14 respectively. At step 1505, the device obtains an image (frame) of the specimen. At step 1510, the device determines the sperm concentration based on the image. By analyzing the color or the grayscale of the pH strip, at step 1515, the device can further determine the pH value of the specimen. For example, the device can include a processor to identify the color of a portion of an image which is captured by camera, corresponding to the pH strip and to determine a biochemical property (e.g., pH level) of a biological specimen contained in the strip. In some other embodiments, the light source of the device can provide illumination with at least one color. For example, the light source can include light emitters with different colors (e.g., red, green and blue) to form light of various colors. The camera of the device can further capture at least one (or more) image of the sample being illuminated with light The processor can compare the colors of a specific region (e.g., pH strip region) of the images to determine a property of the biological specimen or quantification of analyte. In some embodiments, the processor only needs a color of the specific region of one image to determine a property of the biological specimen. For example, the device (e.g., a testing equipment) can include a color calibration module for calibrating the color of the image. The processor then analyzes the calibrated image to determine the property of the biological specimen. Alternatively, the test strip can include a color calibration area that has a known color. The processor conducts a color calibration operation on the image based on the color calibration area, and then analyzes the calibrated image to determine the property of the biological specimen or quantification of analyte. In some embodiments, the reagent in the pH strip (or other types of biochemical test strips) reacts with the biological specimen, before the specific region (e.g., pH strip region) of the images shows specific color(s). In some embodiments, the specific region for color detection does necessarily need a magnification for the images captured by the camera. Thus, at least in some embodiments, there is no magnifying component or supplement above a specific region of the strip for color detection (e.g., pH strip region). For example, some types of biochemical test strips contain photochemical reagents. When a photochemical reagent reacts with a specific analyte in the biological specimen, the reaction causes a color change in the specimen holding area of the strip. The processor can analyze the image of the test strip (captured by the camera) to detect the color change and to quantify the specific analyte in the biological specimen. Furthermore, the device can determine the sperm morphology (1520), sperm capacity (1525) and sperm total number (1530). At step 1540, the device obtains a series of multiple frames of the specimen. At steps 1545, 1550 and 1555, the device can determine the sperm motility parameters based on the sperm trajectory and determine the sperm motility.

Figure 16:
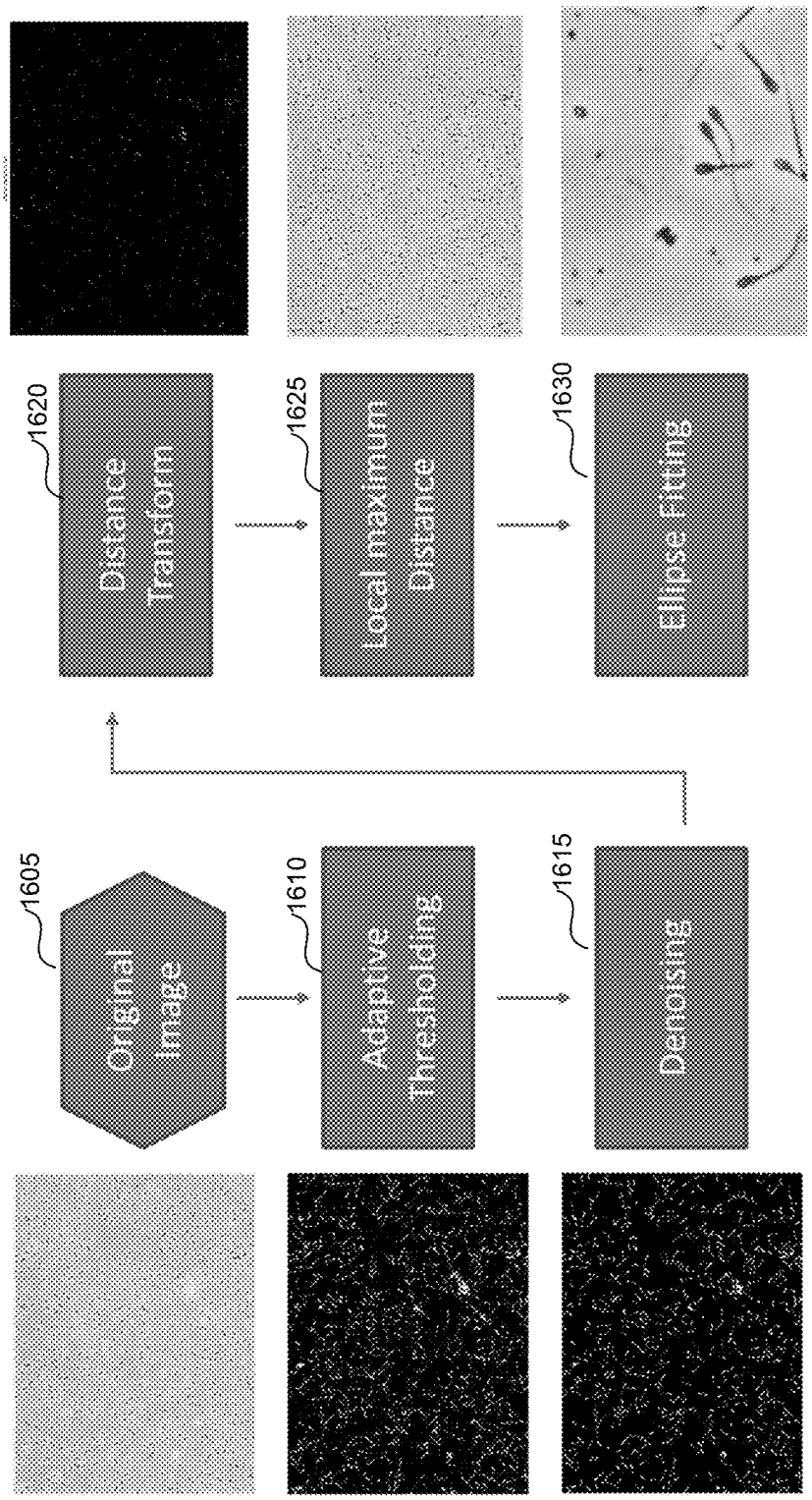
FIG. 16 illustrates a sample process of determining sperm concentration.

FIG. 16 illustrates a sample process of determining sperm concentration. At 1605, a camera of the meter device 70 or the intelligent communications device 60 ("the device"), as illustrated in FIGS. 5 and 14 respectively, captures a magnified image of the sperm specimen. The captured image is an original image for the determining the sperm concentration. The device then converts the digital color image into digital grayscale image, and further divides the digital grayscale image into multiple regions.

At step 1610, the device conducts an adaptive thresholding binarization calculation on each region, based on the mean value and standard deviation of the grayscale values of that region. The goal of the adaptive thresholding binarization calculation is to identify objects that are candidates of sperms as foreground objects, and to identify the rest of the region as background.

Foreground objects in the image after the binarization calculation may still include impurities that are not actually sperms. Those impurities are either smaller than the sperms or larger than the sperms. The method can set an upper boundary value and a lower boundary value for the sizes of the sperms. At step 1615, the device conducts a denoising operation on the image by removing impurities that are larger than the upper boundary value or smaller than the lower boundary value for the sperms. After the denoising operation, the foreground objects in the image represent sperms.

The method counts the number of sperms in the image based on the head portions of the sperms. At steps 1620 and 1625, the device conducts a distance transform operation to calculate a minimum distance between the foreground objects and the background, and also identify locations of local maximum values. Those locations are candidates of sperm head locations.

At step 1630, the device conducts an ellipse fitting operation to each sperm candidate object to reduce false positive candidates that do not have ellipse shapes and therefore are not sperm heads. Then the device counts the total number of remaining positive candidates of sperms, and calculates the concentration of the sperms based on the volume represented by the image. The volume can be, e.g., the area of the captured specimen holding area times the distance between the specimen holding area and the bottom of the cover.

In some embodiments, the device can use multiple images of the specimen and calculate concentration values based on the images respectively. Then the device calculates an average value of the concentration values to minimize the measurement error of the sperm concentration.

Figure 17:
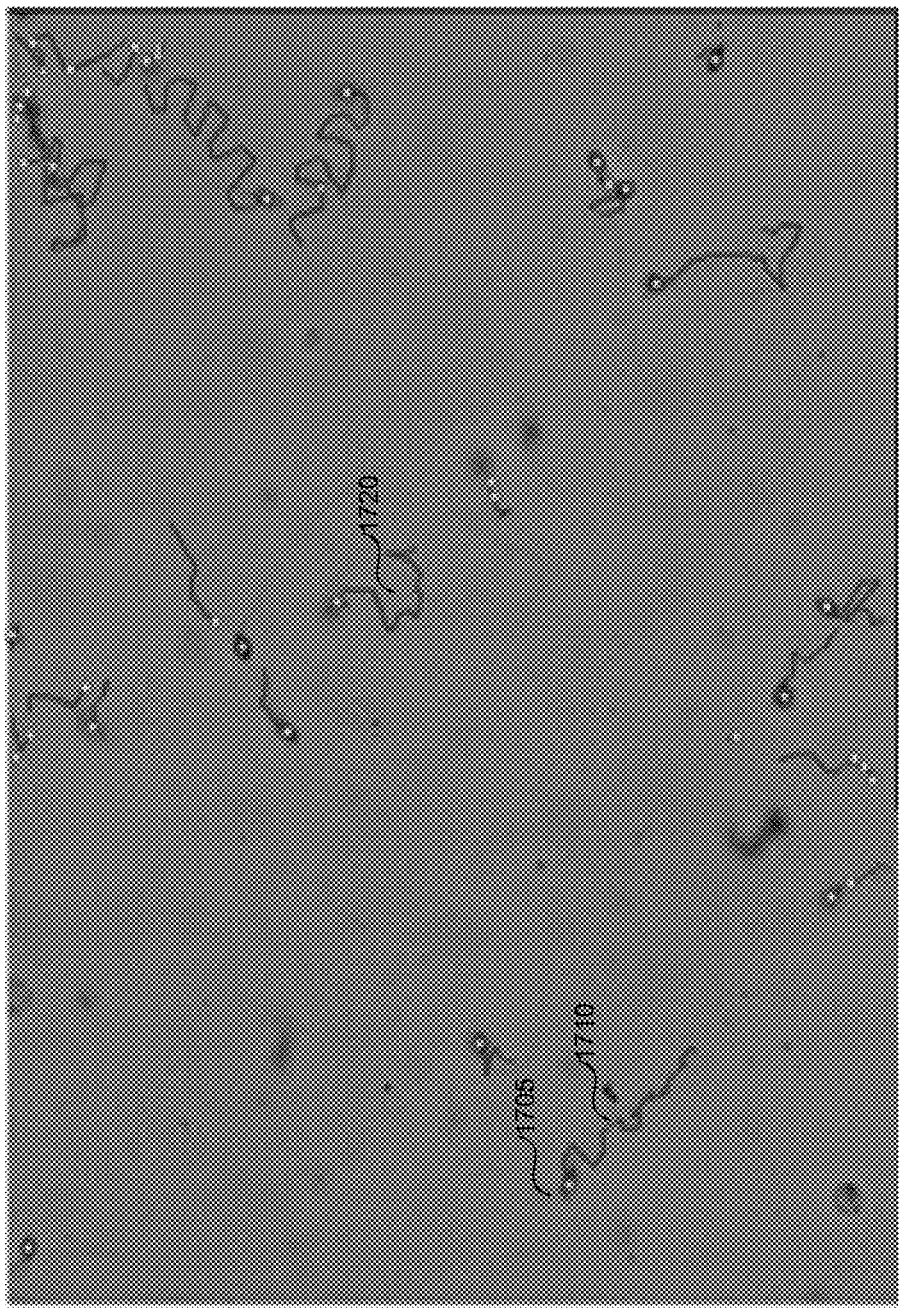
FIG. 17 illustrates sample sperms and sample sperm trajectories.

Using a series of images (e.g., video frames) of the specimen, the device can further determine the trajectories and motility of the sperms. For example, FIG. 17 illustrates sample sperms such as sperm 1705 and sample sperm trajectories such as trajectory 1710 and trajectory 1720.

Figure 18:
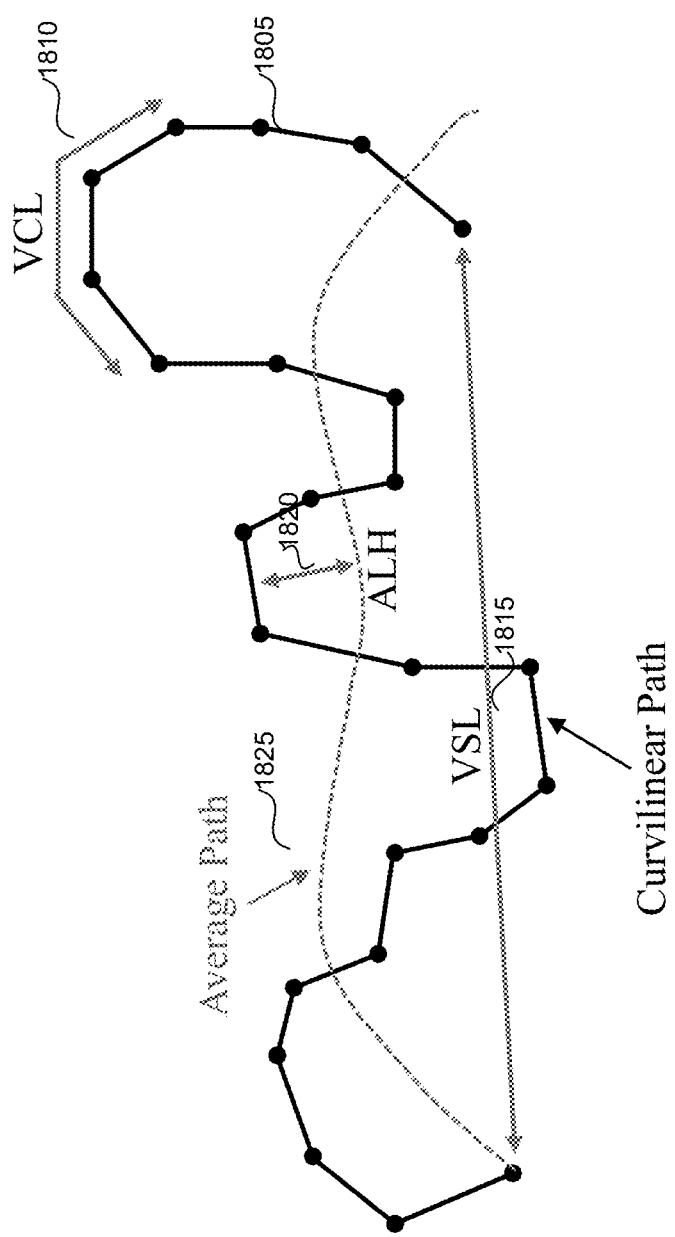
FIG. 18 illustrates a sample process of determining sperm trajectories and motility.

FIG. 18 illustrates a sample process of determining sperm trajectories and motility. A camera of the meter device 70 or the intelligent communications device 60 ("the device"), as illustrated in FIGS. 5 and 14 respectively, captures a series of images (e.g., video frames) of the sperm specimen. The device uses the captured series of images for determining parameters of sperm motility. In order to determine the parameters of sperm motility, the device needs to track the trajectory of each sperm in the series of images.

The device converts the digital color images into digital grayscale images. The device first identifies the head positions of sperms in the first image of the series (e.g., using a method illustrated in FIG. 16). The identified head positions of the sperms in the first image are the initial positions for the sperm trajectories to be tracked. In some embodiments, the device can use a two-dimensional Kalman filter to estimate the trajectory for the movement of the sperms. In some embodiments, the two-dimensional Kalman Filter for tracking sperm $s_j$ with measurement $z_j(k)$ includes steps of:
1: Calculate the predicted state $\hat{x}_{s_j}(k|k-1)$ and error covariance matrix $P_{s_j}(k|k-1)$:

$$\hat{x}_{s_j}(k|k-1)=F(k)\hat{x}_{s_j}(k-1|k-1)$$

$$P_{s_j}(k|k-1)=F(k)P_{s_j}(k-1|k-1)F(k)^T+Q(k-1)$$

2: Using the predicted state $\hat{x}_{s_j}(k|k-1)$, the measurement $z_j(k)$ and error covariance matrix $P_{s_j}(k|k-1)$, calculate the predicted measurement $\hat{z}_{s_j}(k|k-1)$, measurement residual $v_{s_j}(k)$ and residual covariance matrix $S_{s_j}(k)$:

$$\hat{z}_{s_j}(k|k-1)=H(k)\hat{x}_{s_j}(k|k-1)$$

$$v_{s_j}(k)=z_j(k)-\hat{z}_{s_j}(k|k-1)$$

$$S_{s_j}(k)=H(k)P_{s_j}(k|k-1)H(k)^T+N(k)$$

3: if $v_{s_j}(k)^T S_{s_j}(k)^{-1} v_{s_j}(k) < \gamma$ and $\|v_{s_j}(k)\|/T \le V_{max}$ then calculate the Kalman filter gain $K_{s_j}(k)$, updated state estimate $\hat{x}_{s_j}(k|k)$, and updated error covariance matrix $P_{s_j}(k|k)$:

$$K_{s_j}(k)=P_{s_j}(k|k-1)H^T(k)S_{s_j}(k)^{-1}$$

$$\hat{x}_{s_j}(k|k)=\hat{x}_{s_j}(k|k-1)+K_{s_j}(k)v_{s_j}(k)$$

$$P_{s_j}(k|k)=P_{s_j}(k|k-1)-K_{s_j}(k)H(k)P_{s_j}(k|k-1)$$

(k|k−1) denotes a prediction of image k based on image k−1, $\hat{x}_{s_j}$ is the state of position and velocity of j-th sperm. $P_{s_j}$ is the covariance matrix of the estimation error, Q(k−1) is the process noise covariance matrix, N(k) is the covariance matrix of white position noise vector, γ is the gate threshold and $V_{max}$ is the maximum possible sperm velocity.

When tracking multiple trajectories of multiple sperms, the method can use joint probabilistic data association filter to decide the trajectory paths. The joint probabilistic data association filter determines the feasible joint association events between the detection targets and measurement targets. Feasible joint association events ($A_{js}$) is the relative probability values between the detection sperm s and measurement sperm j. Then the method conducts path allocation decisions based on optimal assignment method. $A_{js}$ is defined as:

$$A_{js} = \begin{cases} -\ln(\lambda^{-1} f_{s_j}[z_j(k)]), & \text{if measurement sperm } j \text{ is validated by track } s \\ \infty, & \text{otherwise} \end{cases}$$

it measurement sperm j is validated by track s
otherwise

λ is the parameter, $f_{s_j}[z_j(k)]$ is the Gaussian probability density function of the detection sperms.

Based on the series of frames within a time period, the method identifies the trajectory of each sperm, such as the trajectory 1805 as illustrated in FIG. 18. Then the method determines various parameters of the sperm mobility based on the trajectories. The parameters include, e.g., curvilinear velocity (VCL), straight-line velocity (VSL), linearity (LIN) and amplitude of lateral head displacement (ALH). The curvilinear velocity (VCL) 1810 is defined as a summation of movement distances within a unit of time. The straight-line velocity (VSL) 1815 is defined as a straight-line movement distance within a unit of time. The linearity (LIN) is defined as VSL divided by VCL. The amplitude of lateral head displacement (ALH) 1820 is defined as twice the amplitude of the lateral displacement of the sperm head relative to the average path 1825.

In some embodiments, the curvilinear velocity (VCL) 1810 can be used to determine the sperm motility. The method can set a velocity threshold value. Any sperms having VCL higher than or equal to the velocity threshold value are identified as active sperms. The rest of the sperms, which have VCL lower than the velocity threshold value, are identified as non-active sperms. The level of motility is the number of identified active sperms divided by the total number of sperms recognized from the images.

The method can further analyze the sperm morphology. A camera of the meter device 70 or the intelligent communications device 60 ("the device") captures a magnified image of the sperm specimen. The captured image is an original image for the determining the sperm morphology.

The method detects the shapes of the sperm candidates based on segmentation. The method uses the locations of heads of the sperms as the initial points. Using a segmentation algorithm that relates to the shapes, the method divides the images of the sperms into head portions, neck portions and tail portions. For example, the method can divide the sperms using methods such as active contour model.

Based on the portions, the method calculates parameters for the various portions (such as lengths and widths). A classifier (such as support vector machine, neural network, convolutional neural network or adaboost) can be trained using training data set includes samples that are labeled already. After the training, the parameters of the various portions of the sperms can be fed to the classifier to determine whether the sperm has a proper morphology. In some embodiments, the classifier can be used for other applications such as detecting properties of cells and microbes.

Figure 46:
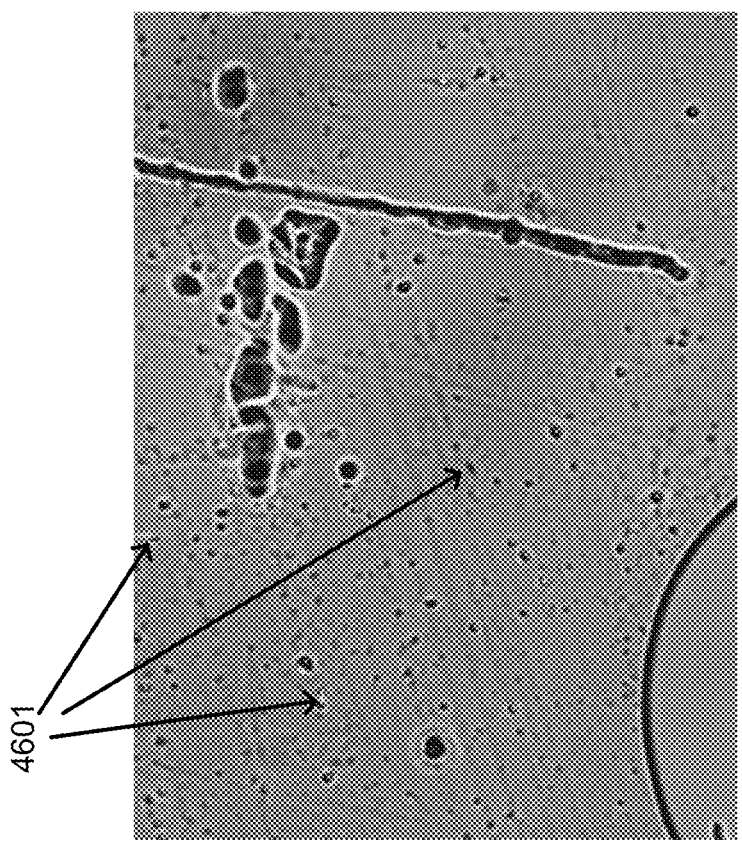
FIG. 46 illustrates an example image that includes a number of mistakenly classified areas.

Further, it is observed here that in some cases, a number of areas in the images may sometimes be mistaken as moving trajectories of the sperm due to unstable voltage, flickering light source, or other types of noises. FIG. 46 shows an example image that includes a number of mistakenly classified areas. In FIG. 46, small areas 4601 are classified as moving trajectories yet in fact they are static. To reduce the impact of external noises, the processor can adopt an analytical algorithm to determine a motion property of the specimen so that false classifications can be minimized.

Figure 47:
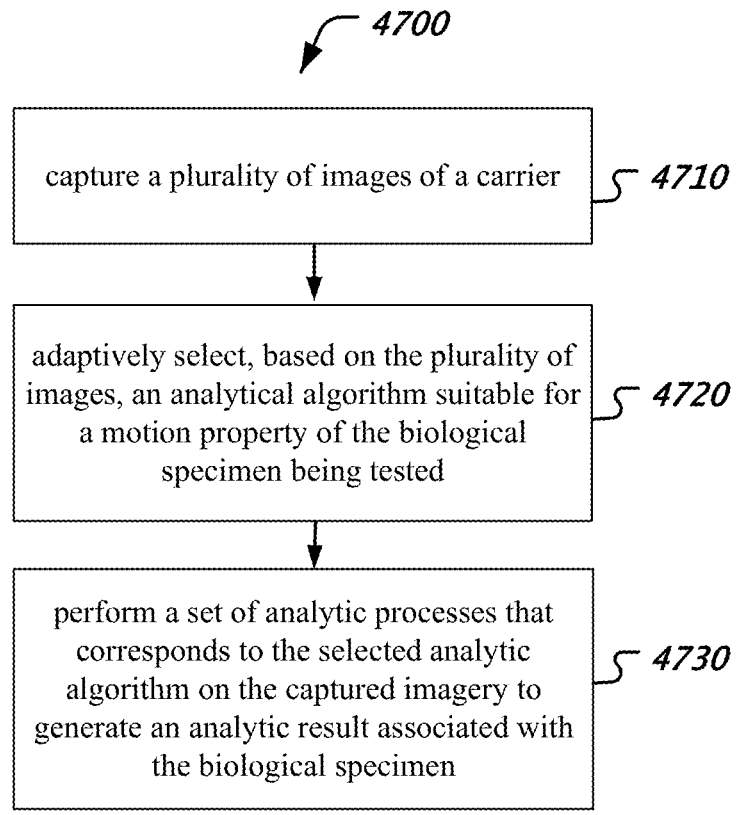
FIG. 47 is an example flow chart of a process that can be implemented by a testing equipment disclosed herein to determine a motion property of a specimen.

FIG. 47 is an example flow chart of a process 4700 that can be implemented by a test equipment disclosed herein to accurately determine a motion property of a specimen. At step 4710, e.g., after the carrier cartridge is inserted, the device(s) can use the camera module(s) to capture a plurality of images of the specimen holding area of the carrier.

At step 4720, the device can adaptively select, based on the plurality of images, an analytical algorithm suitable for a motion property of the biological specimen being tested. In some embodiments, the motion property indicates that whether the specimen is substantially static or substantially dynamic. Upon determining that the specimen is substantially static, a static algorithm can be selected to process the captured images. As an example, the static algorithm can determine morphology, such as sperm acrosome and/or the middle part of the sperm. In some embodiments, the static algorithm can also analyze Sperm Chromatin Dispersion (SCD) stained images to determine a normalcy of sperm DNA fragmentation. On the other hand, a dynamic algorithm can be selected upon determining that the specimen is substantially dynamic. As another example, the trajectories of the high-mobility sperms can be determined using the dynamic algorithm. The dynamic algorithm can help determine multiple parameters about the sperm mobility, such as VCL, VSL, VAP, ALH as shown in FIG. 15, so as to optimize the computation efficiency.

To select the analytical algorithm in step 4720, according to some embodiments, the device can first select two images among the plurality of images. The device then compares the two images and determines an amount of variation between the first image and the second image to determine which analytical algorithm is suitable to use. The amount of variation can be determined based on a rate of change in motion of a detectable target in the specimen. For example, the testing equipment can compare the amount of variation between the two images with a predefined threshold that indicates a characteristic of whether the specimen is substantially static or dynamic. If the amount of variation is smaller than the threshold, the specimen is deemed as static and a static analytical algorithm is selected to process the captured images. On the other hand, if the amount of variation is equal to or greater than the threshold, the specimen is deemed as dynamic and a dynamic analytical algorithm is selected for subsequent processing.

The plurality of images can include a sequence of images taken in a short period of time. In some embodiments, 2 to 600 images can be taken within 0.04 to 10 seconds, e.g., at a rate of 60 images per second. In another example implementation, the rate can be 15 images per second. For example, a sequence of 45 images can be taken in 3 seconds. The device can select two images that are taken temporally and/or sequentially apart from each other so that the amount of variation between the two images can be more apparent. For example, the two images can be 2 to 5 seconds apart, e.g., selecting the first image and the last image in the sequence.

At step 4730, in the manners described here, the device can perform a set of analytic processes that corresponds to the selected analytic algorithm on the captured imagery to generate an analytic result associated with the biological specimen.

Figure 19:
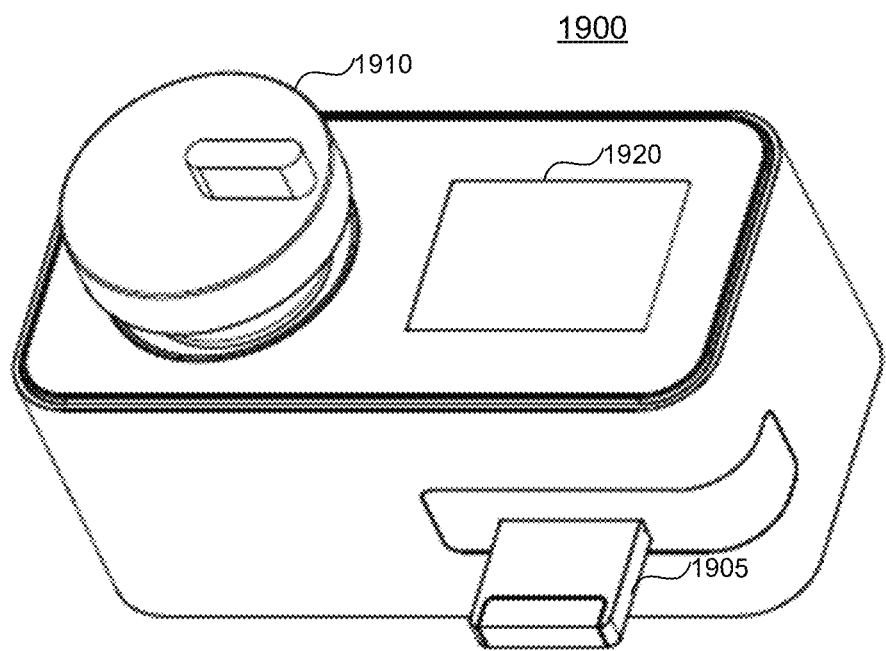
FIG. 19 is a schematic diagram of a testing equipment including a collection bottle.

FIG. 19 is a schematic diagram of a testing equipment including a collection bottle according to at least one embodiment of the invention. A test strip device 1905 can be inserted into the testing equipment 1900 through an insertion port. The test strip device 1905 can include a collection bottle 1910 for collecting the specimen (e.g., sperm specimen) or include a slot for accommodating the collection bottle. The testing equipment 1900 can include a sensor (not shown) to detect whether the collection bottle 1910 is inserted into the testing equipment 1900.

The testing equipment 1900 can have a timer mechanism for determining a time period during which the collection bottle 1910 is being inserted into the testing equipment 1900. Once the collection bottle 1910 containing the specimen is inserted, the testing equipment 1900 can wait for a pre-determined time period (e.g., 30 minutes) for liquefaction of the specimen before prompting a user to transfer the specimen from the collection bottle 1910 to the test strip device 1905. In some embodiments, the testing equipment 1900 can include a camera or a sensor to determine whether the specimen already liquefies.

Furthermore, the testing equipment can include a moving mechanism to apply a mechanical force to the collection bottle 1910 in order to mix specimen in the collection bottle 1910. For example, the moving mechanism can, e.g., shake, vibrate, or rotate the collection bottle 1910. In some other embodiments, the testing equipment can include a rod to be inserted into the collection bottle 1910 and to stir the specimen in the collection bottle 1910.

The testing equipment 1900 optionally can include a screen 1920 for display information. For example, the screen 1920 can show instructions or hints on how to operate the testing equipment 1900. The screen 1920 can also show test results after the testing equipment 1900 conducts the test. Additionally or alternatively, the testing equipment 1900 may include a known communication module so that it may communication (e.g., the analysis results, and/or the images taken by the camera modules) with a user's computing device (e.g., a smart phone with a mobile software application, or a traditional personal computer such as a laptop). The test equipment 1900 is operable to receive an instruction from a user (e.g., from screen 1920 and/or from the aforementioned communication module), and to perform a select number of the automated analytic processes based on the instruction. The testing equipment 1900 can also display results and/or images of the specimen, either on the screen 1920, or to the user's computer (e.g., via aforementioned communication module), or both.

Similar to the testing equipment illustrated in FIGS. 14A and 14B, the testing equipment 1900 can include a camera (not shown) for capturing images or videos of the test strip device 1905. The testing equipment 1900 can further include a processor (not shown) for processing the images or videos for determining test results (e.g., through the process illustrated in FIG. 16).

In some embodiments, for example, the magnifying component 2110 is a magnifying lens. The magnifying power of the magnifying component 2110 can be represented by either angular magnification ratio or linear magnification ratio. An angular magnification ratio is a ratio between an angular size of an object as seen through an optical system and an angular size of the object as seen directly at a closest distance of distinct vision (i.e., 250 mm from a human eye). A linear magnification ratio is a ratio between a size of an image of an object being projected on an image sensor and a size of the actual object.

For example, the magnifying lens can have a focal length of 6 mm, a thickness of 1 mm and a diameter of 2 mm. Assuming 250 mm is the near point distance of a human eye (i.e., the closest distance at which a human eye can focus), the angular magnification ratio is 250 mm/6 mm=41.7x. The distance between the magnifying component 2110 and the specimen holding area 2115 can be, e.g., 9 mm. As a result, a linear magnification ratio can approximate 2. In other words, a size of an image of an object on the image sensor caused by the magnifying component is 2 times a size of the actual object below the magnifying component.

In some embodiments, the magnifying component has a focal length of 0.1-8.5 mm. In some embodiments, the linear magnification ratio of the magnifying component is at least 1. In some embodiments, the linear magnification ratio of the magnifying component is from 0.5 to 10.0.

In some embodiments, a supplemental lens 2135 is placed below the camera module 2130 for further magnifying the image and decreasing the distance between the magnifying component 2110 and the specimen holding area 2115. The effective linear magnification ratio of the whole optical system can be, e.g., 3. In other words, the image of the object captured by the camera module 2130 is has a size that is 3 times size of the actually object in the specimen holding area 2115. In some embodiments, the effective linear magnification ratio of the whole optical system of the testing equipment is from 1.0 to 100.0, preferably from 1.0 to 48.0.

In some embodiments, the image sensor of the camera module has a pixel size of 1.4 μm. Typically, a captured image of an object needs to take at least 1 pixel in order to properly analyze the shape of the object. Thus, the size of the captured image of the object needs to be at least 1.4 μm. If the linear magnification ratio of the testing equipment is 3, the testing equipment can properly analyze the shape of objects having a size of at least 0.47 μm.

In some embodiments, the image sensor of the camera module has a pixel size of 1.67 μm. Then the size of the captured image of the object needs to be at least 1.67 μm in order to properly analyze the shape of the object. If the linear magnification ratio of the testing equipment is 3, the testing equipment can properly analyze the shape of objects having a size of at least 0.56 µm.

In some embodiments, for example, the length of the whole optical system can be, e.g., 24 mm. The distance between the bottom of the magnifying component and the top of the specimen holding area 2115 can be, e.g., 1 mm. In some embodiments, length of the whole optical system of the testing equipment is from 2 mm to 100 mm, preferably from 5 mm to 35 mm.

Figure 20:
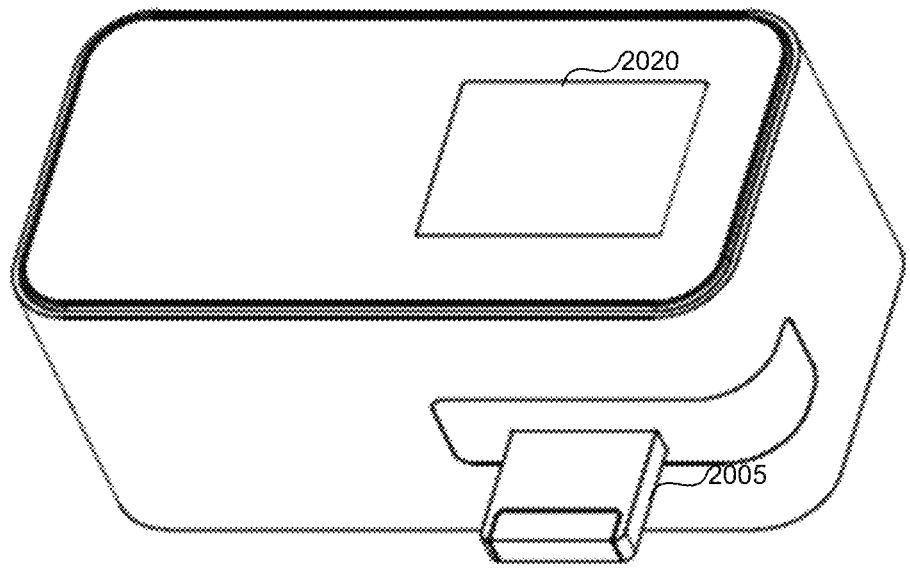
FIG. 20 is a schematic diagram of a testing equipment does not include a collection bottle.

FIG. 20 is a schematic diagram of a testing equipment does not include a collection bottle, according to at least one embodiment of the invention. Unlike the testing equipment 1900, the testing equipment 2000 does not include a collection bottle or a slot for inserting a collection bottle. The specimen is directly applied to the test strip device 2005, by a user or an operator, without being collected in a collection bottle.

Figure 21A:
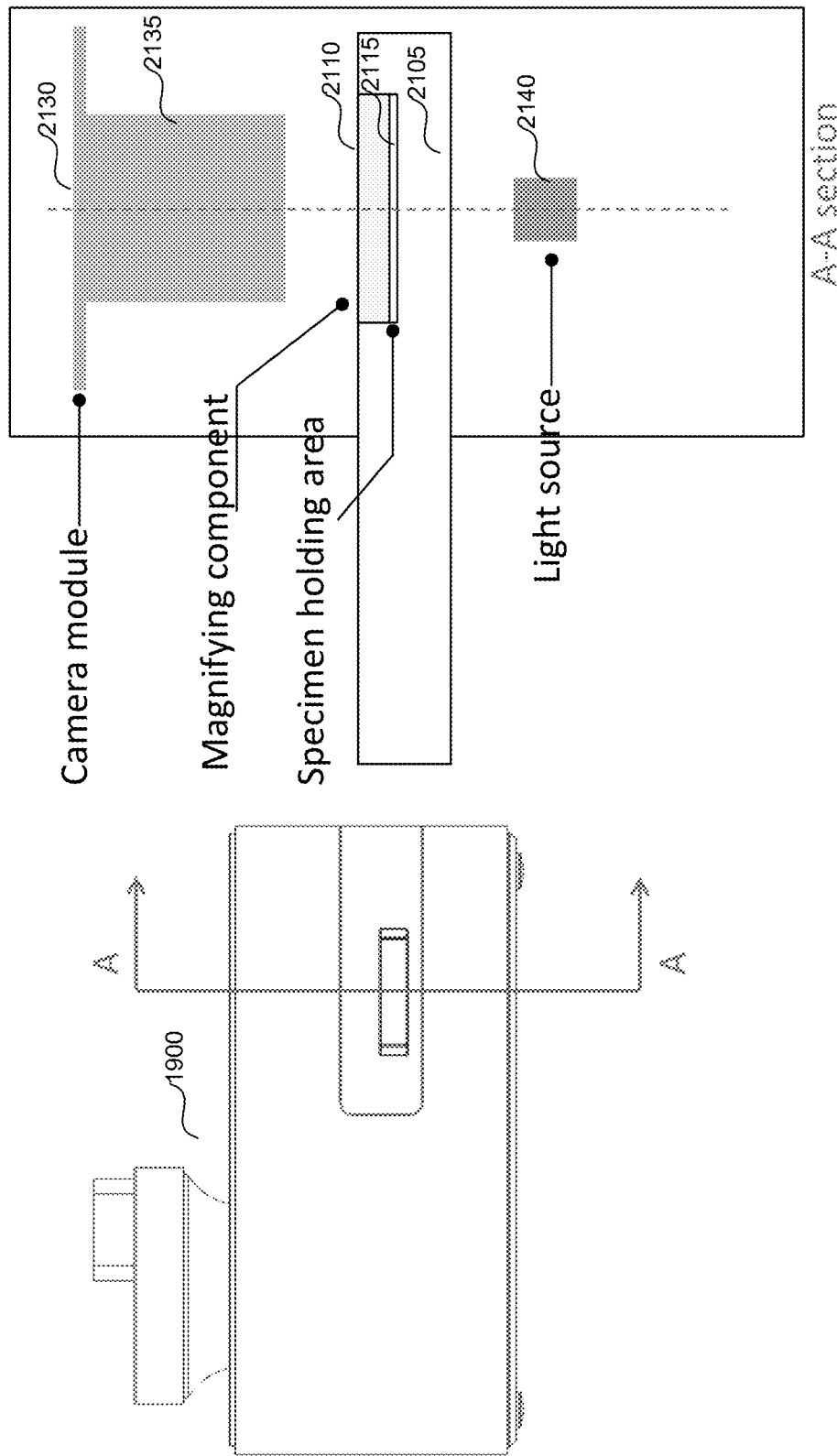
FIGS. 21A and 21B are cross-sectional views of various embodiments of a testing equipment.

FIG. 21A is a cross-sectional view of an embodiment of the testing equipment 1900. The A-A section of the testing equipment 1900 shows a camera module 2130 on top of the test strip device 2105 for capturing images or videos of the specimen holding area 2115 of the test strip device 2105. The test strip device 2105 includes a magnifying component 2110 on top of the specimen holding area 2115. A light source 2140 below the test strip device 2105 provides illumination for the specimen holding area 2115. In some other embodiments, light source can be placed on top of the test strip device or laterally at a side of the test strip device. There can be multiple light sources or an array of light sources for providing illumination on the test strip device. In some embodiments, different combinations of light sources can be switched, adjusted, or selected depending on the analyte types, such that the analyte is illuminated by light with a proper color.

In some embodiments, the test strip device 2105 can include a test strip in or near the specimen holding area 2115. For example, the test strip can be a pH test strip, an HCG (human chorionic gonadotropin) test strip, an LH (luteinizing hormone) test strip or a fructose test strip. When the analyte of specimen in the specimen holding area interacts with the chemical or biochemical agents in the test strip, some optical properties (e.g., color or light intensity) of the test strip can change. The camera module 2130 can capture the color or intensity of the test strip to determine a test result, such as a pH level, an HCG level, an LH level or fructose level. In some embodiments, the magnifying component 2110 above the test strip can be replaced with a transparent or translucent cover. Therefore, the testing equipment can simultaneously conduct a qualification of the analyte in the specimen and conduct a further analysis of the specimen through one or more magnified images of specimen.

Figure 21B:
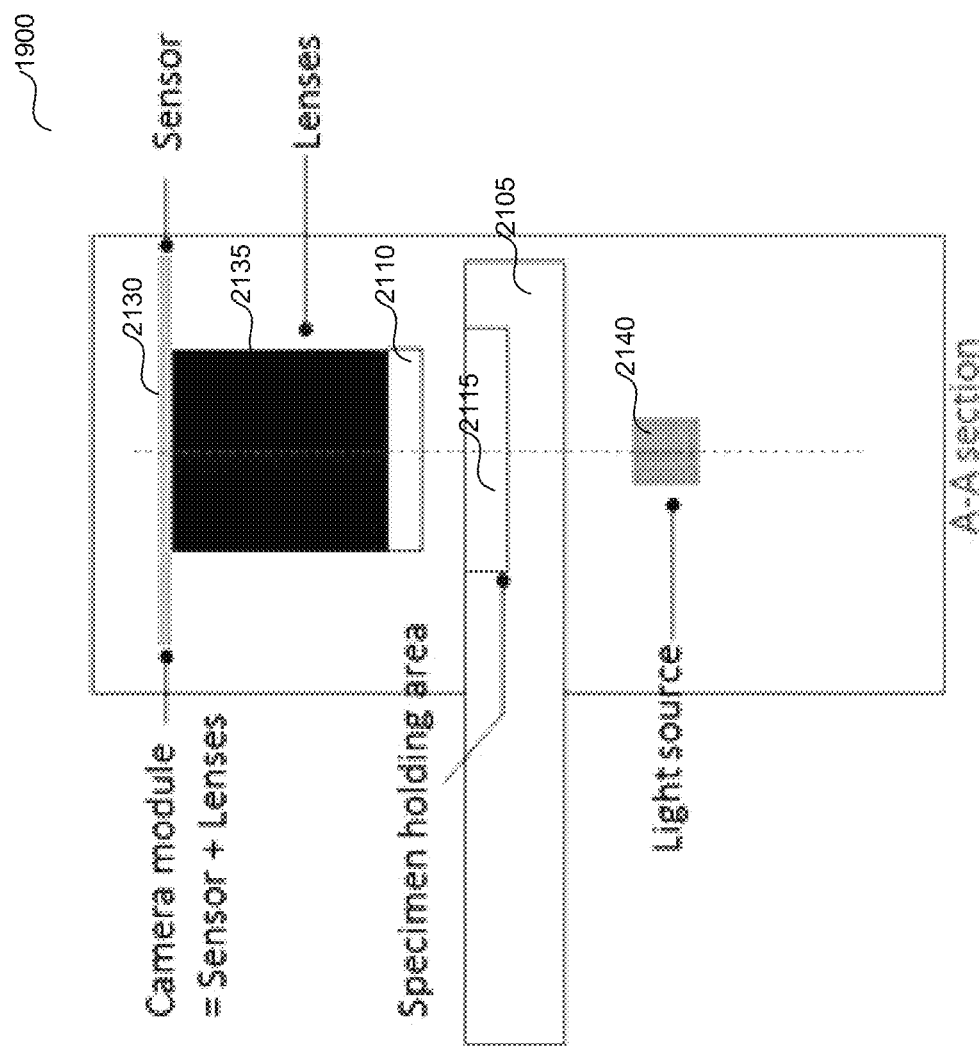

FIG. 21B is a cross-sectional view of another embodiment of the testing equipment 1900. The A-A section of the testing equipment 1900 shows a camera module 2130, which includes a sensor and one or more lenses 2135 (also referred to as supplemental lenses or optical lens module), on top of the test strip device 2105 for capturing images or videos of the specimen holding area 2115 of the test strip device 2105. A light source 2140 below the test strip device 2105 (or disposed at other places) provides illumination for the specimen holding area 2115. A magnifying component 2110 can be attached to the bottom of the lenses 2135, instead of being on top of the specimen holding area 2115 as illustrated in FIG. 21A. In some embodiments, the element 2110 can be a flat light-transmissive cover having no magnification power, if the lenses 2135 provide enough magnification power. In some other embodiments, the testing equipment 1900 does not include the magnifying component 2110, if the lenses 2135 provide enough magnification power (e.g., if the linear magnification ratio of the lenses 2135 is at least 1.0).

Figure 22:
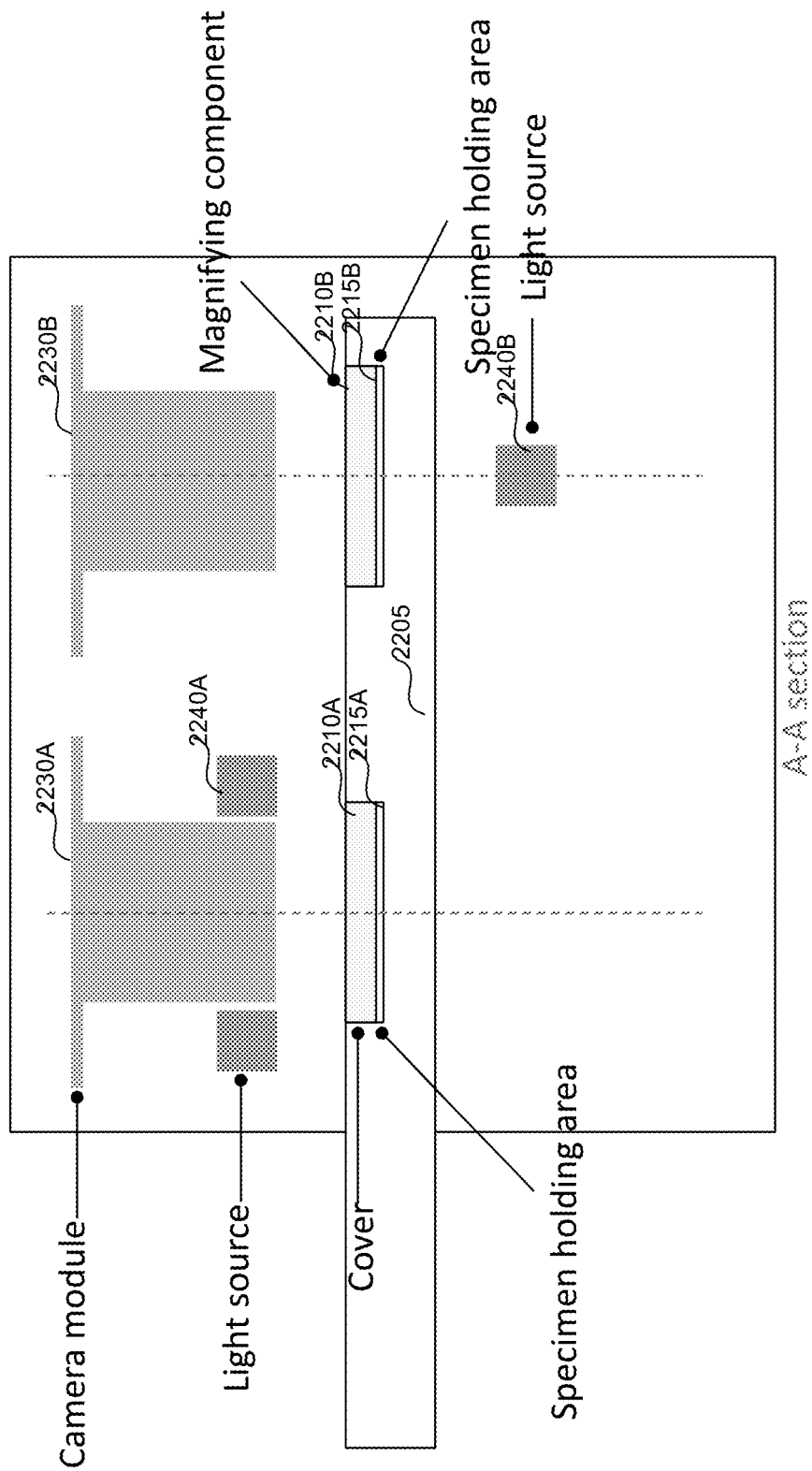
FIG. 22 is a schematic diagram of a testing equipment for a test strip device having two specimen holding area.
Figure 29:
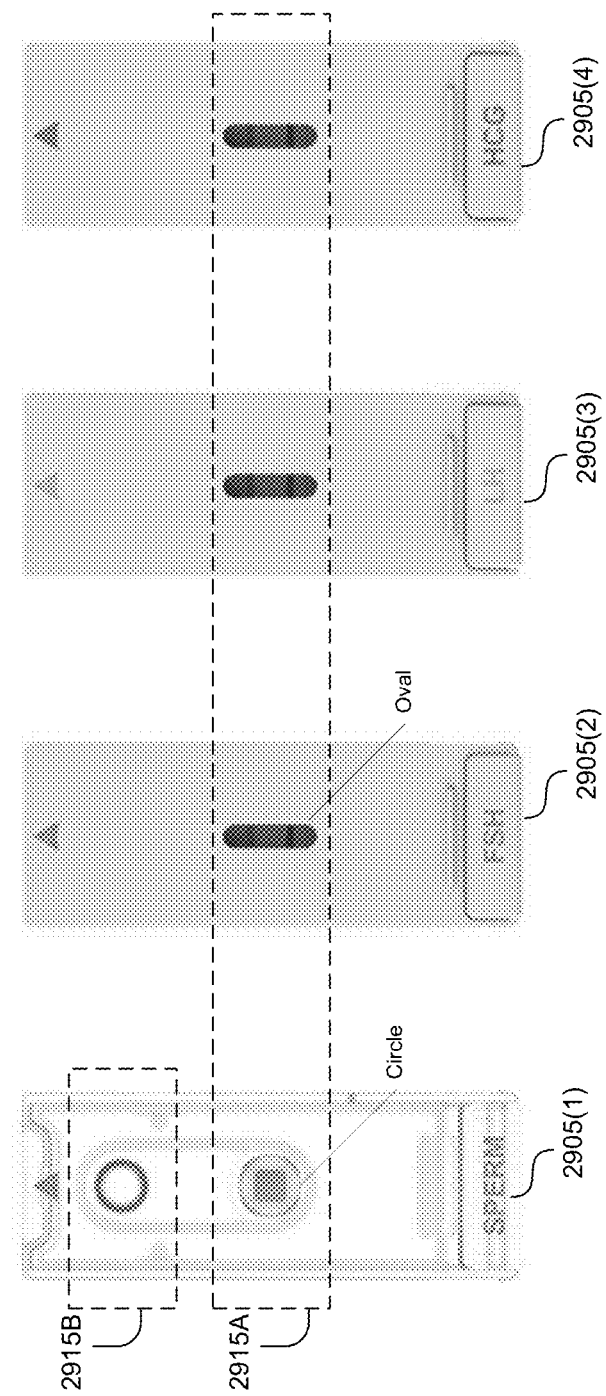
FIG. 29 shows examples of carriers that may be suitable for a test equipment with a multi-camera configuration, such as the test equipment shown in FIG. 22.

FIG. 22 is a schematic diagram of a testing equipment for a test strip device having two specimen holding areas. FIG. 29 shows examples of carriers that may be suitable for a test equipment with a multi-camera configuration, such as the test equipment shown in FIG. 22. With simultaneous reference to FIGS. 19 and 20, the test equipment shown in FIG. 22 can be another variant of the testing equipment 1900 (i.e., with a collection bottle) or the testing equipment 2000 (i.e., without the collection bottle). As shown in FIG. 22, a receiving mechanism is included in the test equipment to receive one or more carriers (e.g., a test strip device, such as test strip device 2205, or a collection bottle such as bottle 1910), which can be inserted through the opening(s) on the casing of the test equipment.

In some embodiments, a single carrier can include a first holding area and a second holding area, such as shown by the test strip device 2205 in FIG. 22. As shown in FIG. 22, at least two camera modules can be included in the test equipment. The two camera modules include a first camera module 2230A and a second camera module 2230B, arranged to capture images and/or videos of the first holding area 2215A and the second holding area 2215B, respectively. More specifically, the test strip device 2205 can include a specimen holding area 2215A and another specimen holding area 2215B. In some examples, a transparent or translucent cover 2210A is placed on top of the specimen holding area 2215A. The light source 2240A can be controllable and can provide illumination on the specimen holding area 2215A. The camera module 2230A is positioned to capture images or videos of the specimen holding area 2215A. As an optional implementation, a magnifying component 2210B can be placed on top of the specimen holding area 2215B. Further, in some embodiments, the light source 2240B is operable to provide illumination on the specimen holding area 2215B. The camera module 2230B is positioned to capture images or videos of the specimen holding area 2215B. The first and second holding areas may directly carry the biological specimen or have been exposed to the biological specimen. Similar to the structures introduced with respect to FIG. 14B, in some embodiments, the test equipment can include a light collimator for collimating light beams emitted from the light source to at least one of the holding areas. In some embodiments, an annular diaphragm can be further included between the light source and the light collimator for forming a hollow cone of light beams that travels through the light collimator and then reaches the specimen holding area. In some additional embodiments, a phase plate can be included between the specimen holding area and at least one of the camera modules for phase-shifting light rays reflected from the specimen holding area.

As an alternative to a single carrier having multiple holding areas, multiple carriers can be inserted into the test equipment through their respective openings, ports, or slots. For example, two separate test strips devices can include the specimen holding areas 2215A and 2215B respectively. Depending on the need of the test, the location of the specimen holding areas 2215A and 2215B in the test strips can be designed to be aligned with the camera modules 2230A and 2230B. In some embodiments, the two test strip devices are inserted into the testing equipment through two separate insertion ports.

Among other benefits, the convenience and easiness of testing are two prominent benefits that the test equipment disclosed here can provide. According to the present embodiments, a user of the disclosed test equipment need not possess any professional knowledge on how to perform various types of analysis on the biological specimen before the user can utilize the test equipment to produce a result. Accordingly, the test equipment can include a processor for performing automated analytic processes on the specimen and determine an outcome with regard to the specimen. The processor can be carried by a main circuit board (i.e., a known component, not shown for simplicity). Further, the test equipment is preferably small and not as bulky as traditional test equipment commonly seen in the laboratories. Accordingly, in some embodiments, such as those shown in FIGS. 19 and 20, the receiving mechanism for the carrier, the camera modules, and the main circuit board can all be enclosed within the casing of the test equipment. The test equipment may have a small form factor, such as smaller than 30 cm×30 cm×30 cm, that is, 27,000 cm$^3$. In some embodiments, the test equipment can further include a battery compartment enclosed within the casing, such that a battery can be installed in the battery compartment to power the test equipment.

In some embodiments, the processor included in the test equipment can perform different analysis on different holding areas, and can derive the result based on a combination of results from the analyses performed on the different areas. In other words, the processor can be configured to perform a first analytic process on the captured images of the first holding area, to perform a second analytic process different from the first analytic process on the captured images of the second holding area, and to determine an outcome with regard to the biological specimen based on results from both the first and the second analytic processes. As used herein, the term "analytic process" means a process that can evaluate one or more pieces of information collected from a number of sources (e.g., the images of the holding areas), and produce a result, a conclusion, an outcome, an estimate, or the like, regarding the source.

According to some examples, the testing equipment can use a combination of the camera module 2230A, light source 2240A and cover 2210A to quantify an analyte or to determine a property of the specimen (e.g., pH level, LH level, HCG level, or fructose level). Additionally, the testing equipment can further use a combination of the camera module 2230B, light source 2240B and magnifying component 2210B to analyze a magnified image of the specimen to determine properties of the specimen (e.g., sperm quantity, sperm motility, sperm morphology, etc.). Depending on the requirements of various types of biochemical tests, different combinations or configurations of light source(s) can be used to illuminate the biochemical specimen. The multi-camera configuration is particularly advantageous because different analytic processes can be performed through different camera modules without the need for the user to change the carrier (e.g., test strip device), thereby expediting the outcome generation and reducing the complexity of necessary human operation. The light sources 2240A and 2240B are enclosed inside the casing and arranged to illuminate the biological specimen for at least one of the camera modules. According to one or more embodiments, the processor is configured to control the light source based on which analytic process that the processor is currently configured to perform.

Moreover, in some embodiments, the processor can perform different analytic processes based on a visual cue on the carrier. For example, some embodiments can perform image recognition and processing on the images of the holding areas, and can perform different analytic processes according to a visual cue from the results of the image recognition. Example carriers 2905(1)-2905(4) are shown in FIG. 29, where carrier 2905(1) is for fertility testing with regard to reproductive cells for a male subject (e.g., via his sperm), and carriers 2905(2), 2905(3) and 2905(4) are for fertility testing with regard to reproductive cells for a female subject (e.g., via her urine). As shown, the carriers 2905(1)-2905(4) all have a first holding area 2915A that corresponds to the location of the first camera module 2230A, but only the carrier 2905(1) includes a second holding area 2915B. In some examples, the visual cue on the carrier can be a shape of a particular holding area (e.g., the holding area 2215A). For the discussion herein, a shape of a holding area means the general periphery (or an outer perimeter) of the holding area. For example, the shape may be a circle, an oval, a triangle, a rectangle, or any suitable shape that is identifiable by a processor utilizing known image processing techniques on images of the holding area as captured by a respective camera module (e.g., camera module 2230A). Additional example of the visual cue may include a graphic pattern, a visual indicium, a one-dimensional barcode, a multi-dimensional pattern code (e.g., QR code), and so forth.

With simultaneous reference to FIGS. 22 and 29, in some embodiments, when the processor identifies (e.g., via the first camera module 2230A) that the first holding area (e.g., area 2215A, or area 2915A of carrier 2905(1)) be in a first shape (e.g., a circle), the processor is configured to perform a certain analytic process (e.g., fertility of a male subject, such as from various properties of his sperm sample), and when the first holding area (area 2215A, or area 2915A of carrier 2905(2)) is in a second shape (e.g., an oval), the processor is to perform a different analytic process (e.g., analysis of fertility of a female subject, such as from the hormone level of her urine sample). In this way, not only is the test equipment not limited to perform only one type of test (e.g., fertility of sperm), but it can also switch the analytic processes accordingly based on the carrier (e.g., test trip device) inserted into the machine.

More specifically, according to some implementations, when the shape represents that the biological specimen includes sperm from a male subject, then the process can determine one or more properties of the sperm, such as those introduced herein. The determination of the one or more properties of the sperm may be performed, in some examples, by using the second camera module 2230B. For some specific examples, the properties can be determined may include: a concentration of the sperm, a motility of the sperm, and/or a morphology of the sperm. According to some embodiments, the processor is configured to (1) determine a concentration of the sperm and/or a morphology of the sperm based on a single image from the captured images, and (2) determine a motility of the sperm based on two or more images from the captured images.

Figure 30:
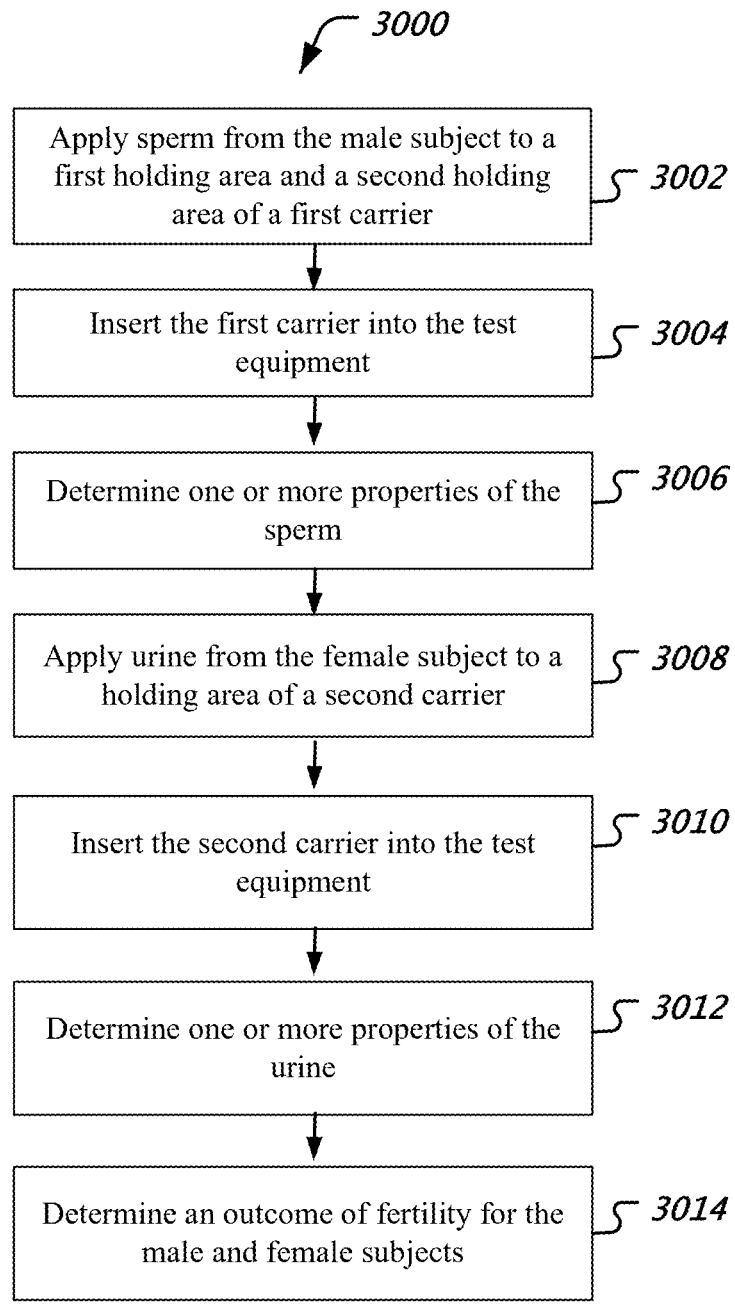
FIG. 30 is a flow chart of a process for utilizing a test equipment disclosed here to analyze fertility for both a male subject and a female subject.

With the above in mind, FIG. 30 is a flow chart of an example process 3000 for utilizing a test equipment disclosed here (e.g., in FIG. 22) to analyze fertility for both a male subject and a female subject. With continued reference to FIG. 29, the process 3000 is explained below. Note that the following example applies the specimen from male first then female, but the reverse order (i.e., female and then male) can be performed with no effect on the accuracy of the result.

First, in step 3002, the user can apply a biological specimen (e.g., sperm) from the male subject to a first holding area (e.g., area 2915A) and a second holding area (area 2915B) of a first carrier (e.g., carrier 2905(1)). Next, in step 3004, the user is to insert the first carrier into the test equipment (e.g., such as the one shown in FIG. 22), and because the shape of the first holding area 2915A of carrier 2905(1) is circle, the test equipment can automatically acquire the knowledge that the current specimen contains sperm from a male and selects analytic processes accordingly. Then, in step 3006, the user can use the test equipment to determine one or more properties of the sperm. For example, as discussed here, the processor in the test equipment can utilize the first camera module 2230A to take images of the first holding area 2915A of the carrier 2095(1), which can include a test strip that shows different color in response to different acidity, and recognize the color of the test strip to determine the acidity of the sperm. Additionally, in step 3006, the processor in the test equipment can utilize the second camera module 2230B to determine one or more properties of the sperm selected from the group consisting of: concentration of the sperm, motility of the sperm, and morphology of the sperm;

Next, in step 3008, the user can apply urine from the female subject to a holding area 2915A of a second carrier (e.g., carrier 2905(2)). In step 3010, the user inserts the second carrier into the test equipment, and because the shape of the first holding area 2915A of carrier 2905(2) is oval, the test equipment can automatically acquire the knowledge that the current specimen contains urine from a female and selects analytic processes accordingly. In step 3012, the test equipment determines one or more properties of the urine, e.g., by utilizing the second camera module 2230B. For example, the test strip may be suitable for enabling the test equipment to determine a concentration level of one or more types of female hormones (e.g., FSH, LH, or HCG). Lastly, in step 3014, the user utilizes the test equipment to automatically analyze the results of the male and the female biological specimen and determine an outcome with regard to the subjects' fertility.

In some specific examples, the first camera module 2230A may have a lower camera resolution than the second camera module 2230B, and therefore the two cameras are utilized by the processor to perform different analytic processes. Additionally, the first camera module 2230A may have a lower magnifying ratio than the second camera module 2230B. Some examples of the first camera module 2230A may have no magnifying function at all, while the second camera module 2230A may have a fixed magnifying ratio. In addition or as an alternative to the second camera module 2230B itself having a higher magnifying ratio, the cover 2210B for the second holding area 2215B can include a magnifying component, such as illustrated in FIG. 22. In some implementations, the magnifying ratio of the camera modules may be adjustable (e.g., as controlled by the processor). Some examples of the test equipment provide that the first camera module 2230A has a camera resolution of 2 megapixels or above, and that the second camera module 2230B has a camera resolution of 13 megapixels or above. In some examples, the second camera module 2230B may include a linear magnifying ratio of at least 4.8 times or above.

In some of these examples, the processor is further to determine at least one additional property of the sperm by using the first camera module 2230A. This additional property may include an acidity of the sperm. For example, the carrier can include a pH indicator in the first holding area 2215A to represent the acidity of the sperm with colors, through which the processor can recognize for identifying the acidity. Similarly, some examples provide that the processor can determine a biochemical property of the biological specimen based on a color of a region in the one or more images of the first or second holding area.

Continuing with the above test equipment examples with multi-camera configurations in FIG. 22 and the carrier examples in FIG. 29, in some implementations, when the processor identifies the first holding area (e.g., area 2215A, or area 2915A of carrier 2905(2)) being in a second shape, such as an oval, which may indicate that the biological specimen includes urine from a female subject, the processor is configured to determine one or more properties of the urine. The properties can be determined can include: an LH level, an FSH level, and/or an HCG level. Like acidity, the determination of the one or more properties of the urine may be performed by using the first camera module. Similarly, the carrier can include an LH indicator (e.g., as shown in carrier 2905(3)), an FSH indicator (e.g., as shown in carrier 2905(2)), and/or an HCG indicator (e.g., as shown in carrier 2905(4)) in the first holding area (e.g., area 2915A of respective carriers).

Furthermore, in some embodiments, the processor can utilize at least one of the two camera modules (e.g., the first camera module 2230A), or another sensor (e.g., light sensor 2690, introduced below with respect to FIG. 26), to determine a readiness or a validity of the biological specimen before performing the analytic processes. In some implementations, the readiness or the validity of the test sample can be determined based on identifying whether a first visual indicium is displayed in a particular area (e.g., where line 2916 is shown in FIG. 29) in the first holding area (e.g., area 2915A). An example of such first visual indicium can be a line displayed in a certain designated area on a test strip, such as shown in FIG. 29 as red line 2916. The red line 2916 may be used to as a quality control means, which can indicate that the test is valid or that the result is ready. Additionally, the first hold area 2915A may include another area (e.g., where line 2917 is shown in FIG. 29) that is to display a second visual indicium representing a test result with respect to a property of the biological specimen. An example of such second visual indicium can be a line displayed in another certain designated area on the test strip, such as shown in FIG. 29 as red line 2917.

In some embodiments, the test equipment can perform an action in response to a determination that the biological specimen is not ready. In some examples, the action to be performed by the processor includes implementing a timer having a time duration that is determined by the analytic processes to be performed. In some other examples, the test equipment further includes a moving mechanism, and the processor in the test equipment can utilize the moving mechanism to apply a mechanical force to the carrier for increasing the readiness of the biological specimen. More detail of the actions and mechanisms that can be implemented in the test equipment are introduced below with respect to FIGS. 25 and 26.

The locations of the magnifying components (e.g., magnifying component of the camera module or magnifying component of the test strips) and locations of the light source(s) can be adjusted or selected depending on the requirements of various types of analyte analysis. In variations, the camera modules can have adjustable magnifying ratios. In at least some of these examples, the processor is further configured to adjust a magnifying ratio of at least one of the two camera modules based on which analytic process that the processor is currently configured to perform. As introduced above, when the biological specimen includes sperm, the test equipment can configure suitable camera modules (e.g., the second camera module 2230B) to reach a different magnifying ratio for determining a motility of the sperm and a morphology of the sperm.

Figure 23:
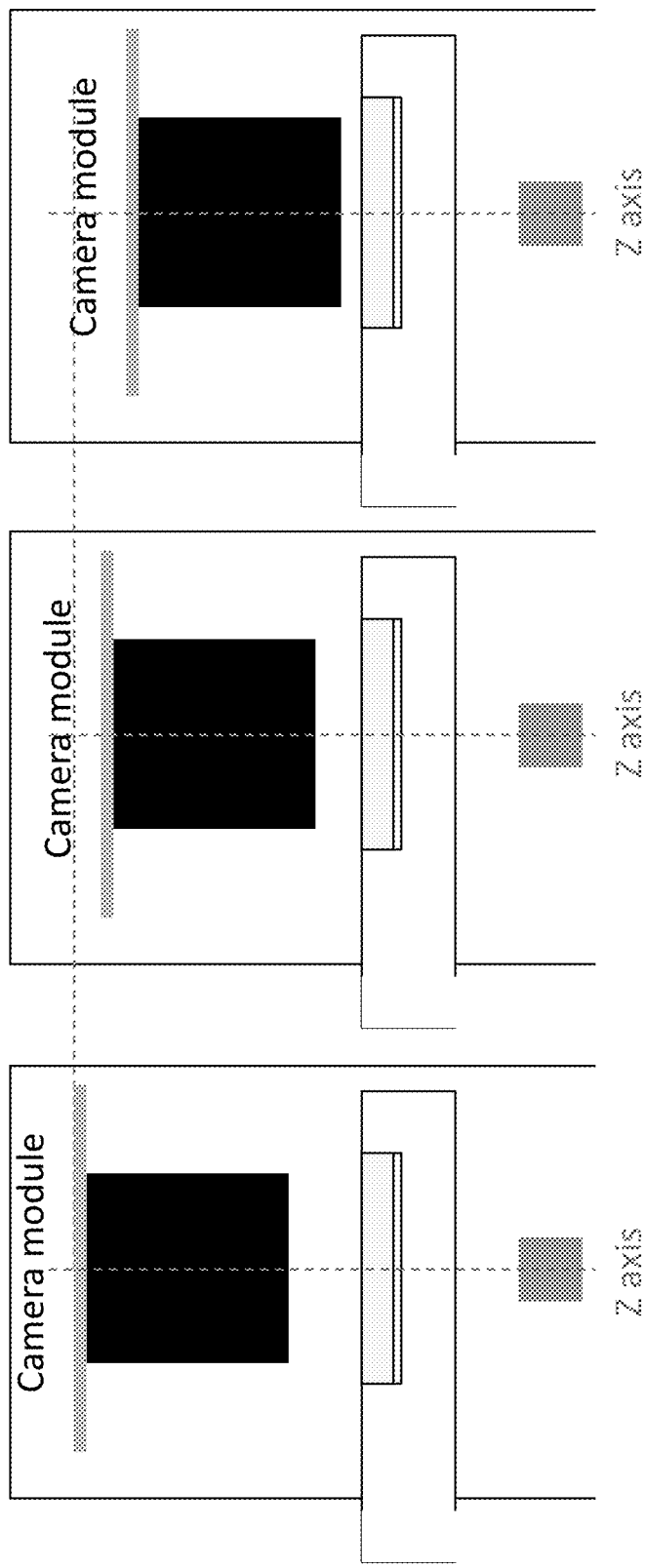
FIG. 23 is schematic diagram of components of a testing equipment having an autofocus function.

Note that an optimal distance between the camera module and the magnifying component may have a low margin of error. For example, even a slight deviation of 0.01 mm from the optimal distance can prevent the camera module to capture a clear image of the specimen holding area. In order to fine tune the distance between the camera module and the magnifying component, the testing equipment can include an autofocus (AF) function. An autofocus function is function that automatically adjusts an optical system (e.g., adjusts distances between components of the optical system) so that the object being imaged (e.g., semen) is within the focal plane of the optical system. At least one or more embodiments also provide a mechanical focusing mechanism, controllable by the processor, to cause at least one of the two camera modules to focus on a respective holding area. The mechanical focusing mechanism is discussed in more detail below with respect to FIGS. 23 and 24. The mechanical focusing mechanism can be controllable to adjust a position of a lens in the at least one of the two camera modules (e.g., such as generally shown in FIG. 23). Additionally or alternatively, the mechanical focusing mechanism can be controllable to adjust a position of the carrier (e.g., such as generally shown in FIG. 24).

FIG. 23 is schematic diagram of components of a testing equipment having an autofocus function. As shown in FIG. 23, the testing equipment can move the camera module upward or downward along the Z-axis (e.g., by a motorized rail, an ultrasonic motor drive, or a stepping motor). By adjusting the vertical position of the camera module, the testing equipment can adjust the distance between the camera module and the magnifying component.

Figure 24:
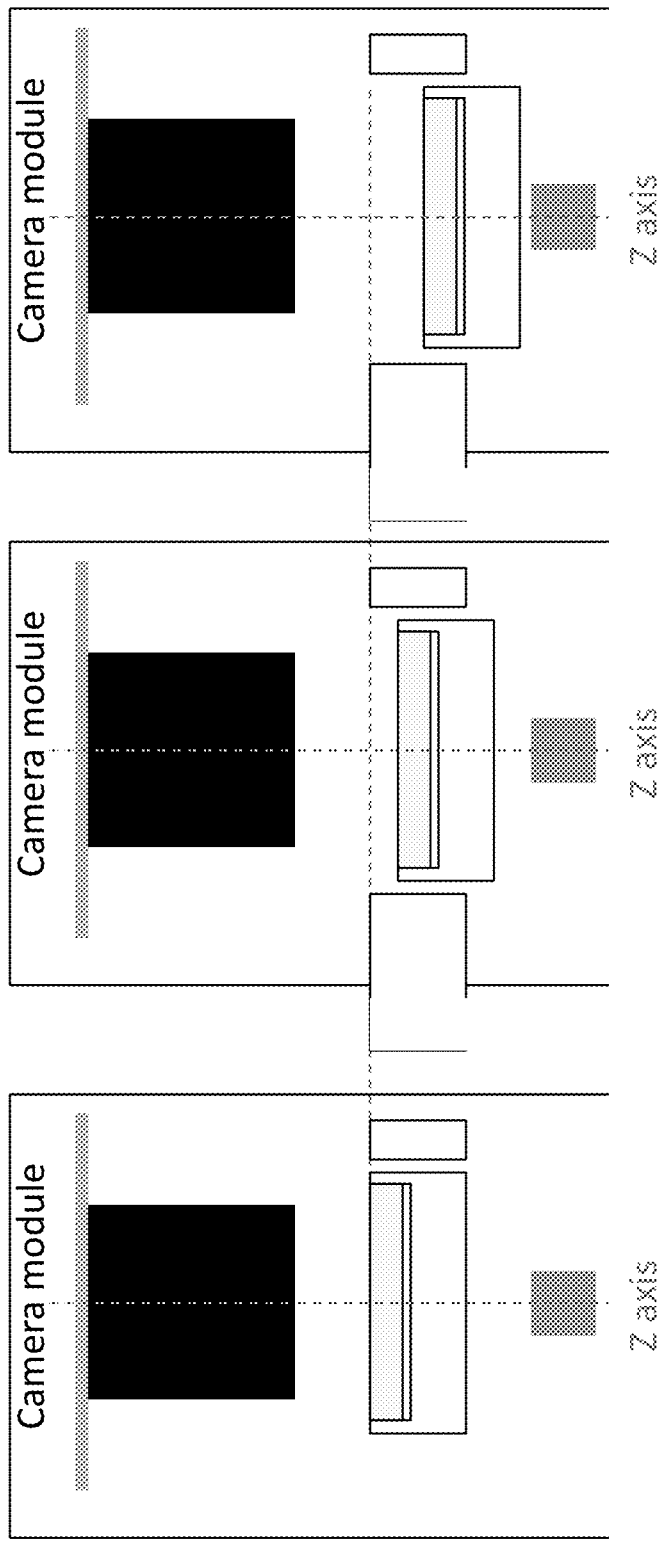
FIG. 24 is schematic diagram of components of another testing equipment having an autofocus function.

FIG. 24 is schematic diagram of components of another testing equipment having an autofocus function. As shown in FIG. 24, the testing equipment can move the test strip device upward or downward along the Z-axis. By adjusting the vertical position of the test strip device, the testing equipment can adjust the distance between the camera module and the magnifying component.

During the autofocus operation as illustrated in FIG. 23 or 24, the camera module and the supplemental lens are kept as a single module. In other words, the distance between the camera module and the supplemental lens remains unchanged during the autofocus operation as illustrated in FIG. 23 or 24.

Figure 25:
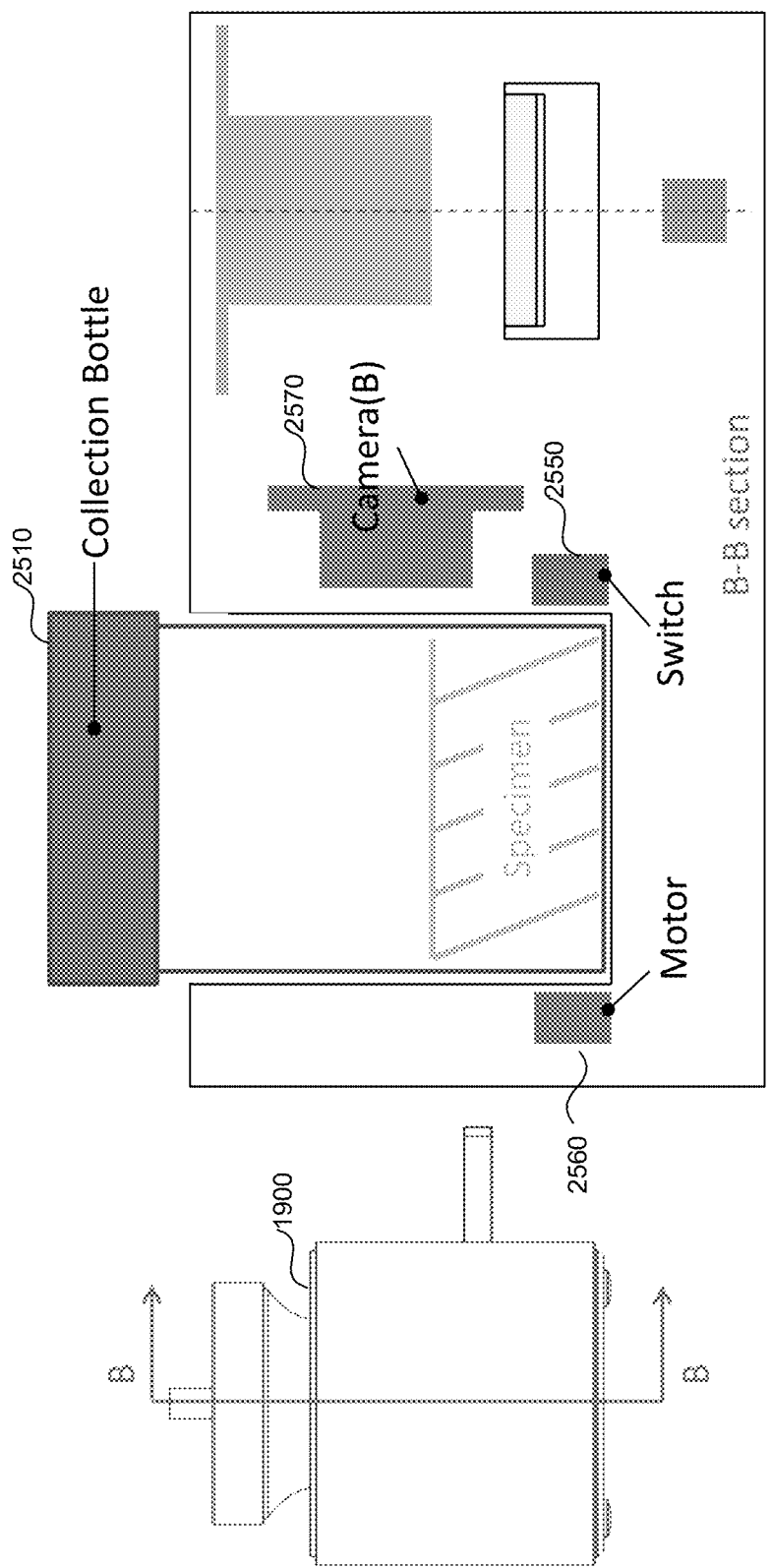
FIG. 25 is a schematic diagram of a testing equipment including a switch and a motor.

FIG. 25 is a schematic diagram of a testing equipment including a switch and a motor. The B-B cross-section of the testing equipment 1900 in FIG. 25 shows various components of the testing equipment. The testing equipment 1900 includes a switch 2550 to detect a collection bottle 2510 being inserted into the testing equipment 1900. When the collection bottle 2510 is inserted, the switch 2550 is activated. The testing equipment 1900 then is notified of the collection bottle 2510 through the switch 2550. Based on the time period for which the switch 2550 is being activated, the testing equipment can determine the time period for which the collection bottle 2510 stays inserted.

The testing equipment 1900 further includes a motor 2560 for shaking, vibrating, or rotating the collection bottle 2510 in order to mix the specimen in the collection bottle 2510. The testing equipment 1900 can include a camera 2570 to determine whether the specimen already liquefies based on captured images of the specimen in the collection bottle 2510.

Figure 26:
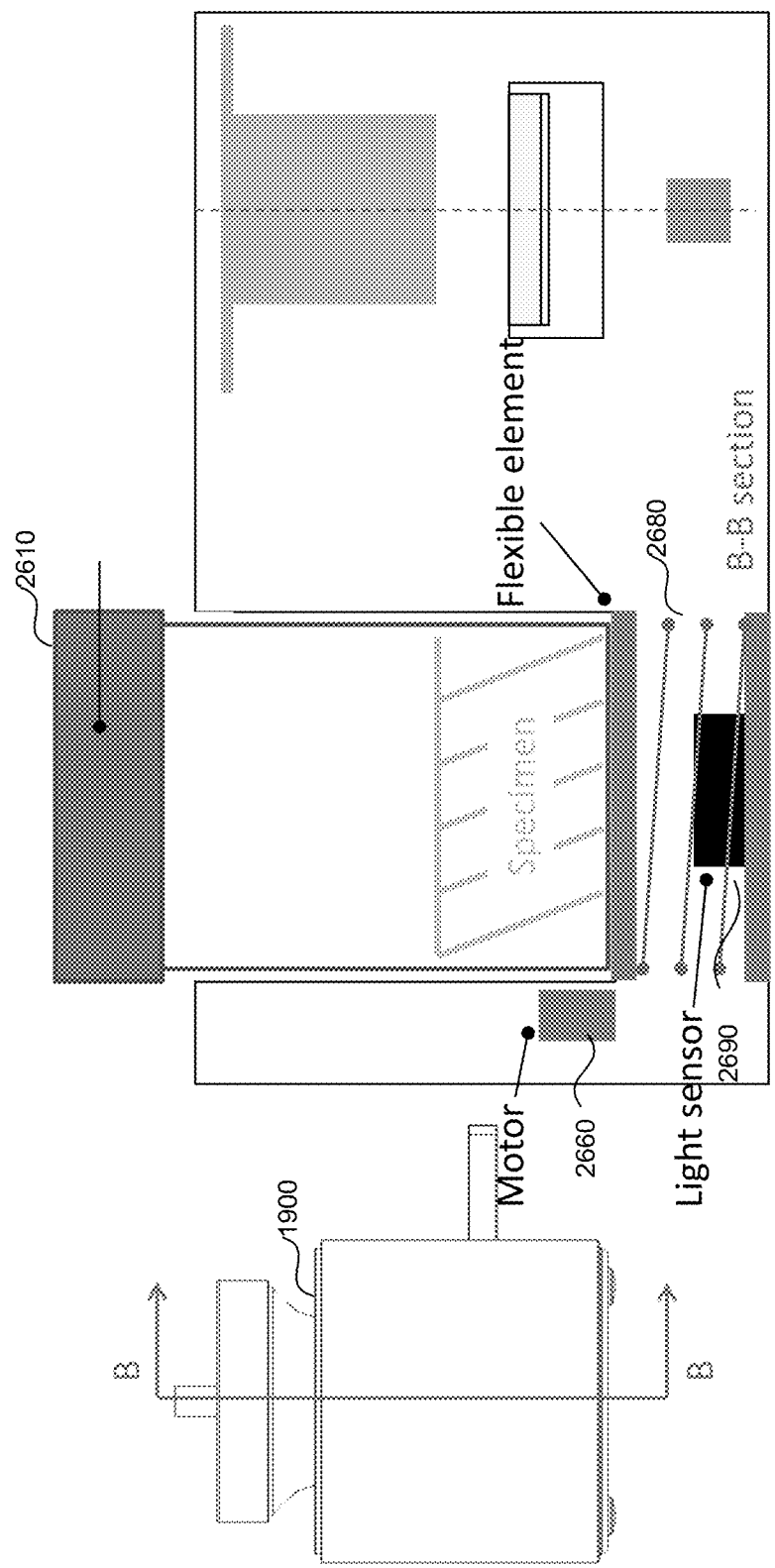
FIG. 26 is a schematic diagram of a testing equipment including a flexible element.

FIG. 26 is a schematic diagram of a testing equipment including a flexible element. The B-B cross-section of the testing equipment 1900 in FIG. 26 shows various components of the testing equipment. The testing equipment 1900 includes a moving element 2680 (e.g. elastic component) at the bottom of the slot for accommodating the collection bottle 2610 in a moving manner. For example, the moving element 2680 can include a spring that can resume its normal shape spontaneously after contraction or distortion. When the collection bottle 2610 is inserted into the slot, the moving element 2680 is compressed. A light sensor 2690 (or other types of distance sensor) is responsible for detecting the distance between the light sensor 2690 and the bottom of the collection bottle 2610. Based on the distance between the light sensor 2690 and the bottom of the collection bottle 2610, the testing equipment 1900 can determine the weight or the volume of the specimen contained in the collection bottle 2610. For example, the distance between the light sensor 2690 and the bottom of the collection bottle 2610 can be inversely proportional to the weight or the volume of the specimen contained in the collection bottle 2610.

In some other embodiments, the testing equipment 1900 can include a sensor on top of the collection bottle 2610. The sensor can be responsible for detecting a distance between the sensor and a top of the collection bottle 2610. The weight or the volume of the specimen contained in the collection bottle 2610 can be determined based on the distance because the volume or the weight can be, e.g., directly proportional to the distance between the sensor and the top of the collection bottle 2610. In turn, based on the weight or the volume of the specimen, the testing equipment 1900 can determine a time period for waiting for the liquefaction of the specimen in the collection bottle 2610. The testing equipment 1900 further includes a motor 2660 for shaking, vibrating, or rotating the collection bottle 2610 in order to mix the specimen in the collection bottle 2610

In some embodiments, the camera module of the testing equipment can include a light field camera (not shown) that captures intensities as well as directions of the light rays. The light field camera can include an array of micro-lenses in front of an image sensor, or multi-camera arrays to detect the directional information. Using the directional information of the light rays, the camera module can capture clear images at a wide range of the focal planes. Therefore, a testing equipment using a light field camera may not need an autofocus function to fine adjust the distance between the camera module and the magnifying component.

With the above in mind, the apparatus of the present invention is useful for testing male fertility and/or female reproductivity.

The present invention provides a method for testing male fertility using the apparatus of the instant application. The method comprises the steps of: applying a biological specimen from a male subject to a first holding area and a second holding area of a carrier; inserting the carrier into the apparatus; determining the acidity of the sperm from the first analytic process; determining one or more properties of the sperm selected from the group consisting of: concentration of the sperm, motility of the sperm, and morphology of the sperm, from the second analytic process; and analyze the results to determine male fertility.

The present invention also provides a method for testing female reproductive hormones using the apparatus of the present application. The method comprises the steps of: applying a biological specimen from a female subject to a first holding area of a carrier; inserting the carrier into the apparatus; and determining the concentration level of one or more types of female hormones such as luteinizing hormone (LH), follicle stimulating hormone (FSH), or human chorionic gonadotropin (HCG).

The present invention further provides a method for testing fertility in a couple of a male subject and a female subject. The method comprises the steps of: applying a biological specimen from the male subject to a first holding area and a second holding area of a first carrier; inserting the first carrier into the apparatus; determining the acidity of the sperm from the first analytic process; determining one or more properties of the sperm selected from the group consisting of: concentration of the sperm, motility of the sperm, and morphology of the sperm, from the second analytic process; applying a biological specimen from the female subject to a holding area of a second carrier; inserting the second carrier into the apparatus; determining a concentration level of one or more types of female hormones; and analyzing the results of the male and the female biological specimen.

Figure 27:
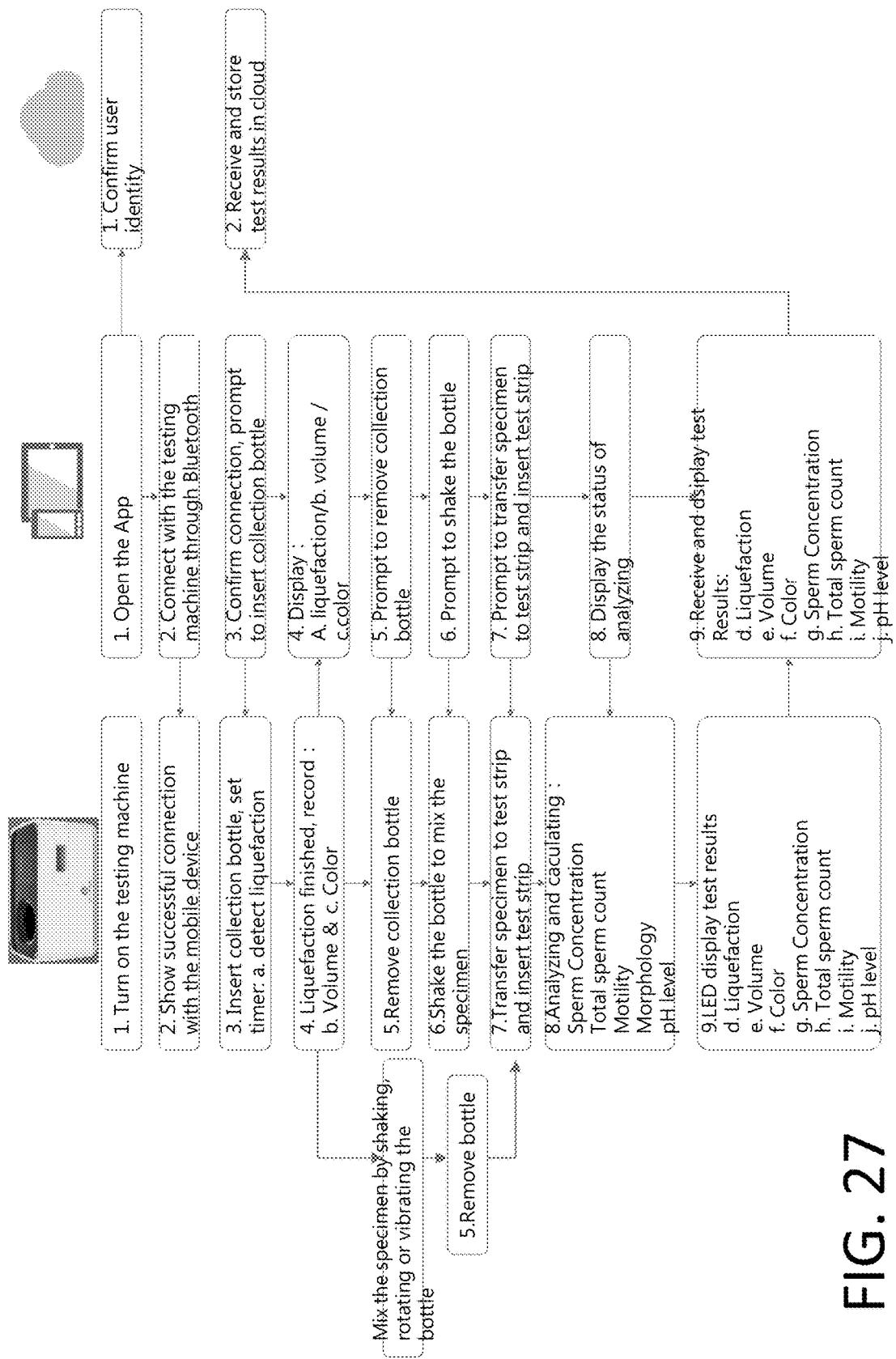
FIG. 27 is a flow chart of a process for analyzing semen specimen for male customers or patients.
Figure 28:
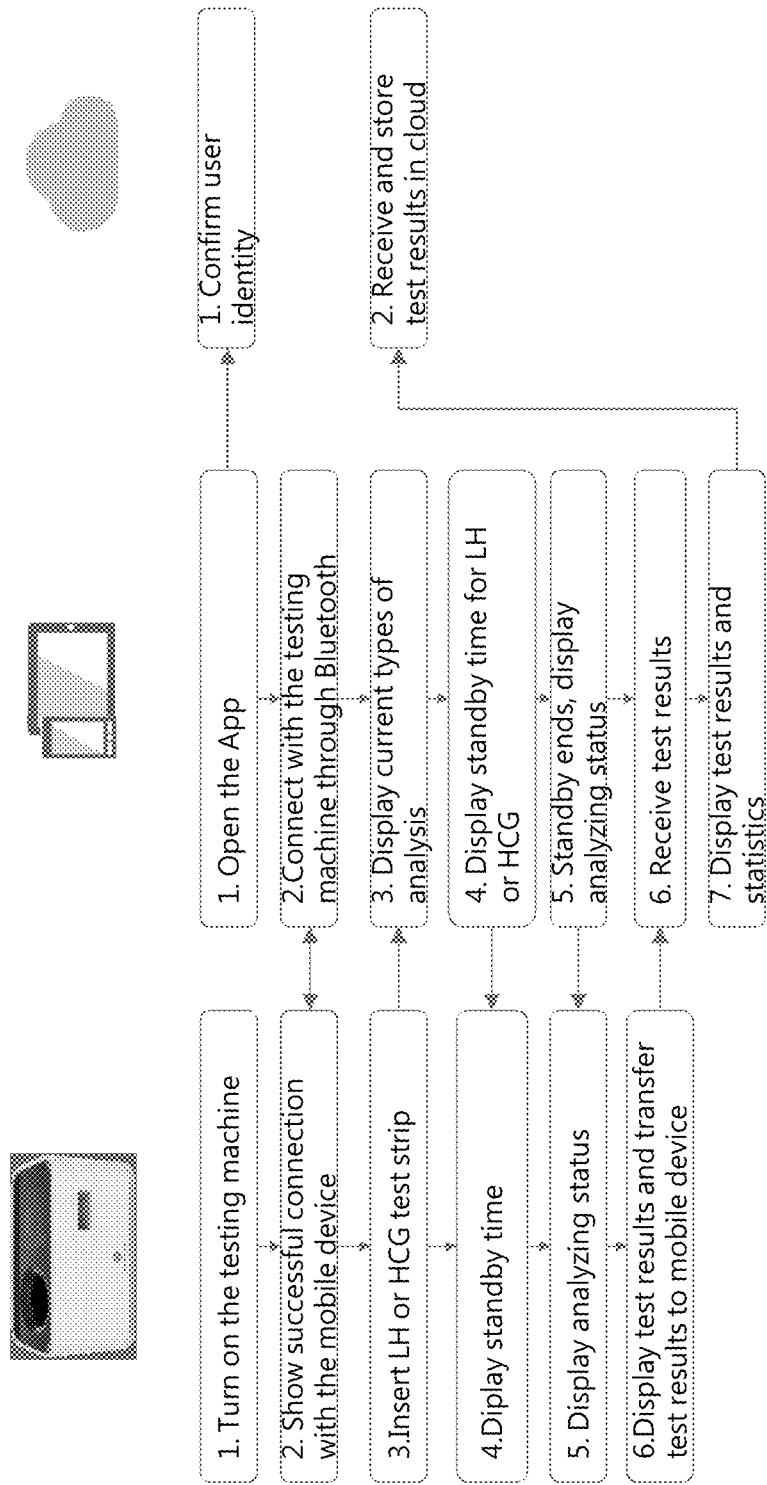
FIG. 28 is a flow chart of a process for analyzing LH or HCG for female customers or patients.

FIG. 27 is a flow chart of a process for analyzing semen specimen for male customers or patients. The system for analyzing semen specimen can include a testing machine (e.g., testing equipment 1900), a mobile device and a cloud server. FIG. 28 is a flow chart of a process for analyzing LH or HCG for female customers or patients. The system for analyzing LH or HCG can include a testing machine (e.g., testing equipment 1900), a mobile device and a cloud server. The flow charts of FIGS. 27 and 28 show steps performed by the testing machine, the mobile device and the cloud server and information being transferred among the testing machine, the mobile device and the cloud server.

In some embodiments, a method for testing sperms comprises steps of: obtaining the device for testing biological specimen; applying a sperm specimen to the specimen holding area, recording a video or an image of the sperm specimen; determining the sperm count of the sperm specimen based on the at least one frame of the recorded video or the recorded image; and determining the sperm motility of the sperm specimen based on the recorded video or the recorded image.

In a related embodiment, the method further comprises: waiting for a pre-determined time period for liquefaction of the sperm specimen before applying the sperm specimen to the specimen holding area.

In another related embodiment, the method further comprises: placing a mobile device including a camera component on top of the device such that the camera component is aligned with the magnifying component and the specimen holding area; and receiving by the mobile device light signal from the sperm specimen in the specimen holding area via magnification by the magnifying component.

In yet another related embodiment, the method further comprises: illuminating the specimen holding area by a lateral illumination device disposed on a side of the carrier of the device or a vertical illumination device disposed on top of or below the carrier of the device.

In still another related embodiment, the method further comprises: guiding light beams from the lateral illumination device throughout the carrier made of a transparent or translucent material; and reflecting the light beams to the specimen holding area by a plurality of light reflecting patterns included in the carrier.

In yet another related embodiment, the method further comprises: inserting the disposable testing device into a base, the base including a camera component for recording the video of the sperm specimen, or a form-fitting frame for securing a mobile device that includes a camera component for recording the video of the sperm specimen.

In still another related embodiment, the method further comprises: extracting at least one frame from the recorded video of the biological specimen; identifying a plurality of sperms from the at least one frame; and calculating the sperm count based on a number of identified sperms and an area recorded by the at least one frame.

In yet another related embodiment, the method further comprises: analyzing shapes of the identified sperms; and determining a morphology level based on the shapes of the identified sperms.

In still another related embodiment, the method further comprises: extracting a series of video frames from the recorded video of the sperm specimen; identifying a plurality of sperms from the series of video frames; identifying moving traces of the sperms based on the series of video frames; determining moving speeds of the sperms based on the moving traces of the sperms and a time period captured by the series of video frames; and calculating the sperm motility based on the moving speeds of the sperms.

In yet another related embodiment, the method further comprises: further magnifying the video or the image of the sperm specimen through a magnifying lens.

In some embodiments, a method for testing sperms using the system for testing biological specimen, comprises: inserting the device into the base component; recording a video of the sperm specimen in the specimen holding area by the mobile device, the mobile device being secured in the form-fitting frame of the base component; determining a sperm count of the sperm specimen based on the at least one frame of the recorded video; and determining a sperm motility of the sperm specimen based on the recorded video.

In a related embodiment, the method further comprises: further magnifying the video of the sperm specimen through a magnifying lens.

In some embodiments, a system for testing biological specimen comprises a disposable device for testing biological specimen and a base component. The disposable device includes a sample carrier including a specimen holding area, and a detachable cover placed on top of the specimen holding area. The base component includes an insertion port for inserting the disposable device into the base component, and a camera component for capturing the image of the specimen holding area, the camera component including an image sensor and an optical lens module. In a related embodiment, the optical lens module can have a linear magnification ratio of at least 0.1.

Figure 31:
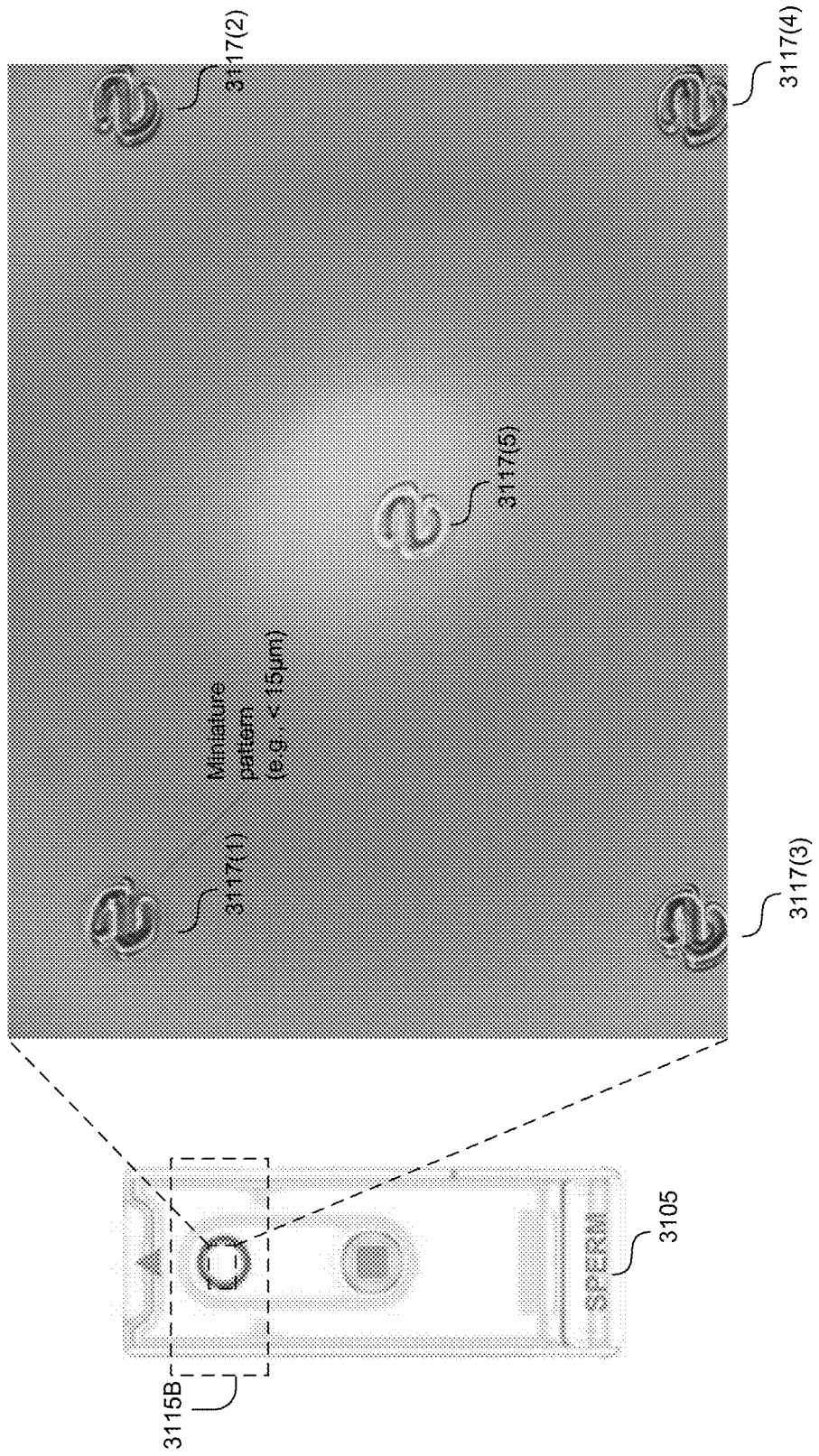
FIG. 31 shows an additional example carrier having a visual cue (e.g., in or near the holding area) that may be utilized to control the analytic process performed by the test equipment.

FIG. 31 shows an additional example carrier 3105 having one or more visual indicia 3117(1)-3117(5) (or can be referred to collectively as "visual cue" 3117) that may be utilized to control the analytic process performed by the test equipment (e.g., the test equipment shown in FIG. 21B or FIG. 22). As shown in FIG. 31, the visual cue 3117 can be in (or, in some additional or alternative embodiments, near) a holding area (e.g., holding area 3115B) on the carrier 3105.

As mentioned above (e.g., with respect to FIG. 29), the processor can perform different analytic processes based on a visual cue on the carrier. For example, some embodiments can perform image recognition and processing on the images of the holding areas and can perform different analytic processes according to a visual cue from the results of the image recognition. In some examples, the visual cue on the carrier can be a shape of a particular holding area. Additional example of the visual cue may include a graphic pattern, a visual indicium, a one-dimensional barcode, a multi-dimensional pattern code (e.g., QR code), and so forth.

In the specific example shown in FIG. 31, each of the visual indicia (e.g., visual indicium 3117(1)) can be a particular, miniature graphic pattern that can be either imprinted, attached, or otherwise marked onto the carrier 3105 in its holding area 3115B. In FIG. 31's example, the visual indicia 3117(1)-3117(5) are all of the same or substantially similar pattern; however, in other examples (not shown for simplicity), they need not be all the same, and each can have an individual shape, size, pattern, and so forth. In one or more implementations, the visual cue 3117 (i.e., the visual indicia 3117(1)-3117(5)) is of a size not perceivable by human, but can be identifiable by a camera module (e.g., camera module 2230B, FIG. 22; or camera module 2130, FIG. 21B) after magnification through a microscopic lens. In some of these implementations, the visual indicia 3117(1)-3117(5) are smaller than 15 μm. Furthermore, the visual indicia 3117(1)-3117(5) can be arranged such that their locations collectively form a pattern (i.e., a predetermined arrangement). In addition or as an alternative to the visual indicia's individual characteristics (e.g., size, shape, color, and/or location), this collective pattern formed from each visual indicium's location can be one of the identifiable cues that can be used to control the test equipment's functionality (e.g., whether and which analytic processes it subsequently performs). This collective pattern may be based on the absolute locations of the visual indicia (e.g., in the holding area) and/or relative locations of the visual indicia (e.g., from their respective neighbouring indicia). In FIG. 31, the collective pattern shown by the visual indicia 3117(1)-3117(5) is that the visual indicia 3117(1)-3117(4) each being located at one of the four corners (of the image captured by the camera) and visual indicium 3117(5) being located at the center, and that each visual indicium being relatively evenly distributed. Some additional or alternative embodiments provide that each (or each set) unique visual indicium (or indicia) in the visual cue can represent a different analytic function that is to be performed (and/or whether or not a particular analytic function is to be performed).

With the above description in mind, the test equipment disclosed here can utilize the visual cue on the carrier (e.g., in or near the holding area) to control the functionality of the test equipment and adaptively perform an analytic process based on the visual cue. In certain embodiments, the visual cue can be used to verify whether the carrier is an authorized carrier (e.g., properly licensed and manufactured within a certain specification and according to applicable qualitative standards). In another example, the visual cue can be used to control the test equipment to perform calculation in what mode (e.g., male versus female, laboratory versus home, highest precision versus shortest time, or on-battery versus plugged-in). Moreover, some embodiments provide that the visual cue can be used to control access to certain functionality of the test equipment. This can provide the capability to flexibly tailor the service(s) provided by the test equipment to a customer's identity, geographic location, and so forth.

Figure 32:
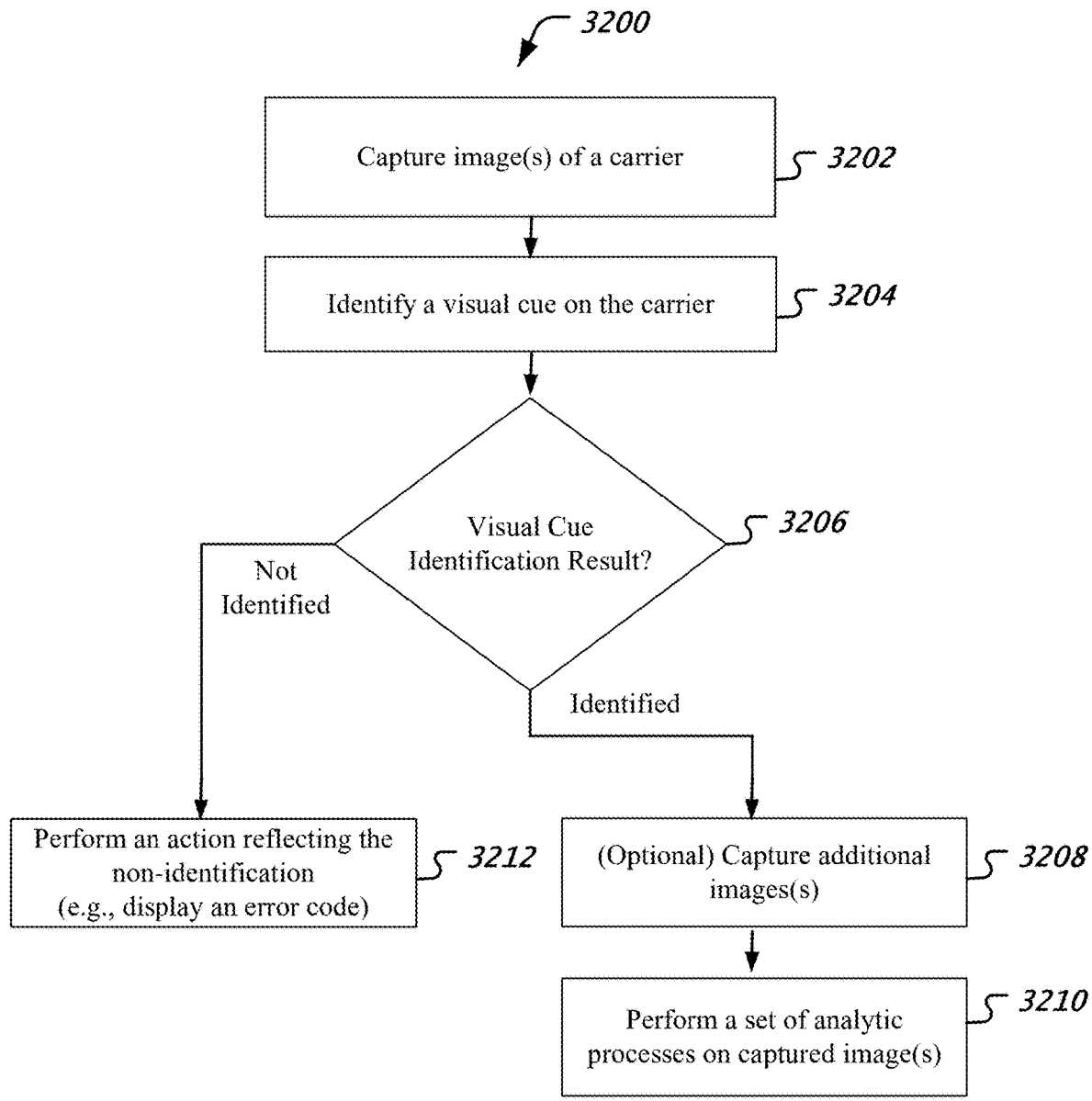
FIG. 32 is an additional example flow chart of a process which can be implemented by a test equipment disclosed here to adaptively perform an analytic process based on the visual cue.

FIG. 32 is an additional example flow chart of a process 3200 which can be implemented by a test equipment disclosed here (e.g., in FIG. 21B or FIG. 22) to adaptively perform an analytic process based on the visual cue. With continued reference to FIG. 31, the process 3200 is explained below. Note that, in the following example of the process 3200, the visual cue is applied to perform a carrier authentication application; however, the process can be adapted for performing other applications (such as those described with respect to FIG. 30) in a similar manner. For example, in a number of applications other than carrier verification, the processor can perform different sets of analytic processes based on the difference in the visual cue.

First, in step 3202, after the receiving mechanism of the test equipment receives a carrier inserted through the opening, a sensor (not shown for simplicity) can notify the processor, and the processor can cause a camera module on-board the test equipment to capture one or more images of the holding area of the carrier. In step 3204, using the captured image(s), the processor can identify (e.g., based on known image analysis techniques or those disclosed here) the visual cue in the holding area. Like discussed above, the visual cue can include a number of visual indicia. Each visual indicium may be in the same or different size, shape, pattern, color, etc (such as the example shown in FIG. 31), or they may be different. The visual indicia may altogether further present a pattern (e.g., from their locations). Then, the processor can compare the visual cue (e.g., individual size, shape, location, or collective pattern) with predetermined visual cues (e.g., stored in local memory and/or a cloud-based database (which may be operated/controlled by the test equipment's manufacturer or another administrator)).

In step 3206, the processor selectively performs a set of analytic processes on the captured images of the holding area, based on a result of said identification of the visual cue. If the identification result of visual cue returns positive (e.g., in response to that the holding area of the carrier has the predetermined visual cue), then the processor proceeds with subsequent steps, which may include optionally capturing more images (or a video) for the analysis (Step 3208) and performing the corresponding set of analytic processes on the captured image(s) (Step 3210). On the other hand, if the identification result of the visual cue returns negative (e.g., in response to that the holding area of the carrier does not have the predetermined visual cue), then the processor causes an alternative action (e.g., displaying an error code) reflecting the non-identification of the visual cue, and does not perform any analytic processes on the image(s) (Step 3212). After said set of analytic processes is performed, the processor can continue to determine an outcome with regard to the biological specimen based on results from the analytic processes, as described above.

Furthermore, it is noted here that conventional computer-assisted sperm analyzers (CASA) rely on large microscopes and the experience of the operating technicians for determining sperm parameters. There are some computer software aids available to supplement the experience of the technician and to standardize the analysis results. However, due to the differences in lens and sensor modules, often times blurry images may adversely affect the effectiveness of the software aid, resulting in inaccuracy in related functions (e.g., sperm count calculation).

In addition, regulatory bodies such as World Health Organization (WHO) publishes a laboratory manual for the examination and processing of human semen. The manual specifies that a minimum amount of samples to be evaluated (e.g., 200 sperms) for the determination of sperm concentration, sperm motility and sperm morphology. Existing CASA-based image analysis generally either lacks automated sampling or requires manual operation to acquire multiple field of view in order to achieve WHO specification and to reduce sampling error in the analysis; alternatively, if sampling is only repeatedly performed with a single field of view, the time it takes to repeat the process in order to reach a satisfactorily low sampling error often becomes too long to be feasible in large scale.

Figure 33:
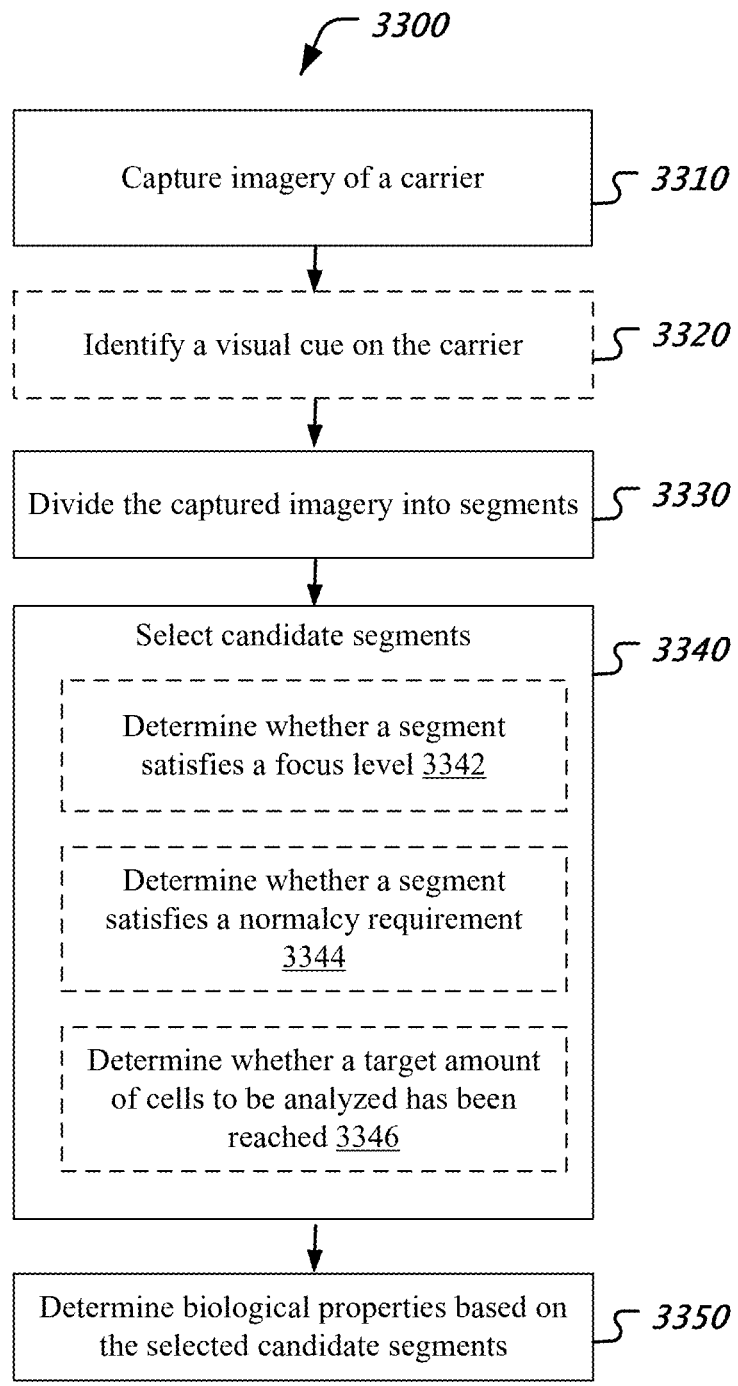
FIG. 33 is an example flow chart of a process which can be implemented by a test equipment disclosed here.

FIG. 33 is an example flow chart of a process 3300 which can be implemented by a test equipment disclosed here (e.g., in FIG. 21B or FIG. 22) for improved results (e.g., with increased analysis accuracy and efficiency). The process 3300 can be an alternative or a supplemental process to the processes disclosed here, e.g., the process illustrated in FIG. 16.

First, at step 3310 (for example, after the carrier cartridge that carries or has been exposed to biological specimen is inserted (introduced above)), the introduced device(s) can utilize the camera module(s) to capture one or more images (or collectively, "imagery") of the carrier cartridge's holding area(s). In some optional embodiments (e.g., those described with respect to FIG. 29 or 31), the device can identify (step 3320), from the captured imagery of the holding area, a visual cue on the carrier. In these optional embodiments, the device can perform, based on a result of said identification of the visual cue, a set of analytic processes on the captured imagery.

Figure 34:
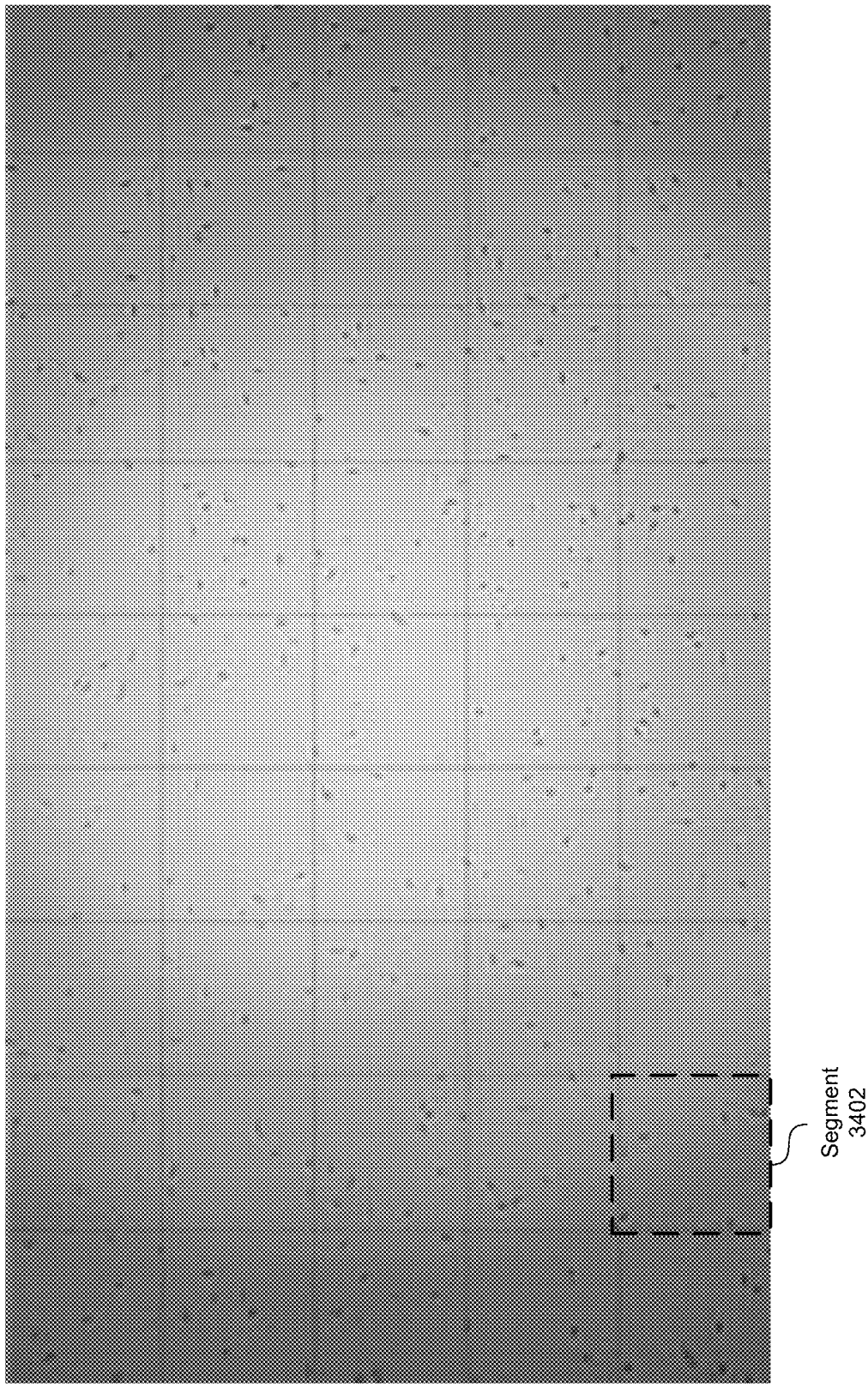
FIG. 34 is an example image of a holding area divided into a number of segments.

At step 3330, the device can divide the captured imagery into a plurality of segments. In some embodiments, the segments can be polygonal in shape. More specifically, some implementations provide that the segments can be in shape of triangle, rectangle, square, pentagon, hexagon, and so forth. The shapes (of the segments) may have at least one side that is 0.05 mm. In one or more embodiments, the segments are square and are of size of 0.05 mm×0.05 mm. It is noted that, depending on the specific implementation, the number and size of the segments can be adjusted based on the resolution of the camera module. Illustrated in FIG. 34 is an example image of a holding area divided into a number of segments (e.g., segment 3402). Note that, for facilitating the discussion of the disclosed technique here, the captured imagery is said to be "divided" into segments; however, it should be understood that, in one or more implementations, the processor need not actually perform a mathematical divisional operation at run time (or during normal operation) in order to perform this technique; rather, the resulting segments or grids can be predetermined, logically prewired, programmed or otherwise preconfigured into the device's camera controller and/or processor, such that the need for performing calculations associated with the division of imagery into segments may be reduced or, in some examples, completely eliminated.

At step 3340, the example device selects, from the plurality of segments, candidate segments for analysis. According to one or more embodiments, the selecting of candidate segments can be based on a number of factors including, for example, a focus level of a given segment, and/or a normalcy of the given segment.

More specifically, in a number of implementations, the device can determine (3342) a focus level for each of the plurality of segments, so that each segment may have a corresponding focus level measurement. The focus level can be determined based on one or more focus measure functions. Depending on the implementation, the adopted focus measure functions can include one or more of: a variance type, a sum-modulus-difference type, an energy of Laplacian of image type, and/or a gradient magnitude maximization type.

After determining each segment's focus level, in some embodiments, the device then compares the focus level of a given segment against a minimum focus level threshold. In one or more implementations, a given segment can be selected as a candidate segment only if the focus level of the given segment satisfies (e.g., reaches, or exceeds) the minimum focus level threshold. Additionally, the device can label or number the segments. One or more embodiments of the device provide that only the segments that satisfy the minimum focus level threshold are labeled or numbered (e.g., for purposes of further analysis or tracking identification). The labeling or numbering can be done sequentially or randomly. Illustrated in FIG. 35 is a portion of a candidate segment selection process, where the segments are numbered randomly, and with segments passing the minimum focus level threshold preliminarily selected as candidate segments 3510.

Next, the device can perform image processing to a number of selected segments to determine a property of the selected segments so as to determine (3344) a normalcy for a given segment, i.e., to see if the given segment is "normal enough" to warrant further analysis. In some examples, the segments selected for normalcy determination are those have been preliminarily selected as candidate segments (e.g., those that satisfy the minimum focus level threshold, discussed above). In some examples, the property to be used for normalcy determination at this stage is cell count (e.g., sperm count). In a more specific example, the device can perform image processing onto those segments having focus levels satisfying the minimum focus level (meaning that they are "focused enough") to determine, for each enough-focused segment, a cell (e.g., sperm) count in that segment. The image processing can include binarization (and in some implementations, with adaptive thresholding) to identify portions in the segment with objects that may be sperms as foreground, and to identify the rest of the segment as background. After the image processing, the device can determine the cell (e.g., sperm) count. In one or more embodiments, the cell count of a candidate segment can be determined based on a ratio between the area with sperm and the area without sperm (e.g., by extrapolation from a table that correlates ratios with known cell counts).

Figure 36:
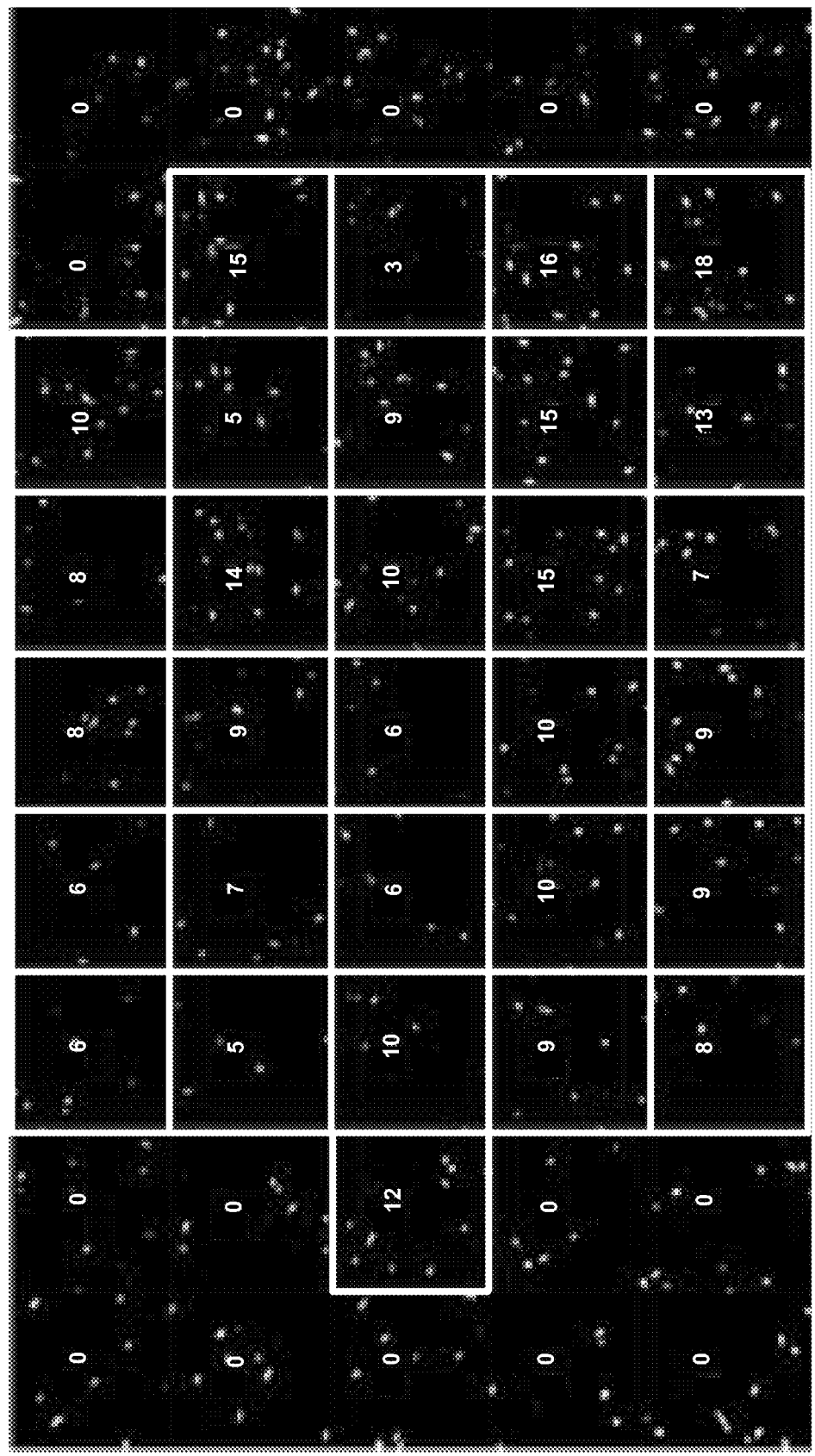
FIG. 36 is an example image illustrating results after image processing (e.g., binarization) and cell count determination.

Thereafter, the device can calculate statistical data (e.g., a mean value and a standard deviation) for all remaining candidate segments (e.g., those segments that satisfy the minimum focused level). With the statistical data calculated, the device can determine (3344) the normalcy of a given segment by statistically comparing one or more properties (e.g., the sperm count) of the given segment against all remaining candidate segments. In some embodiments, a given segment continues to be selected as candidate segment only if the normalcy of the given segment satisfies a normalcy requirement. Take sperm count as an example, in a number of embodiments, the segment is considered "normal enough" (i.e., satisfying the normalcy requirement) if the sperm count within the segment is within, from the mean value, a predetermined number of standard deviations of the plurality of segments. In one or more implementations, the normalcy requirement is within two (2) standard deviations (from the mean value). In other implementations, the normalcy requirement can be one (1) or three (3) standard deviations, or other suitable statistical techniques that reflect a given segment's normalcy in comparison with a group of segments. Illustrated in FIG. 36 is an example image showing results after image processing (e.g., adaptive thresholding binarization) and cell count determination. Note that, in FIG. 36, the estimated cell count for each candidate segment is shown in lieu of its label.

Additionally, the device can determine (3346) whether a target amount of cells to be analyzed has been reached or not. Specifically, one or more embodiments of the disclosed device can maintain a total cell count, and for each segment that is selected into the candidate segments, the device adds a corresponding cell count of the segment to the total cell count. The device can use this target amount of cells to be analyzed to control an amount of biological samples to be analyzed, and depending on the implementation, the number can be configurable. This number can tailored to laboratory manual and testing standards for testing a particular biological specimen. In some embodiments, the target amount of cells to be analyzed is two hundred (200). In certain examples, the selecting of candidate segments completes when the total cell count reaches the target amount of cells to be analyzed. In other words, according to at least some embodiments disclosed here, the selecting of candidate segments can be performed (e.g., in a random manner) on segments that satisfy a focus level threshold and a normalcy requirement until a total cell count reaches a target amount of cells to be analyzed.

As step 3350, after selecting the candidate segments, the introduced device can determine one or more properties of the biological specimen by analyzing the selected candidate segments (e.g., by using one or more techniques introduced here). In at least a number of embodiments, the biological specimen is semen, and the one or more properties of the biological specimen that are to be determined on the selected candidate segments include one or more of: cell count (or concentration, which can be inferred from the cell count), motility, or morphology. In some examples, the device is further configured to, after said set of analytic processes is performed, determine an outcome (e.g., fertility) with regard to the biological specimen based on results from the analytic processes.

Furthermore, it is observed here that it is generally difficult to perfectly manufacture a lens assembly (especially in large quantity and with controlled cost) such as the microscopic lens assembly and/or the magnifying lens assembly that are installed on the test equipment introduced here. Lens defects can exist in a variety of forms, such as impurity, or imperfections in lens characteristics (e.g., clarity, refractivity, focal points, among others), and these defects can adversely affect the accuracy of the test equipment. Introduced here, therefore, are calibration and validation techniques to mitigate lens defects and to further improve analysis accuracy of test equipment disclosed herein.

Figure 37:
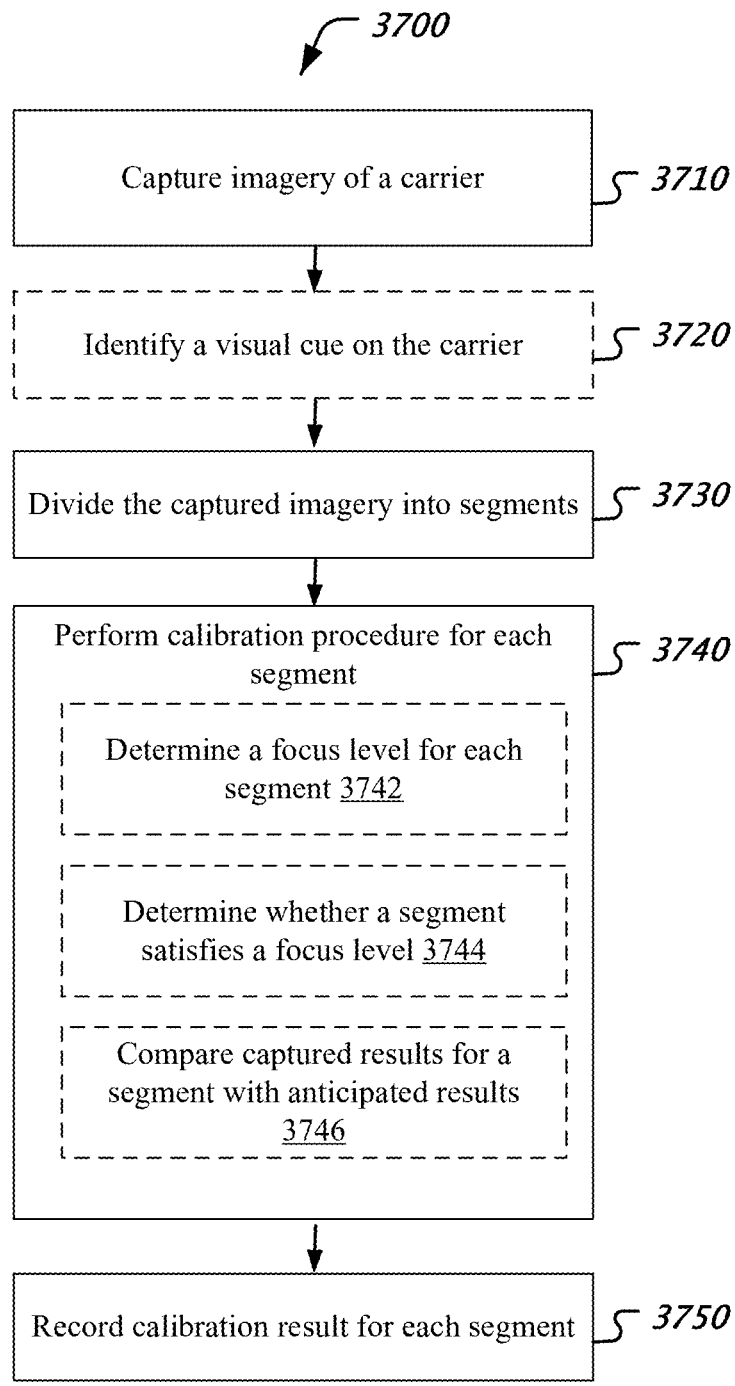
FIG. 37 is an example flow chart of a calibration process which can be implemented by a test equipment disclosed here.

FIG. 37 is an example flow chart of a calibration process 3700 which can be implemented by a test equipment disclosed here (e.g., in FIG. 21B or FIG. 22) for improved results. The process 3700 can be an alternative or a supplemental process to the processes disclosed here, e.g., the process illustrated in FIG. 16.

First, at step 3710 (for example, after a carrier cartridge is inserted), the introduced device(s) can utilize the camera module(s) to capture one or more images (or collectively, "imagery") of the carrier cartridge's holding area(s). In some optional embodiments (e.g., those described with respect to FIG. 29 or 31), the device can identify (step 3720), from the captured imagery of the holding area, a visual cue on the carrier. In these optional embodiments, the device can perform, based on a result of said identification of the visual cue, a set of analytic processes on the captured imagery.

More specifically, in some implementations, the carrier cartridge here can be a specialized dummy cartridge that can be used to trigger the calibration process. For example, a specialized dummy cartridge may carry one or more of the specialized graphic patterns (e.g., introduced below with respect to FIG. 38) which, after the visual cue identification process (e.g., in Step 3720), can trigger the test equipment to enter a calibration mode. For another example, a specialized dummy cartridge can carry specialized test samples (e.g., introduced below with respect to FIG. 41), and the user can manually cause (e.g., via a user interface onboard or remotely controlling the test equipment) the test equipment to enter a calibration mode. In various examples, the dummy cartridge can include an electronic (e.g., an radio-frequency identifier (RFID)) or a mechanical feature (e.g., a special shape or a mechanical protrusion) that can trigger the calibration mode.

Figure 38:
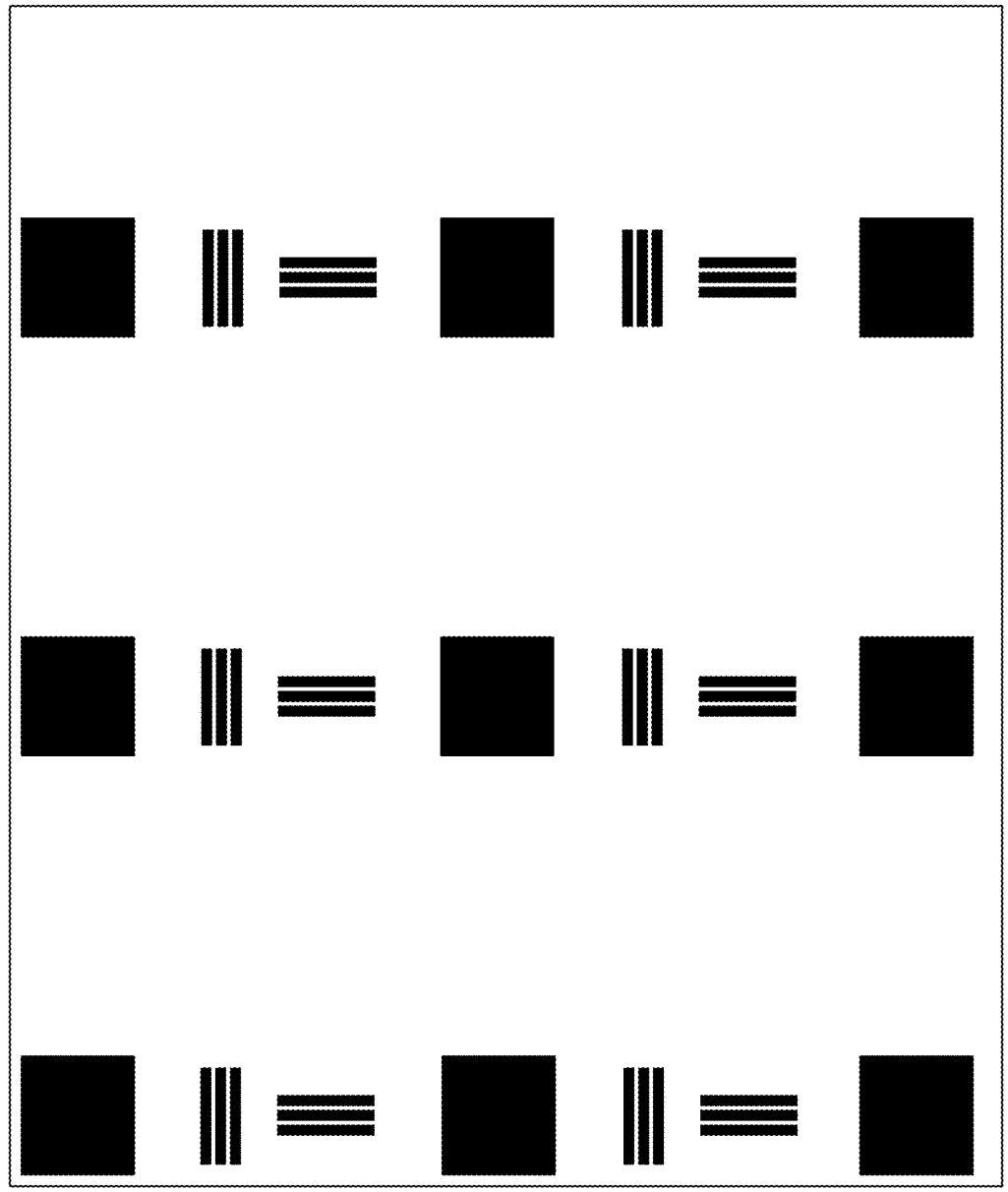
FIG. 38 is a test carrier carrying a visual cue and/or an image pattern that can be used to calibrate or validate a test equipment disclosed here.

FIG. 38 is a test carrier carrying a visual cue or an image pattern that can be used to calibrate or validate a test equipment disclosed here. In one or more embodiments, the visual cue contains an image pattern that the test equipment can recognize as a trigger to enter calibration mode. Thereafter, the test equipment can utilize the camera modules to capture images of the image pattern and to perform self-diagnosis in order to calibrate itself from the results of the captured images. The visual pattern should be easy to identify (and less likely to misidentify). As illustrated in FIG. 38, the example visual pattern contains a repeating (e.g., every 0.08 mm; also known as rate of repetition or "pitch"), larger (e.g., 0.02 mm×0.02 mm), and generally regular shape (e.g., square). The visual pattern can further contain one or more repeating linear patterns. In the illustrated example in FIG. 38, the linear patterns include a set of (e.g., three) horizontal lines and a set of (e.g., three) vertical lines. In some embodiments, these lines have a resolution of 200 line pairs per millimeter (LP/mm) or higher. In the particular example in FIG. 38, the lines have a resolution of 500 LP/mm. Note that horizontal and/or vertical lines are examples of visual linear patterns suitable for aiding the test equipment to perform self-diagnosis of optical characteristics and performance of the specific optical instruments (e.g., microscopic lens) installed onto the test equipment itself; other visual patterns that are suitable may substitute the illustrated example in FIG. 38. For example, in some embodiments, an "E" shape pattern or equivalents can used as the visual linear pattern in lieu of the parallel lines. For example, in some embodiments, Sagittal lines and Meridional lines can used as the visual linear pattern.

Continuing with the process 3700, regardless how the calibration mode is triggered, at Step 3730, after imagery of the carrier is captured (e.g., at Step 3710), the device can divide the captured imagery into a plurality of segments (which is similar to Step 3330, discussed above). In some embodiments, the segments can be polygonal in shape. More specifically, some implementations provide that the segments can be in shape of triangle, rectangle, square, pentagon, hexagon, and so forth. The shapes (of the segments) may have at least one side that is 0.05 mm. In one or more embodiments, the segments are square and are of size of 0.05 mm×0.05 mm. It is noted that, depending on the specific implementation, the number and size of the segments can be adjusted based on the resolution of the camera module. In one or more implementations, the above-mentioned pitch (i.e., the rate at which the visual pattern regularly repeats itself) can correspond to the number of segments that the imagery can be divided. In some embodiments, the pitch can be the same as the number of segments that the imagery can be divided by the test equipment.

At step 3740, the example device can perform the calibration/self-diagnosis procedure, e.g., for each segment. The calibration procedure should generally be one or more steps that can enable the test equipment to autonomously self-diagnose the quality of the optical modules (e.g., including microscopic lens, camera modules) that are currently installed onto the test equipment itself. In one or more embodiments, the test equipment can determine (at Step 3742) a focus level for each segment, for example, by using one or more focus measure functions. Examples of focus measure functions can include a variance type, a sum-modulus-difference type, an energy of Laplacian of image type, and/or a gradient magnitude maximization type. Then, at Step 3744, the test equipment can determine whether a segment satisfies a focus level, e.g., the minimum focus level threshold discussed above. Additionally or alternatively, the test equipment can compare (at Step 3746) captured results with one or more anticipated results. For example, the test equipment's processor can access one or more images pre-installed (i.e., not captured by camera, e.g., installed by being transferred or otherwise programmed) in the memory, compare that with the captured image, and determine whether the captured image quality in the segment in question satisfies a minimum standard. The one or more images that are pre-installed should be representative of the visual patterns being applied for calibration. Example image quality parameters that the test equipment can be comparing and inspecting at Step 3746 can include color distortion, pattern distortion, clarity defects, and/or other image defects.

Figure 39:
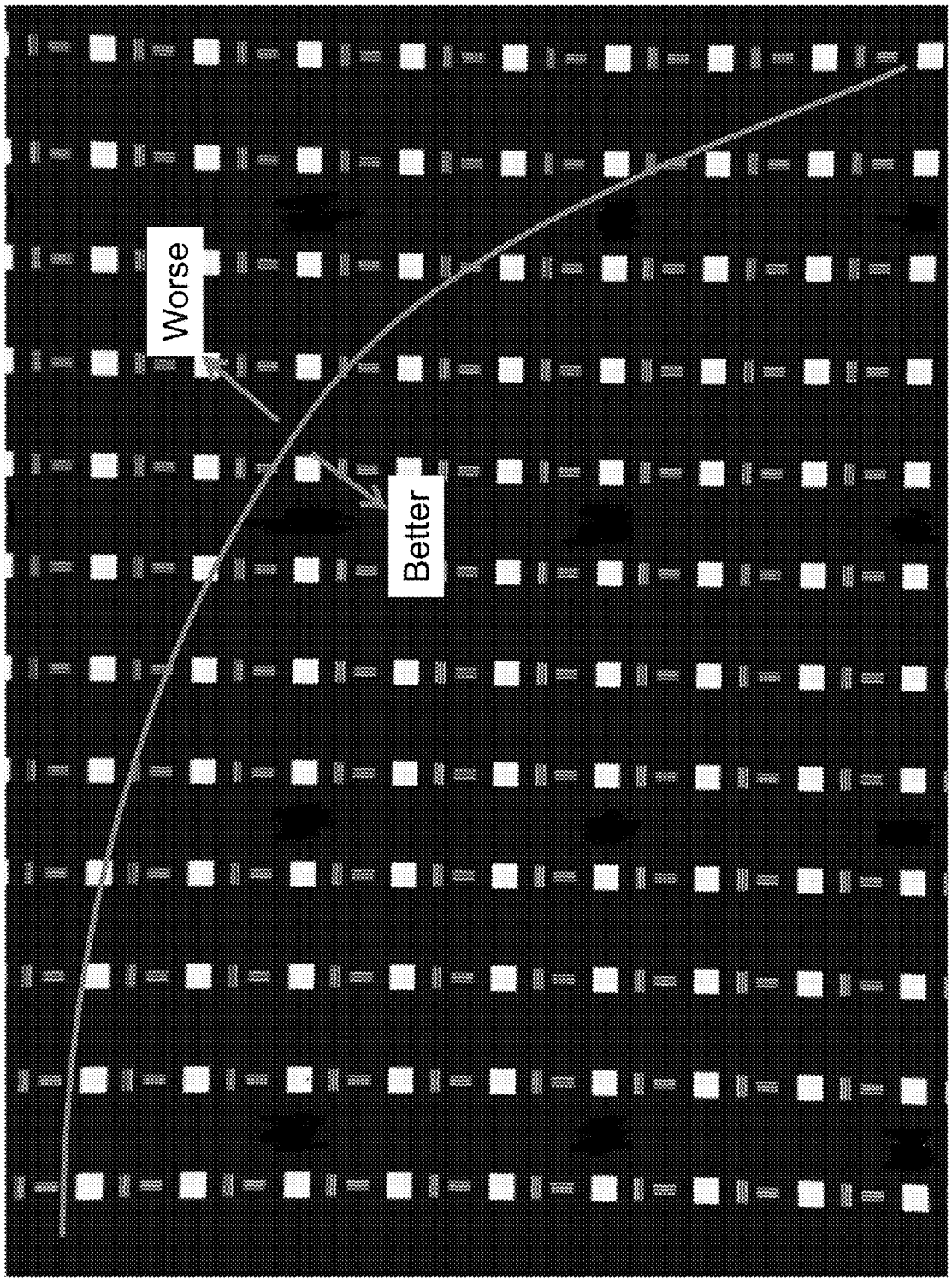
FIG. 39 is an example image of the visual cue example of FIG. 38, captured by a test equipment such as disclosed here.
Figure 40B:
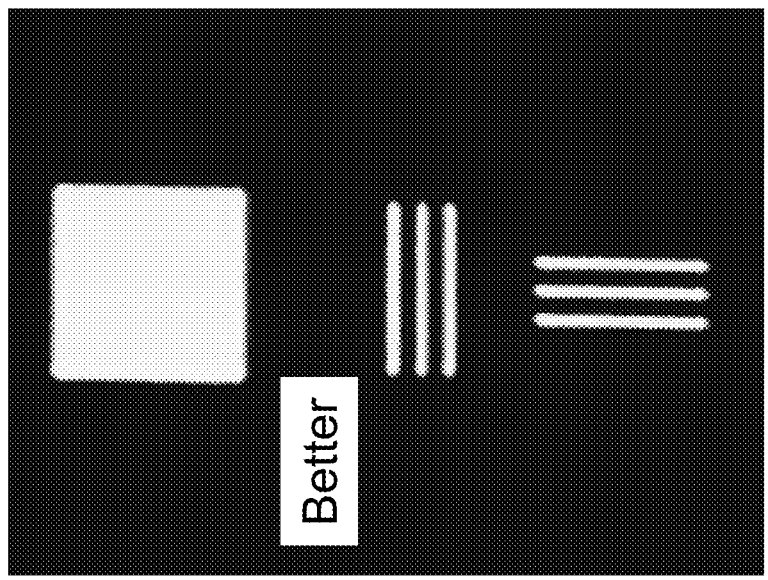
FIGS. 40A and 40B illustrate different image quality in different segments of the captured image in FIG. 39.
Figure 40A:
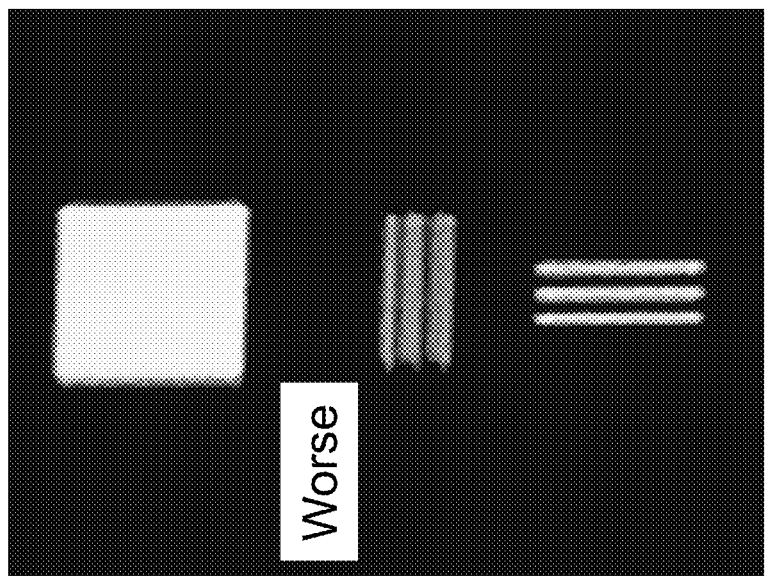

FIG. 39 is an example image of the visual cue example of FIG. 38, captured by a test equipment such as disclosed here, where the image quality is generally better toward the lower-left corner, worse toward the upper-right corner. FIGS. 40A and 40B are two specific examples illustrating different image quality in different segments of the captured image in FIG. 39. In some embodiments, e.g., those examples where the pitch is the same as the number of segments that the imagery can be divided, FIGS. 40A and 40B can respectively represent a segment. As illustrated, the image quality in the segment in FIG. 40A is better than the segment in FIG. 40B, because the image is sharper and better focused.

Referring back to the process 3700, at Step 3750, the results from Step 3740 (e.g., whether or not a segment satisfies minimum image quality requirements, such as a minimum focus level) are recorded in a computer readable storage medium (e.g., which can be non-transitory, such as flash memory) coupled to the test equipment (not illustrated for simplicity). This knowledge gained from the calibration procedure can be utilized, for example, later when the test equipment is in normal operation. In one or more embodiments, during normal operation (e.g., during Step 3340, discussed above), the test equipment can automatically skip or ignore those segments that have failed the minimum image quality requirement during calibration/self-diagnosis. In this way, the test equipment disclosed here can mitigate the adverse effect from lens defects and improve analysis accuracy.

FIG. 41 is an example image of a test carrier carrying a test sample that can be used to calibrate or validate a test equipment disclosed here. This technique can be applicable to one or more aforementioned embodiments where a specialized dummy cartridge can carry specialized test samples and the calibration mode can be initiated by triggers other than visual pattern (such as manual initiation by the user, or by a mechanical feature or an RFID on the dummy cartridge). A certain number of embodiments provide that the test sample be in the form of an aqueous medium (e.g., a liquid solution) that contains miniature test particles, such as test particles 4102 illustrated in FIG. 41. These microparticles can be made of any suitable materials including, for example, polymer. One particular example material for particles 4102 is latex. The size of the particles can be suited for a particular application. In certain implementations, the size of particles can be similar to those of a cell, such as a sperm. Example range of the particle's size can be from 0.5 µm to 50 µm in diameter. In one example, the particles are 5 µm in diameter. With the test particles as samples, the test equipment can perform calibration/self-diagnosis such as the process 3700 discussed here without Step 3720, and self-diagnose the quality of the optical modules that are currently installed onto itself. In some of these implementations, the test equipment can have images of the test particles pre-installed (i.e., not captured by camera, e.g., installed by being transferred or otherwise programmed) in the memory for comparison and calibration purposes, such as discussed above.

FIGS. 42A and 42B illustrate different image quality in different segments of the captured image in FIG. 41. As illustrated, the image quality in the segment in FIG. 42A is better than the segment in FIG. 42B, because the image is sharper and better focused. Similar to what is discussed above with respect to Step 3750, the knowledge of each segment's baseline image quality can be utilized, for example, later when the test equipment is in normal operation. For example, some embodiments of the test equipment can automatically skip or ignore those segments that have failed the minimum image quality requirement during calibration/self-diagnosis. In this way, the test equipment disclosed here can mitigate the adverse effect from lens defects and improve analysis accuracy.

Figure 43:
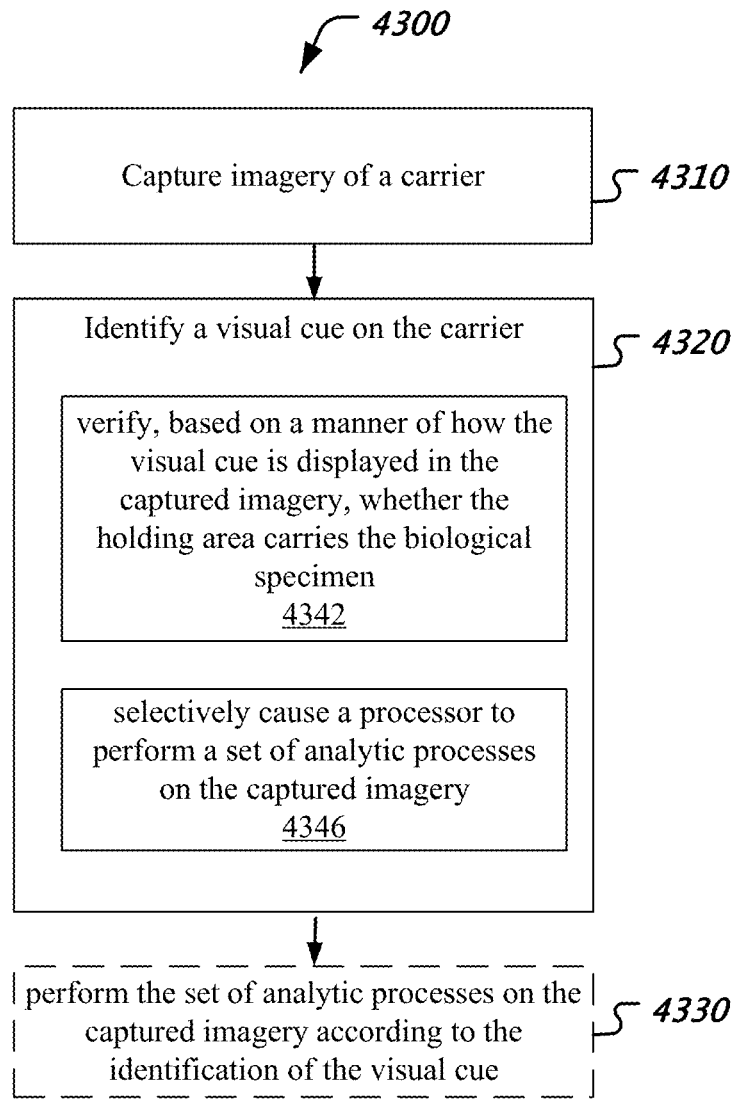
FIG. 43 is an example flow chart of a process that can be implemented by a test equipment disclosed herein to verify that the specimen holding area carries a biological specimen.

In some embodiments, the visual cue (e.g., as discussed in connection with FIG. 31) can help the testing equipment determine a condition of the carrier or the specimen holding area (e.g., whether the area is dry or wet, or carries a good sample of specimen). FIG. 43 is an example flow chart of a process 4300 that can be implemented by a testing equipment disclosed herein (e.g., in FIG. 21B or FIG. 22) to verify that the specimen holding area carries a biological specimen.

At step 4310 (for example, after the carrier cartridge is inserted), the device(s) can utilize the camera module(s) to capture one or more images (or collectively, "imagery") of the carrier cartridge's holding area(s). At step 4320, the device can identify, from the captured imagery of the holding area, a visual cue on the carrier. The identification of the visual includes, at step 4342, verifying, based on a manner of how the visual cue is displayed in the captured imagery, whether the holding area carries the biological specimen. The identification further includes, at step 4344, selectively causing the processor to perform the set of analytic processes on the captured imagery depending on a result of said verifying. At step 4330, the device can perform the set of analytic processes on the captured imagery according to the identification of the visual cue.

Figure 44B:
FIG. 44B illustrates another example of a captured image of an empty or dry specimen holding area.
Figure 44A:
FIG. 44A illustrates an example of a captured image of an empty or dry specimen holding area.
Figure 45B:
FIG. 45B illustrates another example of a captured image of a specimen holding area that holds a fluid carrying a biological specimen.
Figure 45A:
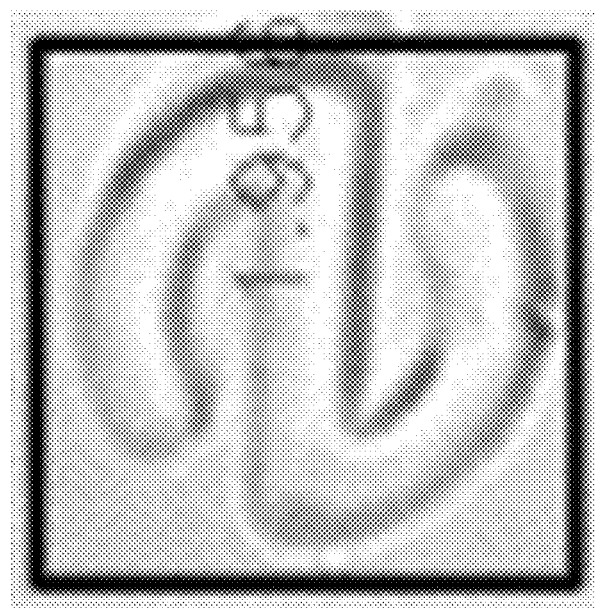
FIG. 45A illustrates an example of a captured image of a specimen holding area that holds a fluid carrying a biological specimen.

FIGS. 44A-B show examples of captured imagery of an empty or dry specimen holding area. FIGS. 45A-B show examples of captured imagery of a specimen holding area that holds a fluid carrying a biological specimen. In these specific examples, each captured image shows a visual indicium of a miniature graphic pattern. The shadow of the visual indicium is clearly visible in the empty or try specimen holding area. The fluid that carries the biological specimen can cause the specimen holding area to exhibit a different refractive index as compared to the refractive index of an empty carrier cartridge, thereby affecting the captured shape of the visual indicium. The shadow of the visual indicium can thus fade due to the refraction. For example, the captured shape of the visual indicium with biological specimen (e.g., FIGS. 45A-B) can be optically distorted as compared to a template (e.g., the captured shape of the visual indicium without any specimen such as shown in FIGS. 44A-B). Thus, by comparing the captured shape of the visual indicium against the template and evaluating the degree of distortion, e.g., determining the thickness of the indicium boundaries, or the shadow areas, etc., the processor can determine whether the specimen holding area actually holds a biological specimen for examination. Here, the distortion threshold represents a degree of optical distortion indicating an existence of the biological specimen in the holding area. In particular, the degree of distortion can be compared against a predefined threshold to verify whether the carrier carries a biological specimen. In various implementations, different thresholds can be defined based on the adopted algorithms and/or heuristics. For example, algorithms such as pixel gradient direction and intensity detection can be used to determine the corresponding threshold(s).

In some implementations, the template can be created by capturing an image of an empty carrier cartridge in a configuration stage before examining any biological specimen and storing the image(s) data representing the visual cue from the captured image. In some implementations, the template can be stored in the device to reduce the number of operations to be performed in the configuration stage. In some embodiments, the visual cue can be compared against the stored images to determine a difference between the two. When the different is below a predetermined threshold, the processor can determine that the holding area carries the biological specimen.

If the processor verifies that the specimen holding area carries a valid specimen, the process proceeds to analyzing the captured image. However, if the processor fails to verify that the specimen holding area carries any valid (e.g., not fluid when the analytic task at hand (e.g., which in some examples may recognized by a shape of the holding area, described above) calls for a fluid sample) biological specimen based on the comparison, the processor does not proceed to any image analysis. Instead, in some implementations, the device notifies the user that an invalid sample has been provided. The notification can be displayed as a signal or a label indicating that no biological specimen has been provided.

In some cases, as discussed above, existing CASA-based image analysis generally either lacks automated sampling or requires manual image post-processing to acquire multiple fields of view in order to achieve the WHO specification. To address this problem, the testing equipment can include a positioning mechanism operable to adjust a relative location of the carrier to the camera, with or without human intervention, such that images can be taken with multiple adjacent fields of view.

Figure 48:
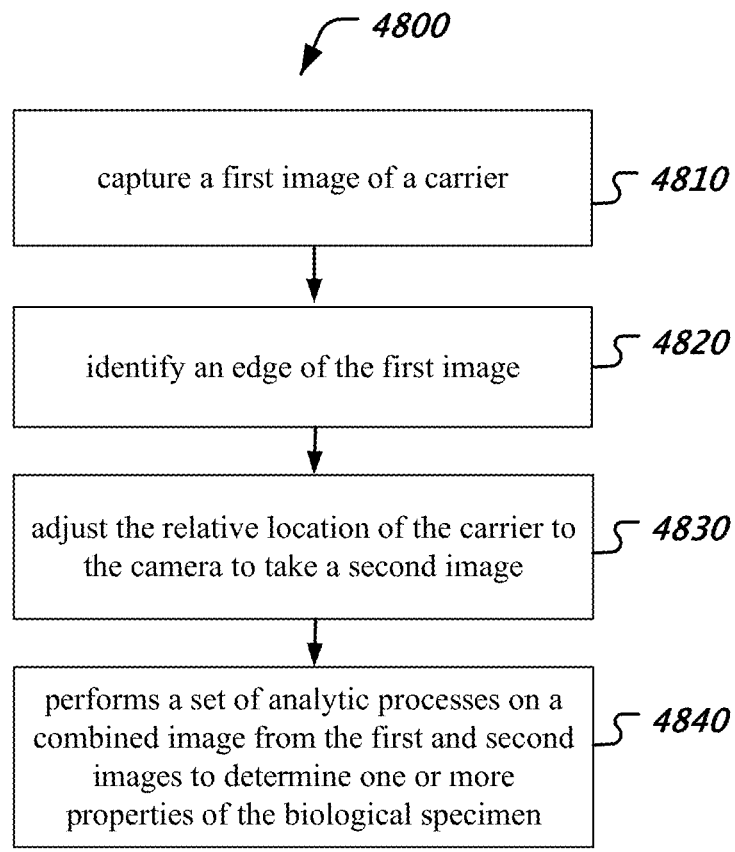
FIG. 48 is an example flow chart of a process that can be implemented by a testing equipment disclosed here for improved results using multiple fields of views.

FIG. 48 is an example flow chart of a process 4800 that can be implemented by a testing equipment disclosed here for improved results using multiple fields of views. At step 4810, e.g., after the carrier cartridge is inserted, the device(s) can use the camera module(s) to capture a first image of the specimen holding area of the carrier. At step 4820, the device identifies an edge of the first image. The positioning mechanism of the device adjusts, at step 4830, the relative location of the carrier to the camera (by adjusting the carrier, the camera, or both) such that, when the camera takes the second image, an edge of the second image is adjacent to or aligns with the identified edge of the first image. At step 4840, the device performs a set of analytic processes on a combined image from the first and second images to determine one or more properties of the biological specimen (e.g., a cell count). In some implementations, when the edge of the second image aligns with the edge of the first images, the two images can be used to composite a larger image. In some embodiments, the first and second images simply form different views. The second image can be located close to the first image or be positioned randomly so long as the second image does not overlap with the first image.

In some embodiments, the positioning mechanism can determine multiple fixed positions of the camera. In some embodiments, the positioning mechanism can determine multiple positions of the carriers. For example, a multi-axis mobile platform shown in FIG. 49 can be used to adjust carrier positions and/or the camera position.

In some embodiments, multiple markers (e.g., visual cues as shown in FIG. 31) can be positioned on the testing equipment (e.g., placed on the mobile platform) so that the camera can detect them. After the camera locates a marker, the camera uses the marker as a starting point to begin scanning. The remaining markers provide a guidance for the scanning path of the camera, thereby allowing the test equipment to adjust the camera to the fixed positions automatically to capture images of multiple views. The scanning path following the markers can be random so long as no area is repeatedly scanned. The scanning path can also follow a sequential order (e.g., clockwise or counterclockwise). For examples, four markers can be used to mark four corresponding areas. The camera can follow the markers sequentially or randomly to capture each of the areas without repetition. In some embodiments, the multiple axes 4901 of the platform allows the adjustment of the carrier and/or camera manually or automatically in x, y, and directions of the carrier plane.

Figure 50A:
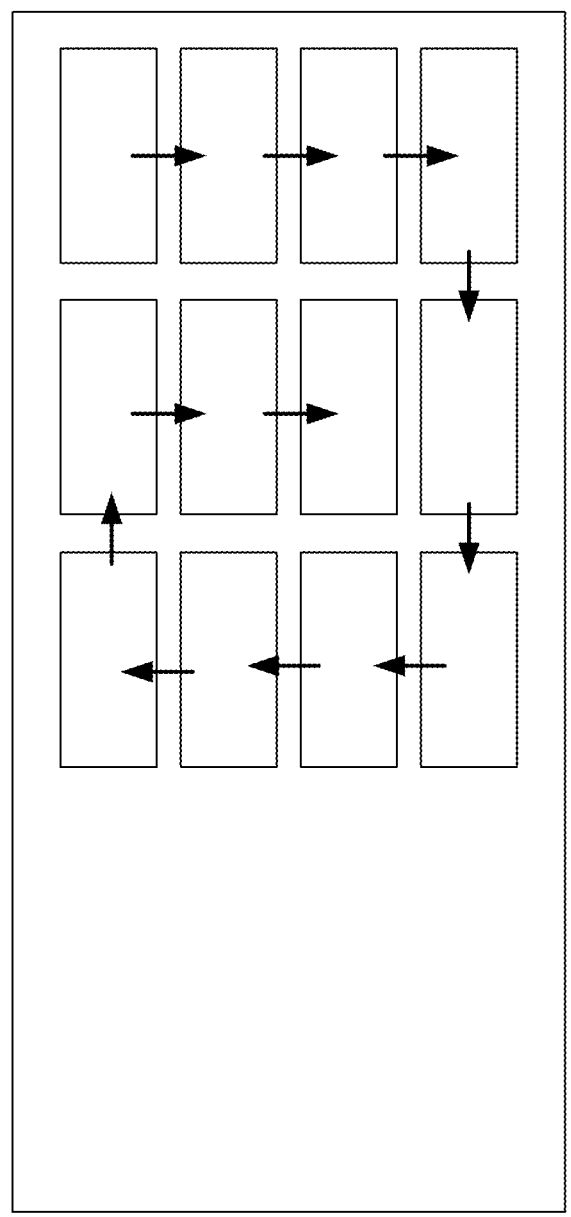
FIG. 50A shows an example manner of taking images sequentially in a clockwise order viewed from the camera.
Figure 50B:
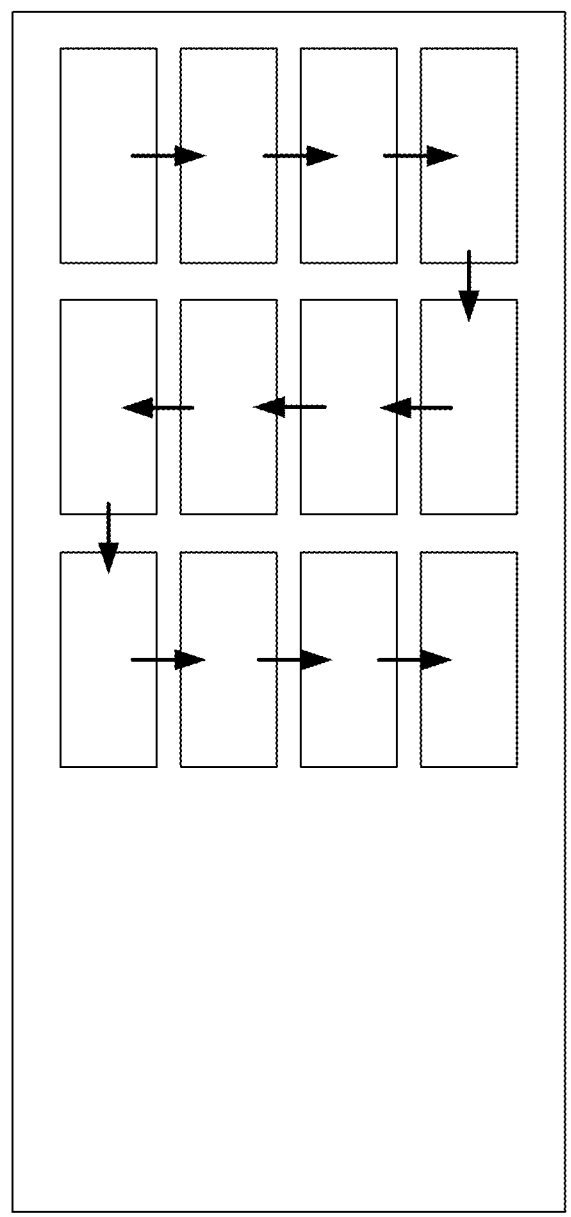
FIG. 50B shows an example manner of taking images sequentially in a progressive scan order.

In some embodiments, the positioning mechanism adjusts the relative location of the carrier to the camera in a manner such that, when viewed from the camera, the plurality of images is taken by the camera sequentially and in a clockwise or counterclockwise order. For example, FIG. 50A shows an example manner of taking images sequentially in a clockwise order viewed from the camera. In some embodiments, the positioning mechanism adjusts the relative location of the carrier to the camera is in a manner such that, when viewed from the camera, the plurality of images is taken by the camera sequentially and in a progressive scan order. FIG. 50B shows an example manner of taking images sequentially in a progressive scan order.

In some embodiments, the first and the second images are combined before performing further image analysis. In some cases, the first and second images may have an overlapped portion due to the adjustment of the camera or carrier positions. The overlapped portion can be removed using image processing techniques to form the combined image.

As shown in FIGS. 50A-B, the edge of the first image can be a bottom side of the first image and the edge of the second image can be a top side of the second image. In some cases, the edge of the first image is a top side of the first image and the edge of the second image is a bottom side of the second image. The edge of the first image can also be a left side of the first image and the edge of the second image can be a right side of the second image. Similarly, the edge of the first image can be a right side of the first image and the edge of the second image can be a left side of the second image.

As discussed in connection to FIG. 16, the testing equipment calculates the concentration of the sperms based on a volume of the specimen, which is the area of the captured specimen holding area times the distance between the specimen holding area and the bottom of the cover. However, due to manufacturing inaccuracy, the volume of the specimen may not be exact as the distance between the specimen holding area and the bottom of the cover can vary. In order to compensate for the inaccuracy and determine the actual volume of the specimen, the testing equipment can include a camera module with a focusing motor, such as a voice coil motor (VCM), a ceramic piezoelectric actuator, a focusing mechanism for a monocular camera, or a servo motor mechanism for a microscope, etc. The focusing motor is operable to drive the camera lens to adjust focal points of the camera. FIGS. 51A-B show an example of an adjustable lens of the camera module. In FIG. 51A, the lens is at an initial or default position, corresponding to a first focal length of the lens. In FIG. 51B, the lens has been extended to its maximum length, corresponding to a second focal length of the lens. The difference between the two lens positions forms a distance L, which can be divided into multiple steps, each corresponding to a change in focal length. Therefore, by knowing the lens positions when two target objects are in focus respectively, a distance between the two target objects can be derived.

Figure 52:
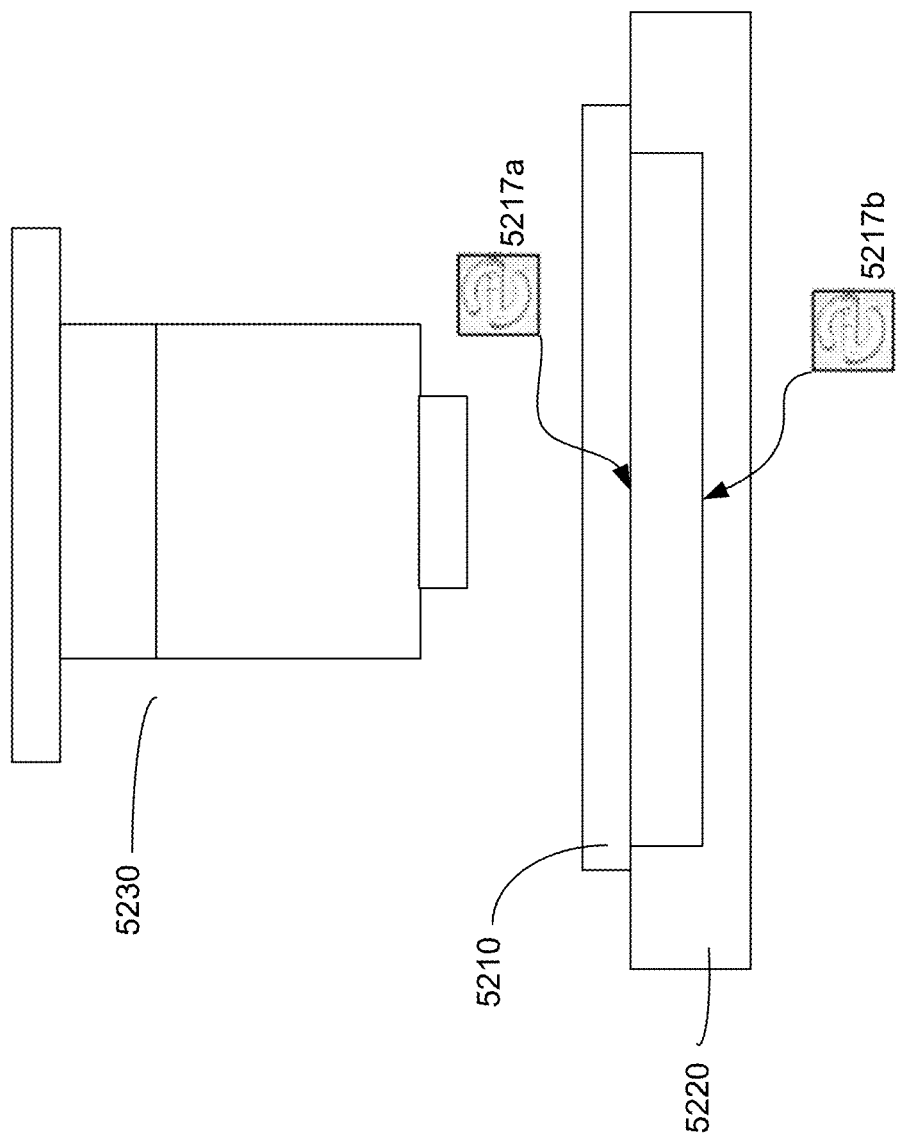
FIG. 52 shows an example configuration of determining an actual volume of a specimen in a carrier.

FIG. 52 shows an example configuration of determining an actual volume of a specimen in a carrier. A cover 5210 is placed on top of the carrier 5220 before the carrier 5220 is inserted for capturing images of the specimen. A first visual cue 5217a (e.g., as shown in FIG. 31) can be placed at the bottom surface of the cover 5210. A second visual cue 5217b can be placed at the surface that is in contact with or has been exposed to the specimen of the carrier 5220.

Before analyzing the biological specimen in the carrier, the device can first determine a first focusing position of the camera module 5230 for the cover 5220. This can be performed by adjusting the lens so that the first visual cue 5217a is in focus. The device can also determine a second focusing position for the carrier 5210 by adjusting the lens so that the second visual cue 5217b is in focus. The device then determines the focal lengths corresponding to the two focusing positions and calculates the distance between the first surface of the cover 5210 and the second surface of the carrier 5220. This process can be carried out in a configuration stage before analyzing a batch of samples (e.g., carriers and covers in the batch may be manufactured in the same lot such that they have the same properties). To achieve more accurate reading of the specimen, this process can also be performed during the use stage in case each carrier and cover have different properties.

In one specific example, the lens of the camera module supports focal lengths in a range of 50 μm to 550 μm. This range corresponds to the distance L between the two lens positions as shown in FIGS. 51A-B. The distance L, in some implementations, can be divided into 1024 steps (step 0, step 1, . . . step 1023), each corresponding to a particular focal length (that is, each step corresponds to (550−50)/1024=0.49 μm difference in focal length). In the configuration stage, the testing equipment first determines that the focusing position for the first visual cue 5217a is at step 235. The equipment then determines that the focusing position for the second visual cue 5217b is at step 295. A difference of (295−235)=60 steps corresponds to a difference of 60×0.49=29.4 μm in focal length, which indicates the actual distance between the bottom surface of the cover and the top surface of the carrier. The actual volume of the specimen can be determined based on the distance and the area of the captured specimen holding area.

In some embodiments, the cover 5210 and the carrier 5220 can have multiple visual cues positioned at either the top or the bottom surfaces. The measurement can be performed at different locations of the holding area to achieve a more accurate reading. It is noted that the ratio between the focal length to the distance can be different according to different lens designs. The specific example described above adopts a ratio of 1:1 (that is, the focal length of the lens is equal to the distance between the cover and the carrier). Various ratios between the focal length and the distance, such as 1:1.2, 1:1.5, 1:2, etc., can be supported.

Although some of the embodiments disclosed herein apply the disclosed technology to sperm test, a person having ordinary skill in the art readily appreciates that the disclosed technology can be applied to test various types of biological specimen, such as semen, urine, synovial joint fluid, epidermis tissues or cells, tumour cells, water sample, etc. Furthermore, the techniques described herein can also be applied to various analysis processes such as Sperm Chromatin Dispersion (SCD) or terminal deoxynucleotidyl transferase dUTP nick end labeling (TUNEL) for deoxyribonucleic acid (DNA) fragmentation detection. More specifically, in one or more implementations that can perform the SCD, the processor of the test equipment introduced herein can be configured to use the captured imagery captured to determine a normalcy of sperm DNA fragmentation. In some examples, when the heads of the sperms exhibit large or medium halo (the size of which is known in the art) under SCD, then the processor determines that there is no fragmentation in the sperm specimen being tested. On the contrary, when the heads of the sperms exhibit small halo, no halo, or degraded halo, then the processor determines that the sperm specimen being tested has DNA fragmentation issues. Furthermore, in one or more implementations that can perform TUNEL. In one or more implementations, the processor of the test equipment introduced herein can be configured to use the captured imagery to detect apoptotic DNA fragmentation. The processor can identify the one or more cells stained with TUNEL, thereby quantifying apoptotic cells and/or detecting excessive DNA breakage in individual cells.

In one example aspect, an apparatus for testing a biological specimen includes a receiving mechanism to receive a carrier. The carrier includes a holding area that is configured to carry the biological specimen. The device includes a camera module arranged to capture imagery of the holding area. The device also includes a processor that is configured to utilize the camera module to identify, from the captured imagery of the holding area, a visual cue on the carrier, and perform, based on a result of said identification of the visual cue, a set of analytic processes on the captured imagery. The identification of the visual cue includes verifying, based on a manner of how the visual cue is displayed in the captured imagery, whether the holding area carries the biological specimen and selectively causing the processor to perform the set of analytic processes on the captured imagery depending on a result of said verifying.

In some embodiments, the processor is caused to perform the set of analytic processes on the captured imagery only upon verifying that the holding area carries the biological specimen. In some embodiments, the processor is caused to not perform the set of analytic processes on the captured imagery upon failing to verify that the holding area carries the biological specimen. In some embodiments, the processor is further caused to display a predetermined signal or label associated with said failing to verify that the holding area carries the biological specimen.

In some embodiments, the manner of how the visual cue is displayed includes an optical distortion of the visual cue. In some embodiments, the optical distortion of the visual cue corresponds to a refractive index difference between the biological specimen and air. In some embodiments, verifying that the holding area carries the biological specimen includes comparing the optical distortion of the visual cue against a distortion threshold, wherein the distortion threshold represents a degree of optical distortion indicating an existence of the biological specimen in the holding area. In some embodiments, verifying that the holding area carries the biological specimen includes comparing the visual cue against stored imagery of the visual cue to determine a difference, wherein the holding area is verified as carrying the biological specimen when the difference is below a predetermined threshold.

In some embodiments, the processor is further configured to capture stored imagery of the visual cue during a configuration stage, during which the carrier is without any biological specimen. In some embodiments, the visual cue is in or near the holding area on the carrier. In some embodiments, the visual cue is identified when the visual cue exists in a predetermined shape or location. In some embodiments, the visual cue comprises a predetermined arrangement of a plurality of visual indicia.

In some embodiments, the apparatus includes a casing. The components are all enclosed within the casing. The form factor of the casing is smaller than 27,000 cubic centimeters. In some embodiments, the apparatus further includes a display enclosed within the casing. The processor is configured to display the determined outcome on the display after the outcome becomes available. In some embodiments, the display is configured to show a notification based on the result of said verifying. In some embodiments, the notification includes a signal or a label indicating that no biological specimen has been provided. In some embodiments, the processor is further configured to determine a biochemical property of the biological specimen using the set of analytic processes.

In another example aspect, an apparatus for testing a biological specimen includes a receiving mechanism to receive a carrier. The carrier includes a holding area that is configured to carry or to be exposed to the biological specimen. The apparatus includes a camera module arranged to capture a plurality of images of the holding area. The apparatus also includes a processor that is configured to utilize the camera module to adaptively select, based on the plurality of images of the holding area, an analytical algorithm suitable for a motion property of the biological specimen being tested and perform a set of analytic processes that corresponds to the selected analytic algorithm on the captured plurality of images to generate an analytic result associated with the biological specimen.

In some embodiments, the motion property is substantially static or substantially dynamic. In some embodiments, the processor is to adaptively select the analytic algorithm based on steps including determining an amount of variation between a first image and a second image among the plurality of images and selecting either a static algorithm or a dynamic algorithm depending on whether the determined amount of variation is smaller or larger than a threshold. In some embodiments, the amount of variation is determined based on a rate of change in motion of a detectable target in the biological specimen.

In some embodiments, the processor is to adaptively select the analytic algorithm based on steps including determining an amount of variation between a first image and a second image among the plurality of images, comparing the determined amount of variation against a threshold, and, based on a result of comparing the determined amount of variation against a threshold, selecting the analytical algorithm suitable for the motion property. In some embodiments, the analytical algorithm is a static algorithm or a dynamic algorithm. In some embodiments, the threshold is characteristic of whether the specimen is substantially static or dynamic. In some embodiments, the processor is configured to determine a motility of the biological specimen using the analytical algorithm. In some embodiments, when the determined amount of variation is less than the threshold, the selected algorithm is a static algorithm. In some embodiments, when the determined amount of variation is not less than the threshold, the selected algorithm is a dynamic algorithm.

In some embodiments, the processor is configured to determine a trajectory of the biological specimen using the dynamic algorithm. In some embodiments, the first and second images are taken temporally apart from each other for at least a given amount of time. In some embodiments, the given amount of time ranges from 0.04 seconds to 10 seconds. In some embodiments, the first and second images are taken sequentially apart from each other for at least a given amount of sequentially taken images. In some embodiments, the given amount of sequentially taken images ranges from 2 images to 600 images. In some embodiments, the apparatus further includes a casing, wherein said receiving mechanism, said camera module, and said processor are all enclosed within the casing, wherein a form factor of the casing is smaller than 27,000 cubic centimeters.

In another example aspect, an apparatus for testing a biological specimen includes a receiving mechanism to receive a carrier. The carrier includes a holding area is configured to carry or to be exposed to the biological specimen. The apparatus includes a camera, the camera being arranged to capture a plurality of images, including a first image and a second image, of the holding area and a positioning mechanism operable to adjust a relative location of the carrier to the camera. The apparatus also includes a processor that is configured to utilize the camera module to identify an edge of the first image, cause the positioning mechanism to adjust the relative location of the carrier to the camera in a manner such that, when the camera takes the second image, an edge of the second image is adjacent to or aligns with the identified edge of the first image and perform a set of analytic processes on a combined image from the first and second images to determine one or more properties of the biological specimen.

In some embodiments, the manner the positioning mechanism adjusts the relative location of the carrier to the camera is such that, when viewed from the camera, the plurality of images is taken by the camera sequentially and in a clockwise or counterclockwise order. In some embodiments, the manner the positioning mechanism adjusts the relative location of the carrier to the camera is determined according to multiple markers detectable by the camera. In some embodiments, the manner the positioning mechanism adjusts the relative location of the carrier to the camera is such that, when viewed from the camera, the plurality of images is taken by the camera sequentially and in a progressive scan order. The processor can be further configured to combine the first and the second images to form the combined image. In some embodiments, the set of analytic processes on a combined image excludes an overlap portion of the first and second images. In some embodiments, the one or more properties of the biological specimen include a cell count.

In some embodiments, the edge of the first image is a bottom side of the first image and the edge of the second image is a top side of the second image. In some embodiments, the edge of the first image is a top side of the first image and the edge of the second image is a bottom side of the second image. In some embodiments, the edge of the first image is a left side of the first image and the edge of the second image is a right side of the second image. In some embodiments, the edge of the first image is a right side of the first image and the edge of the second image is a left side of the second image.

In some embodiments, in adjusting the relative location of the carrier to the camera, the positioning mechanism is to adjust the carrier to a next position for a subsequent image to be taken by the camera. In some embodiments, in adjusting the relative location of the carrier to the camera, the positioning mechanism is to adjust the camera to a next position for a subsequent image to be taken by the camera. In some embodiments, the processor automatically adjusts the relative location of the carrier to the camera after the first image is taken by the camera.

In some embodiments, the positioning mechanism is configured to adjust the camera to a plurality of fixed positions automatically. In some embodiments, the positioning mechanism includes a multi-axis mobile platform configured to adjust the carrier or the camera to a plurality of positions. In some embodiments, the multi-axis mobile platform is configured to enable the carrier to be adjusted manually. In some embodiments, wherein the multi-axis mobile platform is configured to adjust the carrier automatically. In some embodiments, the apparatus further includes a casing. Said receiving mechanism, said camera module, and said processor are all enclosed within the casing, which has a form factor that is smaller than 27,000 cubic centimeters.

In yet another example aspect, an apparatus for testing a biological specimen includes a receiving mechanism to receive a carrier. The carrier includes a holding area that is configured to carries or has been exposed to the biological specimen. The apparatus includes a camera module arranged to capture imagery of the holding area. The camera module includes an focusing motor operable to adjust a focal point of the camera. The apparatus also includes a processor that is configured to utilize the camera module to determine, based on operations of the focusing motor, a volumetric property of the holding area and perform a set of analytic processes on at least a portion of the captured imagery of the holding area to determine one or more properties of the biological specimen. The one or more properties of the biological specimen receives adjustment by the processor based on the determined volumetric property of the holding area.

In some embodiments, the processor is configured to determine the volumetric property of the holding area based on operating the focusing motor to focus on different locations of the holding area. In some embodiments, the processor is configured to estimate a depth of the holding area in determining the volumetric property of the holding area. In some embodiments, the processor is further configured to perform a calculation to convert the estimated depth of the holding area into the volumetric property of the holding area.

In some embodiments, the processor is configured to determine the volumetric property of the holding area by causing the camera to focus, as a first focal point, on either one of a cover or the holding area, measuring a first depth for the first focal point, causing the camera to focus, as a second focal point, on the other one of the cover or the holding area, and measuring a second depth for the second focal point. In some embodiments, each of the cover and the holding area includes a visual indicium enabling the camera to focus. In some embodiments, a bottom surface of the cover includes the visual indicium. In some embodiments, the visual indicium is placed at a surface of the holding area that is in contact with or has been exposed to the biological specimen. The visual indicium can microscopic in size.

In some embodiments, the first and second depths are measured based on operations of the focusing motor. The first and second depths can be measured based on how many steps the focusing motor operates in order to reach from a default point to the first and second focal points, respectively. In some embodiments, a total travel available for the focal point adjustment is predefined, and a total number of available steps corresponds to the total travel available for the focal point adjustment. In some embodiments, the focusing motor includes a voice coil motor (VCM), a ceramic piezoelectric actuator, a focusing mechanism for a monocular camera, or a servo motor mechanism for a microscope. In some embodiments, the one or more properties of the biological specimen include concentration of the biological specimen. In some embodiments, the biological specimen is semen.

In some embodiments, the volumetric property of the holding area is determined during a configuration phase. In some embodiments, the analytic processes on the biological specimen is performed during normal use. In some embodiments, the apparatus further includes a casing. Said receiving mechanism, said camera module, and said processor are all enclosed within the casing, which has a form factor smaller than 27,000 cubic centimeters.

It will be apparent to those skilled in the art that various modifications and variations can be made to the structure of the present invention without departing from the scope or spirit of the invention. In view of the foregoing, it is intended that the present invention cover modifications and variations of this invention provided they fall within the scope of the following claims and their equivalents.

What is claimed is:

1. An apparatus for testing a biological specimen, the apparatus comprising:
   a receiving mechanism to receive a carrier, wherein the carrier includes a holding area, wherein the holding area is configured to or has been exposed to the biological specimen;
   a camera module arranged to capture imagery of the holding area, the camera module including an focusing motor operable to adjust a focal point of the camera;
   a processor that is configured to utilize the camera module to:
      determine, based on operations of the focusing motor, a volumetric property of the holding area; and
      perform a set of analytic processes on at least a portion of the captured imagery of the holding area to determine one or more properties of the biological specimen, wherein the one or more properties of the biological specimen receive adjustment by the processor based on the determined volumetric property of the holding area; and a casing, wherein said receiving mechanism, said camera module, and said processor are all enclosed within the casing, wherein a form factor of the casing is smaller than 27,000 cubic centimeters.

2. The apparatus of claim 1, wherein the processor is configured to determine the volumetric property of the holding area based on operating the focusing motor to focus on different locations of the holding area.

3. The apparatus of claim 1, wherein the processor is configured to estimate a depth of the holding area in determining the volumetric property of the holding area.

4. The apparatus of claim 3, wherein the processor is further configured to perform a calculation to convert the estimated depth of the holding area into the volumetric property of the holding area.

5. The apparatus of claim 1, wherein the processor is configured to determine the volumetric property of the holding area by:
    causing the camera to focus, as a first focal point, on either one of a cover or the holding area;
    measuring a first depth for the first focal point;
    causing the camera to focus, as a second focal point, on the other one of the cover or the holding area; and
    measuring a second depth for the second focal point.

6. The apparatus of claim 5, wherein each of the cover and the holding area includes a visual indicium enabling the camera to focus.

7. The apparatus of claim 6, wherein a bottom surface of the cover includes the visual indicium.

8. The apparatus of claim 6, wherein the visual indicium is placed at a surface of the holding area that is in contact with or has been exposed to the biological specimen.

9. The apparatus of claim 6, wherein the visual indicium is microscopic in size.

10. The apparatus of claim 5, wherein the first and second depths are measured based on operations of the focusing motor.

11. The apparatus of claim 5, wherein the first and second depths are measured based on how many steps the focusing motor operates in order to reach from a default point to the first and second focal points, respectively.

12. The apparatus of claim 11, wherein a total travel available for the focal point adjustment is predefined, and wherein a total number of available steps corresponds to the total travel available for the focal point adjustment.

13. The apparatus of claim 5, wherein the focusing motor includes a voice coil motor (VCM), a ceramic piezoelectric actuator, a focusing mechanism for a monocular camera, or a servo motor mechanism for a microscope.

14. The apparatus of claim 5, wherein the one or more properties of the biological specimen include concentration of the biological specimen.

15. The apparatus of claim 5, wherein the biological specimen is semen.

16. The apparatus of claim 5, wherein the volumetric property of the holding area is determined during a configuration phase.

17. The apparatus of claim 5, wherein the analytic processes on the biological specimen is performed during normal use.

18. An apparatus for testing a biological specimen, the apparatus comprising:

a receiving mechanism to receive a carrier, wherein the carrier includes a holding area, wherein the holding area is configured to or has been exposed to the biological specimen;

a camera module arranged to capture imagery of the holding area, the camera module including an focusing motor operable to adjust a focal point of the camera; and a processor that is configured to utilize the camera module to:
    determine, based on operations of the focusing motor, a volumetric property of the holding area; and
    perform a set of analytic processes on at least a portion of the captured imagery of the holding area to determine one or more properties of the biological specimen, wherein the one or more properties of the biological specimen receive adjustment by the processor based on the determined volumetric property of the holding area, wherein the processor is configured to estimate a depth of the holding area in determining the volumetric property of the holding area, and wherein the processor is further configured to perform a calculation to convert the estimated depth of the holding area into the volumetric property of the holding area.

19. The apparatus of claim 18, wherein the processor is configured to determine the volumetric property of the holding area based on operating the focusing motor to focus on different locations of the holding area.

20. An apparatus for testing a biological specimen, the apparatus comprising:

a receiving mechanism to receive a carrier, wherein the carrier includes a holding area, wherein the holding area is configured to or has been exposed to the biological specimen;

a camera module arranged to capture imagery of the holding area, the camera module including an focusing motor operable to adjust a focal point of the camera; and a processor that is configured to utilize the camera module to:
    determine, based on operations of the focusing motor, a volumetric property of the holding area; and
    perform a set of analytic processes on at least a portion of the captured imagery of the holding area to determine one or more properties of the biological specimen, wherein the one or more properties of the biological specimen receive adjustment by the processor based on the determined volumetric property of the holding area, and wherein the processor is configured to determine the volumetric property of the holding area by:
        causing the camera to focus, as a first focal point, on either one of a cover or the holding area;
        measuring a first depth for the first focal point;
        causing the camera to focus, as a second focal point, on the other one of the cover or the holding area; and
        measuring a second depth for the second focal point.

21. The apparatus of claim 20, wherein each of the cover and the holding area includes a visual indicium enabling the camera to focus.

22. The apparatus of claim 20, wherein the first and second depths are measured based on operations of the focusing motor.

* * * * *